US011325979B2

(12) United States Patent
Pirrello et al.

(10) Patent No.: US 11,325,979 B2
(45) Date of Patent: May 10, 2022

(54) TREATMENT OF CYTOKINE RELEASE SYNDROME WITH GM-CSF ANTAGONISTS

(71) Applicant: Kiniksa Pharmaceuticals, Ltd., Hamilton (BM)

(72) Inventors: Joe Pirrello, Lexington, MA (US); John Paolini, Lexington, MA (US); Eben Tessari, Lexington, MA (US)

(*) Notice: Subject to any disclaimer, the term of this patent is extended or adjusted under 35 U.S.C. 154(b) by 0 days.

(21) Appl. No.: 17/324,931

(22) Filed: May 19, 2021

(65) Prior Publication Data

US 2021/0284745 A1 Sep. 16, 2021

Related U.S. Application Data

(62) Division of application No. 17/201,698, filed on Mar. 15, 2021.

(60) Provisional application No. 62/989,841, filed on Mar. 15, 2020, provisional application No. 63/002,325, filed on Mar. 30, 2020, provisional application No. 63/007,875, filed on Apr. 9, 2020, provisional application No. 63/009,267, filed on Apr. 13, 2020, provisional application No. 63/012,090, filed on Apr. 18, 2020, provisional application No. 63/016,043, filed on Apr. 27, 2020, provisional application No. 63/026,010, filed on May 16, 2020, provisional application No. 63/029,160, filed on May 22, 2020, provisional application No. 63/128,752, filed on Dec. 21, 2020.

(51) Int. Cl.
*C07K 16/28* (2006.01)
*A61P 31/14* (2006.01)
*A61K 31/573* (2006.01)
*A61K 31/685* (2006.01)
*A61K 39/00* (2006.01)

(52) U.S. Cl.
CPC ........ *C07K 16/2866* (2013.01); *A61K 31/573* (2013.01); *A61K 31/685* (2013.01); *A61P 31/14* (2018.01); *A61K 2039/545* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 2009/0130093 A1 | 5/2009 | Cohen et al. | |
| 2012/0141464 A1 | 6/2012 | Cohen et al. | |
| 2014/0079708 A1 | 3/2014 | Cohen et al. | |
| 2015/0376285 A1 | 12/2015 | Cohen et al. | |
| 2016/0362476 A1 | 12/2016 | Weiner et al. | |

FOREIGN PATENT DOCUMENTS

| | | |
|---|---|---|
| ER | 2766394 B1 | 8/2014 |
| WO | WO 2006/122797 A2 | 11/2006 |
| WO | WO 2007/110631 A1 | 10/2007 |
| WO | WO 2013/053767 A1 | 4/2013 |
| WO | WO 2015/177097 A1 | 11/2015 |
| WO | WO 2017/076804 A1 | 5/2017 |
| WO | WO 2017/202879 A1 | 11/2017 |
| WO | WO 2019/070680 A2 | 4/2019 |
| WO | 2021183456 A1 | 9/2021 |

OTHER PUBLICATIONS

SARPAC Clinical Trial of Leukine (sargramostim, rhu GM-CSF) in Hospitalized COVID-19 Patients Meets Primary Endpoint ofof Significant Improvement in Lung Function, Partner Therapeutics, Inc. p. 1-7. (Year: 2021).*
Luca et al. (2020, Lancet Rhematolog, vol. 2, e465-473) (Year: 2020).*
Cramer et al. (2021, Lancet Rhematolog, vol. 3, e410-418) (Year: 2021).*
Altschul et al., "Basic local alignment search tool", Journal of molecular biology vol. 215(3): 403-10, (1990).
Altschul et al., "Gapped BLAST and PSI-BLAST: a new generation of protein database search programs", Nucleic acids research vol. 25(17): 3389-402, (1997).
Altschul et al., "Local alignment statistics", Methods in enzymology vol. 266: 460-80, (1996).
Baxevanis et al., "Bioinformatics: A Practical Guide to the Analysis of Genes and Proteins", Wiley, (1998).
Bonaventura et al., "Targeting GM-CSF in COVID-19 Pneumonia: Rationale and Strategies." Frontiers in immunology vol. 11 1625, (2020).
Cremer et al., "Mavrilimumab in patients with severe COVID-19 pneumonia and systemic hyperinflammation (MASH-COVID): an investigator initiated, multicentre, double-blind, randomised, placebo-controlled trial." The Lancet. Rheumatology vol. 3(6): e410-e418, (2021).

(Continued)

*Primary Examiner* — Gary B Nickol
*Assistant Examiner* — Jegatheesan Seharaseyon
(74) *Attorney, Agent, or Firm* — Proskauer Rose LLP

(57) ABSTRACT

The present invention provides, among other things, a method of treating a subject with infection-induced hyperinflammation comprising administering to the subject a granulocyte-macrophage colony-stimulating factor (GM-CSF) antagonist at a therapeutically effective dose and an administration interval for a treatment period sufficient to improve, stabilize or reduce one or more symptoms of hyperinflammation. The present invention also provides, among other things, a method of inhibiting or reducing cytokine release syndrome (CRS) or acute respiratory distress syndrome (ARDS) in a subject comprising administering to the subject a granulocyte-macrophage colony-stimulating factor (GM-CSF) antagonist at a therapeutically effective dose and an administration interval for a treatment period sufficient to improve, stabilize or reduce one or more symptoms of CRS or ARDS.

28 Claims, 13 Drawing Sheets
Specification includes a Sequence Listing.

(56) References Cited

OTHER PUBLICATIONS

De Luca et al., "GM-CSF blockade with mavrilimumab in severe COVID-19 pneumonia and systemic hyperinflammation: a single-centre, prospective cohort study." The Lancet. Rheumatology vol. 2(8): e465-e473, (2020).
Fisher et al., "Efficient isolation of soluble intracellular single-chain antibodies using the twin-arginine translocation machinery", Journal of molecular biology vol. 385(1): 299-311, (2009).
Hamilton et al., "GM-CSF Biology", Growth factors (Chur, Switzerland) vol. 22(4): 225-31, (2004).
Nava et al., "Non-invasive ventilation in acute respiratory failure", Lancet (London, England) vol. 374(9685): 250-9, (2009).
Remington's Pharmaceutical Sciences.
Wicks et al., "Targeting GM-CSF in inflammatory diseases", Nature reviews. Rheumatology vol. 12(1): 37-48, (2016).

\* cited by examiner

SEQUENCE LISTING

```
<160> NUMBER OF SEQ ID NOS: 8

<210> SEQ ID NO 1
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ile Val Gly Ser Phe Ser Pro Leu Thr Leu Gly Leu Trp Gly Gln
            100                 105                 110

Gly Thr Met Val Thr Val Ser Ser
        115                 120

<210> SEQ ID NO 2
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 2

Gln Ser Val Leu Thr Gln Pro Pro Ser Val Ser Gly Ala Pro Gly Gln
1               5                   10                  15
```

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ala Thr Val Glu Ala Gly
                85                  90                  95

Leu Ser Gly Ser Val Phe Gly Gly Gly Thr Lys Leu Thr Val Leu
            100                 105                 110

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Glu Leu Ser Ile His
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 4

Gly Phe Asp Pro Glu Glu Asn Glu Ile Val Tyr Ala Gln Arg Phe Gln
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 5

Val Gly Ser Phe Ser Pro Leu Thr Leu Gly Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 6

Thr Gly Ser Gly Ser Asn Ile Gly Ala Pro Tyr Asp Val Ser
1               5                   10

<210> SEQ ID NO 7
<211> LENGTH: 7
<212> TYPE: PRT
<213> ORGANISM: Artificial Sequence
<220> FEATURE:

```
<223> OTHER INFORMATION: Synthetic Polypeptide

<400> SEQUENCE: 7

His Asn Asn Lys Arg Pro Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

Ala Thr Val Glu Ala Gly Leu Ser Gly Ser Val
1               5                   10
```

TREATMENT OF CYTOKINE RELEASE SYNDROME WITH GM-CSF ANTAGONISTS

CROSS-REFERENCE TO RELATED APPLICATIONS

This application is a divisional application of U.S. application Ser. No. 17/201,698, which claims priority to, and the benefit of, U.S. provisional application No. 62/989,841, filed on Mar. 15, 2020, U.S. provisional application No. 63/002,325, filed on Mar. 30, 2020, U.S. provisional application No. 63/007,875, filed on Apr. 9, 2020, U.S. provisional application No. 63/009,267, filed on Apr. 13, 2020, U.S. provisional application No. 63/012,090, filed on Apr. 18, 2020, U.S. provisional application No. 63/016,043, filed on Apr. 27, 2020, U.S. provisional application No. 63/026,010, filed on May 16, 2020, U.S. provisional application No. 63/029,160, filed on May 22, 2020, and U.S. provisional application No. 63/128,752, filed on Dec. 21, 2020, the contents of each of which is hereby incorporated by reference in its entirety.

INCORPORATION-BY-REFERENCE OF SEQUENCE LISTING

The present specification makes reference to a Sequence Listing (submitted electronically as a .txt file named KPL-037US2_ST25 on May 19, 2021). The .txt file was generated on May 19, 2021 and is 4 KB in size. The entire contents of the sequence listing are herein incorporated by reference.

BACKGROUND

Acute Respiratory Distress Syndrome (ARDS) is a form of hypoxemic respiratory failure characterized by severe impairment in gas exchange and lung mechanics; with standard of care ARDS fatality rate is >40%. The mechanical cause of acute lung injury and ARDS is fluid leaked from the smallest blood vessels in the lungs into the tiny air sacs where blood is oxygenated. Normally, a protective membrane keeps this fluid in the vessels. Severe illness or injury, however, can cause damage to the membrane, leading to the fluid leakage of ARDS. ARDS has a wide range of underlying etiologies, including infection, inhalation of harmful substances, major trauma, and other less common causes. The majority of ARDS cases are the result of a hyperinflammation of the lung tissue as a consequence of an infectious insult in the subject that causes Cytokine Release Syndrome (CRS). The initial infection that drives the hyperinflammation in the lung tissue can be a non-pulmonary inflection, such as a widespread infection of the bloodstream originating from sources that include the peritoneum, urinary tract, soft tissue and skin. The initial infection can also be a pulmonary infection, such as severe pneumonia, which can be bacterial, viral, or less commonly, fungal. Viruses known to cause ARDS include Coronaviruses. Coronaviruses (CoVs) primarily target mucosal epithelia of respiratory and intestinal tracts resulting in respiratory and enteric symptoms. Although most infections result in mild self-limiting symptoms such as the common cold, novel emerging strains have been the causative agents of global outbreaks with significant health and economic impacts such as Severe Acute Respiratory Syndrome (SARS), Middle East Respiratory Syndrome (MERS) and Coronavirus Disease 2019 (COVID-19).

In the past decades, two known zoonotic coronaviruses, SARS-CoV and MERS-CoV, have been reported to damage the respiratory tract and cause severe outbreaks. Severe acute respiratory syndrome coronavirus 2 (SARS-CoV-2, also known as 2019-nCoV) is a newly discovered coronavirus, which was first discovered in Wuhan, China in December 2019. The disease was officially named Corona Virus Disease-19 (COVID-19) on 11 Feb. 2020. Epidemiological data have basically determined the route of person-to-person transmission in COVID-19. According to the Chinese Center for Disease Control and Prevention (CDC), as of Mar. 1, 2020, there were accumulatively confirmed 80,174 patients in China, including 2,915 cases of deaths. Most of the patients developed pneumonia, which can worsen rapidly into respiratory failure. The elderly and patient with low immune function have a higher susceptibility and mortality. One study reported that patients usually have pneumonia with abnormal findings on chest CT scan. Common symptoms at onset include fever, cough, and myalgia or fatigue. A large part of patients experienced severe complications including acute respiratory distress syndrome (ARDS) (29%), and 32% patients need an intensive care unit (ICU) admission and six (15%) died. In another report of 99 cases, 17 (17%) patients developed ARDS. Of which, 11 (11%) worsened within a few days and died. According to a new report, the mortality for critical cases reached 60.5%. Unfortunately, the pathogenesis of COVID-19 still remains unclear, and there is no efficient therapeutics.

Study demonstrated that in the pathogenesis of SARS, a cytokine storm occurred, involving a considerable release of proinflammatory cytokine including interleukins (IL)-6, tumor necrosis factor α (TNF-α), and IL-12. In the research of Middle East respiratory syndrome, caused by another coronavirus (MERS-CoV), cytokine genes of IL-6, IL-1β, and IL-8 can be markedly high. A delayed pro-inflammatory cytokine induction by MERS-CoV was also confirmed. Similar to the changes in SARS and MERS, in COVID-19, higher plasma levels of cytokines including IL-6, IL-2, IL-7, IL-10, granulocyte-colony stimulating factor (G-CSF), interferon-γ-inducible protein (IP10), monocyte chemoattractant protein (MCP1), macrophage inflammatory protein 1 alpha (MIP1A), and TNF-α were found in ICU patients, which implied a cytokine storm occurred, and related to the severity and prognosis of the disease. In the biopsy samples at autopsy from a patient who died from the severe infection with COVID-19, histological examination showed bilateral diffuse alveolar damage with cellular fibromyxoid exudates. Mononuclear inflammatory lymphocytes were seen in both lungs.

SUMMARY OF THE INVENTION

The present invention provides, among other things, a method of treating a subject infected with a virus, such as a coronavirus, by administering a GM-CSF antagonist. The present invention also provides methods for treating a subject infected with a virus, such as coronavirus, using a GM-CSF antagonist in combination with other antiviral therapies further described herein.

In one aspect, a method of treating a subject infected with a virus is provided comprising administering to the subject a granulocyte-macrophage colony-stimulating factor (GM-CSF) antagonist at a therapeutically effective dose and an administration interval for a treatment period sufficient to improve, stabilize or reduce one or more symptoms of viral infection.

In some embodiments, the virus is a coronavirus, an influenza A, an influenza B, a Rhinovirus, or an enterovirus. Accordingly, in some embodiments, the virus is a coronavirus. In some embodiments the virus is influenza A. In some embodiments the virus is influenza B. In some embodiments the virus is a Rhinovirus. In some embodiments the virus is an enterovirus.

In some embodiments, the coronavirus is the SARS, MERS, or COVID-19 coronavirus. Accordingly, in some embodiment the, coronavirus the SARS coronavirus. In some embodiments, the coronavirus is the MERS coronavirus. In some embodiments, the coronavirus is the COVID-19 coronavirus.

In some embodiments, the coronavirus is a SARS-CoV-2.

In some embodiments, the subject develops a lung disease.

In some embodiments, the lung disease is selected from bronchitis, pneumonia, pulmonary fibrosis, asthma, or acute respiratory distress syndrome. Accordingly, in some embodiments, the lung disease is bronchitis. In some embodiments, the lung disease is pneumonia. In one embodiment, the lung disease is COVID-19 pneumonia. In some embodiments, the lung disease is pulmonary fibrosis. In some embodiments, the lung disease is asthma. In some embodiments, the lung disease is acute respiratory distress syndrome.

In one aspect, a method is provided of inhibiting or reducing cytokine release syndrome (CRS) in a subject comprising administering to the subject a granulocyte-macrophage colony-stimulating factor (GM-CSF) antagonist at a therapeutically effective dose and an administration interval for a treatment period sufficient to improve, stabilize or reduce one or more symptoms of CRS. In some embodiments, the symptoms of CRS comprise hypotension, high fever, uncontrolled systemic inflammatory response with vasopressor-requiring circulatory shock, vascular leakage, disseminated intravascular coagulation, multi-organ system failure, cytopenias, elevated creatinine and liver enzymes, deranged coagulation parameters, elevated CRP, or combinations thereof. In one embodiment, the one or more symptoms of CRS is not a result of the administration of an immunotherapy (e.g., adoptive cell transfer, administration of monoclonal antibodies, administration of a cancer vaccine, T cell engaging therapies, or any combination thereof) to the subject.

In some embodiments, the CRS is associated with an infection. In some embodiments, the one or more symptoms comprise hyperinflammation of lung tissue. In one embodiment, the one or more symptoms comprise ARDS. In some embodiments, the one or more symptoms comprise hyperinflammation of cardiac tissue. In some embodiments, the one or more symptoms comprise pericarditis or myocarditis. In some embodiments, the one or more symptoms comprise hyperinflammation of renal tissue. In some embodiments, the infection is a viral infection. In some embodiments the infection is a bacterial infection. In some embodiments, the infection is a fungal infection. In some embodiments, the infection is any other infection driving hyperinflammation of the lung.

In some embodiments, the CRS is associated with graft-versus-host disease (GVHD). In some embodiments, the CRS is associated with pancreatitis. In some embodiments, the CRS is associated with acute kidney injury.

In one aspect, a method is provided of inhibiting or reducing cytokine release syndrome (CRS) associated with a virus infection in a subject comprising administering to the subject a granulocyte-macrophage colony-stimulating factor (GM-CSF) antagonist at a therapeutically effective dose and an administration interval for a treatment period sufficient to improve, stabilize or reduce one or more symptoms of CRS.

In one embodiment, a method is provided of inhibiting or reducing cytokine release syndrome (CRS) in the lung(s) of a subject with COVID-19 pneumonia.

In one aspect, the present invention provides, among other things, a method of inhibiting or reducing acute respiratory distress syndrome (ARDS) in a subject comprising administering to the subject a granulocyte-macrophage colony-stimulating factor (GM-CSF) antagonist at a therapeutically effective dose and an administration interval for a treatment period sufficient to improve, stabilize or reduce one or more symptoms of ARDS.

In some embodiments, the ARDS is associated with non-thoracic trauma. In some embodiments, the ARDS is associated with post thoracic surgery. In some embodiments, the ARDS is associated aspiration or toxic exposure. In some embodiments, the ARDS is associated with non-pulmonary infections. In some embodiments, the ARDS is associated with a pulmonary infection. In some embodiments, the infection is a bacterial or fungal infection. In some embodiments, the infection is a viral infection.

In some embodiments, the virus is a coronavirus, an influenza A, an influenza B, a Rhinovirus, or an enterovirus. Accordingly, in some embodiments, the virus is a coronavirus. In some embodiments the virus is influenza A. In some embodiments the virus is influenza B. In some embodiments the virus is a Rhinovirus. In some embodiments the virus is an enterovirus.

In some embodiments, the coronavirus is the SARS, MERS, or COVID-19 coronavirus. In some embodiments, a virus is SARS-CoV-2 or a derivative thereof. Accordingly, in some embodiment the coronavirus is SARS. In some embodiments, the coronavirus is MERS. In some embodiments, the coronavirus is associated with COVID-19 disease.

In some embodiments, the one or more symptoms are associated with SARS, MERS, or COVID-19. Accordingly, in some embodiments, the one or more symptoms are associated with SARS. In some embodiments, the one or more symptoms are associated with MERS. In some embodiments, the one or more symptoms are associated with COVID-19.

In some embodiments, the one more symptoms associated with COVID-19 are fever, cough, fatigue, coughing up sputum from the lungs, bone or joint pain, sore throat, headache, chills, nausea or vomiting, stuffy nose, or shortness of breath.

In some embodiments, the one or more symptoms are associated with a respiratory tract infection, pneumonia, pulmonary fibrosis, asthma, or acute respiratory distress syndrome. In one embodiment, the lung disease is COVID-19 pneumonia.

In some embodiments, the respiratory tract infection is a lower respiratory tract infection.

In some embodiments, the respiratory tract infection is an upper respiratory tract infection.

In some embodiments, the subject has an elevated level of an inflammation marker.

In some embodiments, the elevated level of the inflammation marker is detected in the serum of the subject.

In some embodiments, the elevated level of the inflammation marker is detected in the lung of the subject.

In some embodiments, the inflammation marker is a presence of ground-glass opacity.

In some embodiments, the elevated level of the inflammation marker in a subject's serum is c-reactive protein (CRP)≥1 mg/dL. Accordingly, in some embodiments the level of CRP is about 1 mg/dL. In some embodiments, the level of CRP is about 2 mg/dL. In some embodiments, the level of CRP is about 3 mg/dL. In some embodiments, the level of CRP is about 4 mg/dL. In some embodiments, the level of CRP is about 5 mg/dL. In some embodiments, the level of CRP is about 6 mg/dL. In some embodiments, the level of CRP is about 7 mg/dL. In some embodiments, the level of CRP is about 8 mg/dL. In some embodiments, the level of CRP is about 9 mg/dL. In some embodiments, the level of CRP is about 10 mg/dL. In some embodiments, the level of CRP is about 11 mg/dL. In some embodiments, the level of CRP is about 12 mg/dL. In some embodiments, the level of CRP is about 13 mg/dL. In some embodiments, the level of CRP is about 14 mg/dL. In some embodiments, the level of CRP is about 15 mg/dL. In some embodiments, the level of CRP is about 10 mg/dL. In some embodiments, the level of CRP is about 16 mg/dL. In some embodiments, the level of CRP is about 17 mg/dL. In some embodiments, the level of CRP is about 18 mg/dL. In some embodiments, the level of CRP is about 19 mg/dL. In some embodiments, the level of CRP is about 20 mg/dL.

In some embodiments, the level of CRP is between 0.5-10 mg/dL. In some embodiments, the level of CRP is between 5-10 mg/dL. In some embodiments, the level of CRP is between 1-9 mg/dL. In some embodiments, the level of CRP is 5-9 mg/dL.

In some embodiments, the elevated level of the inflammation marker in a subject's serum is c-reactive protein (CRP)≥10 mg/L. Accordingly, in some embodiments the level of CRP is about 10 mg/L. In some embodiments, the level of CRP is about 20 mg/L. In some embodiments, the level of CRP is about 30 mg/L. In some embodiments, the level of CRP is about 40 mg/L. In some embodiments, the level of CRP is about 50 mg/L. In some embodiments, the level of CRP is about 60 mg/L. In some embodiments, the level of CRP is about 70 mg/L. In some embodiments, the level of CRP is about 80 mg/L. In some embodiments, the level of CRP is about 90 mg/L. In some embodiments, the level of CRP is about 100 mg/L. In some embodiments, the level of CRP is about 110 mg/L. In some embodiments, the level of CRP is about 120 mg/L. In some embodiments, the level of CRP is about 130 mg/L. In some embodiments, the level of CRP is about 140 mg/L. In some embodiments, the level of CRP is about 150 mg/L. In some embodiments, the level of CRP is about 100 mg/L. In some embodiments, the level of CRP is about 160 mg/L. In some embodiments, the level of CRP is about 170 mg/L. In some embodiments, the level of CRP is about 180 mg/L. In some embodiments, the level of CRP is about 190 mg/L. In some embodiments, the level of CRP is about 200 mg/L.

In some embodiments, the level of CRP is between 5-100 mg/L. In some embodiments, the level of CRP is between 50-100 mg/L. In some embodiments, the level of CRP is between 10-90 mg/L. In some embodiments, the level of CRP is 50-90 mg/L.

In some embodiments, a subject's D-dimer level is greater than 0.1 µg/ml at baseline. In some embodiments, a subject's D-dimer level is greater than 0.5 µg/ml at baseline. In some embodiments, a subject's D-dimer level is greater than 0.6 µg/ml at baseline. In some embodiments, a subject's D-dimer level is greater than 0.7 µg/ml at baseline. In some embodiments, a subject's D-dimer level is greater than 0.8 µg/ml at baseline. In some embodiments, a subject's D-dimer level is greater than 0.9 µg/ml at baseline. In some embodiments, a subject's D-dimer level is greater than 1.0 µg/ml at baseline. In some embodiments, a subject's D-dimer level is greater than 1.5 µg/ml at baseline. In some embodiments, a subject's D-dimer level is greater than 2.0 µg/ml at baseline. In some embodiments, a subject's D-dimer level is greater than 2.5 µg/ml at baseline. In some embodiments, a subject's D-dimer level is greater than 3.0 µg/ml at baseline. In some embodiments, a subject's D-dimer level is greater than 4.0 µg/ml at baseline. In some embodiments, a subject's D-dimer level is greater than 5.0 µg/ml at baseline. In some embodiments, a subject's D-dimer level is greater than 8.0 µg/ml at baseline. In some embodiments, a subject's D-dimer level is greater than 10.0 µg/ml at baseline. In some embodiments, a subject's D-dimer level is greater than 12.0 µg/ml at baseline. In some embodiments, a subject's D-dimer level is greater than 15.0 µg/ml at baseline. In some embodiments, a subject's D-dimer level is greater than 20.0 µg/ml at baseline. In some embodiments, a subject's D-dimer level is greater than 25.0 µg/ml at baseline. In some embodiments, a subject's D-dimer level is greater than 30.0 µg/ml at baseline. In some embodiments, a subject's D-dimer level is greater than 40.0 µg/ml at baseline. In some embodiments, a subject's D-dimer level is greater than 50.0 µg/ml at baseline.

In some embodiments, the method comprises selecting a subject who has an elevated level of the inflammation marker in a subject's serum. In some embodiments, the method comprises selecting a subject based on the level of C-reactive protein (CRP). In some embodiments, a subject is selected based on the level of CRP at baseline. In some embodiments, a subject is selected with CRP levels above normal (0.5 mg/dL or 5 mg/L). In some embodiments, a subject's CRP level is greater than 10-fold over the normal level at baseline. In some embodiments, a subject's CRP level is about 5 mg/dL at baseline. In some embodiments, a subject is selected based on the level of CRP lower than 10 mg/dL at baseline. In some embodiments, a subject is selected based on the level of CRP lower than 8 mg/dL at baseline. In some embodiments, a subject's CRP level is less than 6 mg/dL at baseline. In some embodiments, a subject's CRP level is less than 5 mg/dL at baseline. In some embodiments, a subject's CRP level is less than 4 mg/dL at baseline. In some embodiments, a subject's CRP level is between 0.5 and 10 mg/dL at baseline. In some embodiments, a subject's CRP level is between 1 and 5 mg/dL at baseline. In some embodiments, a subject's CRP level is between 3 and 7 mg/dL at baseline. In some embodiments, a subject's CRP level is between 4 and 6 mg/dL at baseline.

In some embodiments, a subject's CRP level is about 50 mg/L at baseline. In some embodiments, a subject is selected based on the level of CRP lower than 100 mg/L at baseline. In some embodiments, a subject is selected based on the level of CRP lower than 80 mg/L at baseline. In some embodiments, a subject's CRP level is less than 60 mg/L at baseline. In some embodiments, a subject's CRP level is less than 50 mg/L at baseline. In some embodiments, a subject's CRP level is less than 40 mg/L at baseline. In some embodiments, a subject's CRP level is between 5 and 100 mg/L at baseline. In some embodiments, a subject's CRP level is between 10 and 50 mg/L at baseline. In some embodiments, a subject's CRP level is between 30 and 70 mg/L at baseline. In some embodiments, a subject's CRP level is between 40 and 60 mg/L at baseline.

In some embodiments, the method comprises selecting a subject who has an elevated level of the D-dimer. In some embodiments, a subject is selected based on the level of D-dimer at baseline. In some embodiments, a subject is selected with D-dimer levels above normal (0.1 µg/ml). In some embodiments, a subject's D-dimer level is greater than 2, 3, 4, 5, 8, or 10-fold over the normal level at baseline. In some embodiments, the subject's D-dimer level is greater than 0.1 µg/ml at baseline. In some embodiments, the subject's D-dimer level is greater than 0.5 µg/ml at baseline. In some embodiments, the subject's D-dimer level is greater than 1.0 µg/ml at baseline.

In some embodiments, the administering the GM-CSF antagonist decreases the level of CRP to <1 mg/dL or <10 mg/L. In some embodiments, following the administration of the GM-CSF antagonist, the CRP level is maintained at 1 mg/dL or less, or at 10 mg/L or less for longer than 1 day, 2 days, 3 days, 4 days, 5 days, 6 days, 7 days, 8 days, 9 days, 10 days, 11 days, 12 days, 13 days, 1 week, 2 weeks, 3 weeks, or for longer than 1 month. In some embodiments, the CRP level is maintained at 1 mg/dL or less or at 10 mg/L or less for the indicated period, while the patient continues to receive a therapeutic dose of the GM-CSF antagonist and optionally an antiviral drug, hydroxychloroquine, corticosteroids, or combinations thereof.

In some embodiments, the administering the GM-CSF antagonist decreases the level of CRP in a subject by 90% or more. In some embodiments, the administering the GM-CSF antagonist decreases the level of CRP in a subject by 80% or more. In some embodiments, the administering the GM-CSF antagonist decreases the level of CRP in a subject by 75% or more. In some embodiments, the administering the GM-CSF antagonist decreases the level of CRP in a subject by 70% or more. In some embodiments, the administering the GM-CSF antagonist decreases the level of CRP in a subject by 60% or more. In some embodiments, the administering the GM-CSF antagonist decreases the level of CRP in a subject by 50% or more. In some embodiments, the administering the GM-CSF antagonist decreases the level of CRP in a subject by 40% or more. In some embodiments, the administering the GM-CSF antagonist decreases the level of CRP in a subject by 30% or more. In some embodiments, the administering the GM-CSF antagonist decreases the level of CRP in a subject by 20% or more. In some embodiments, the administering the GM-CSF antagonist decreases the level of CRP in a subject by 10% or more.

In some embodiments, the administering the GM-CSF antagonist restores the level of CRP in a subject to the normal level (≤0.5 mg/dL or (≤5 mg/L). In some embodiments, the administering the GM-CSF antagonist decrease the level of CRP in a subject to 18 mg/dL or less. In some embodiments, the administering the GM-CSF antagonist decrease the level of CRP in a subject to 17 mg/dL or less. In some embodiments, the administering the GM-CSF antagonist decrease the level of CRP in a subject to 16 mg/dL or less. In some embodiments, the administering the GM-CSF antagonist decrease the level of CRP in a subject to 15 mg/dL or less. In some embodiments, the administering the GM-CSF antagonist decrease the level of CRP in a subject to 14 mg/dL or less. In some embodiments, the administering the GM-CSF antagonist decrease the level of CRP in a subject to 13 mg/dL or less. In some embodiments, the administering the GM-CSF antagonist decrease the level of CRP in a subject to 12 mg/dL or less. In some embodiments, the administering the GM-CSF antagonist decrease the level of CRP in a subject to 10 mg/dL or less. In some embodiments, the administering the GM-CSF antagonist decrease the level of CRP in a subject to 9 mg/dL or less. In some embodiments, the administering the GM-CSF antagonist decrease the level of CRP in a subject to 8 mg/dL or less. In some embodiments, the administering the GM-CSF antagonist decrease the level of CRP in a subject to 7 mg/dL or less. In some embodiments, the administering the GM-CSF antagonist decrease the level of CRP in a subject to 6 mg/dL or less. In some embodiments, the administering the GM-CSF antagonist decrease the level of CRP in a subject to 5 mg/dL or less. In some embodiments, the administering the GM-CSF antagonist decrease the level of CRP in a subject to 3 mg/dL or less. In some embodiments, the administering the GM-CSF antagonist decrease the level of CRP in a subject to 2 mg/dL or less. In some embodiments, the administering the GM-CSF antagonist decrease the level of CRP in a subject to 1 mg/dL or less. In some embodiments, the administering the GM-CSF antagonist decrease the level of CRP in a subject within 1 hour, 2 hours, 4 hours, 6 hours, 12 hours, 24 hours, 48 hours, 72 hours, 4 days, 5 days, 6 days, 7 days, or two weeks.

In some embodiments, the administering the GM-CSF antagonist decrease the level of CRP in a subject to 180 mg/L or less. In some embodiments, the administering the GM-CSF antagonist decrease the level of CRP in a subject to 170 mg/L or less. In some embodiments, the administering the GM-CSF antagonist decrease the level of CRP in a subject to 160 mg/L or less. In some embodiments, the administering the GM-CSF antagonist decrease the level of CRP in a subject to 150 mg/L or less. In some embodiments, the administering the GM-CSF antagonist decrease the level of CRP in a subject to 140 mg/L or less. In some embodiments, the administering the GM-CSF antagonist decrease the level of CRP in a subject to 130 mg/L or less. In some embodiments, the administering the GM-CSF antagonist decrease the level of CRP in a subject to 120 mg/L or less. In some embodiments, the administering the GM-CSF antagonist decrease the level of CRP in a subject to 100 mg/L or less. In some embodiments, the administering the GM-CSF antagonist decrease the level of CRP in a subject to 90 mg/L or less. In some embodiments, the administering the GM-CSF antagonist decrease the level of CRP in a subject to 80 mg/L or less. In some embodiments, the administering the GM-CSF antagonist decrease the level of CRP in a subject to 70 mg/L or less. In some embodiments, the administering the GM-CSF antagonist decrease the level of CRP in a subject to 60 mg/L or less. In some embodiments, the administering the GM-CSF antagonist decrease the level of CRP in a subject to 50 mg/L or less. In some embodiments, the administering the GM-CSF antagonist decrease the level of CRP in a subject to 30 mg/L or less. In some embodiments, the administering the GM-CSF antagonist decrease the level of CRP in a subject to 20 mg/L or less. In some embodiments, the administering the GM-CSF antagonist decrease the level of CRP in a subject to 10 mg/L or less.

In some embodiments, the administering the GM-CSF antagonist decreases the level of D-dimer in a subject by 90%. In some embodiments, the administering the GM-CSF antagonist decreases the level of D-dimer in a subject by 80%. In some embodiments, the administering the GM-CSF antagonist decreases the level of D-dimer in a subject by 70%. In some embodiments, the administering the GM-CSF antagonist decreases the level of D-dimer in a subject by 60%. In some embodiments, the administering the GM-CSF antagonist decreases the level of D-dimer in a subject by 50%. In some embodiments, the administering the GM-CSF antagonist decreases the level of D-dimer in a subject by 40%. In some embodiments, the administering the GM-CSF antagonist decreases the level of D-dimer in a subject by 30%. In some embodiments, the administering the GM-CSF antagonist decreases the level of D-dimer in a subject by 20%. In some embodiments, the administering the GM-CSF antagonist decreases the level of D-dimer in a subject by 10%.

In some embodiments, the administering the GM-CSF antagonist restores the level of D-dimer in a subject to the normal level (~0.1 µg/mL). In some embodiments, the administering the GM-CSF antagonist decrease the level of D-dimer in a subject to 1.0 µg/mL or less. In some embodiments, the administering the GM-CSF antagonist decrease the level of dimer in a subject to 0.5 µg/mL or less. In some embodiments, the administering the GM-CSF antagonist decrease the level of dimer in a subject to 0.3 µg/mL or less. In some embodiments, the administering the GM-CSF antagonist decrease the level of dimer in a subject to 0.2 µg/mL or less. In some embodiments, the administering the GM-CSF antagonist decrease the level of dimer in a subject to 0.1 µg/mL or less.

In some embodiments, the administering the GM-CSF antagonist decreases a quantity of a pro-inflammatory cytokine within the subject by between approximately 10% to approximately 90%.

In some embodiments, the administering the GM-CSF antagonist decreases a quantity of a pro-inflammatory cytokine within the subject by between approximately 25% to approximately 85%.

In some embodiments, the administering the GM-CSF antagonist decreases a quantity of a pro-inflammatory cytokine within the subject by between approximately 50% to approximately 75%.

In some embodiments, the administering the GM-CSF antagonist decreases a quantity of a pro-inflammatory cytokine within the subject by between approximately 70% to approximately 80%.

In some embodiments, the administering the GM-CSF antagonist decreases a quantity of pro-inflammatory cytokine within the subject by about 10%. In some embodiments, the administering the GM-CSF antagonist decreases a quantity of pro-inflammatory cytokine within the subject by about 15%. In some embodiments, the administering the GM-CSF antagonist decreases a quantity of pro-inflammatory cytokine within the subject by about 20%. In some embodiments, the administering the GM-CSF antagonist decreases a quantity of pro-inflammatory cytokine within the subject by about 25%. In some embodiments, the administering the GM-CSF antagonist decreases a quantity of pro-inflammatory cytokine within the subject by about 30%. In some embodiments, the administering the GM-CSF antagonist decreases a quantity of pro-inflammatory cytokine within the subject by about 35%. In some embodiments, the administering the GM-CSF antagonist decreases a quantity of pro-inflammatory cytokine within the subject by about 40%. In some embodiments, the administering the GM-CSF antagonist decreases a quantity of pro-inflammatory cytokine within the subject by about 45%. In some embodiments, the administering the GM-CSF antagonist decreases a quantity of pro-inflammatory cytokine within the subject by about 50%. In some embodiments, the administering the GM-CSF antagonist decreases a quantity of pro-inflammatory cytokine within the subject by about 55%. In some embodiments, the administering the GM-CSF antagonist decreases a quantity of pro-inflammatory cytokine within the subject by about 60%. In some embodiments, the administering the GM-CSF antagonist decreases a quantity of pro-inflammatory cytokine within the subject by about 65%. In some embodiments, the administering the GM-CSF antagonist decreases a quantity of pro-inflammatory cytokine within the subject by about 70%. In some embodiments, the administering the GM-CSF antagonist decreases a quantity of pro-inflammatory cytokine within the subject by about 75%. In some embodiments, the administering the GM-CSF antagonist decreases a quantity of pro-inflammatory cytokine within the subject by about 80%. In some embodiments, the administering the GM-CSF antagonist decreases a quantity of pro-inflammatory cytokine within the subject by about 85%. In some embodiments, the administering the GM-CSF antagonist decreases a quantity of pro-inflammatory cytokine within the subject by about 90%. In some embodiments, the administering the GM-CSF antagonist decreases a quantity of pro-inflammatory cytokine within the subject by 95%. In some embodiments, the administering the GM-CSF antagonist decreases a quantity of pro-inflammatory cytokine within the subject by greater than 95%.

In some embodiments, the pro-inflammatory cytokine is one of IL-1, IL-6, IL-7, IL-8, IL-10, IL-12, G-CSF, IP10, MCP1, MCP1A and TNF-α.

In some embodiments, the administering the GM-CSF antagonist increases a quantity of an anti-inflammatory cytokine in the subject.

In some embodiments, the administering the GM-CSF antagonist alleviates a cytokine imbalance in the subject.

In some embodiments, the administering the GM-CSF antagonist decreases a quantity of mononuclear inflammatory lymphocytes in the lung of the subject.

In some embodiments, the administering the GM-CSF antagonist decreases an area of ground-glass opacity in the lung.

In some embodiments, the administering the GM-CSF antagonist decreases an intensity of non-cardiogenic pulmonary edema. In some embodiments, the administering the GM-CSF antagonist improves the subject's lung function such supplemental oxygen is not needed. In some embodiments, the administering the GM-CSF antagonist results in the subject's weaning off the supplemental oxygen. In some embodiments, the administering the GM-CSF antagonist decreases the subject's dependency on the supplemental oxygen.

In some embodiments, supplemental oxygen is provided by a respirator or a mechanical ventilation.

In some embodiments, the administering the GM-CSF antagonist restores the level of hemoglobin oxygen saturation (sO2) to the normal level. Typically, the normal range of sO2 is between 94% and 98%. In some embodiments, the administering the GM-CSF antagonist increases the sO2 level in the subject to a range between 90% and 100%. In some embodiments, the administering the GM-CSF antagonist increases the sO2 level in the subject to a range between 92% and 99%. In some embodiments, the administering the GM-CSF antagonist increases the sO2 level in the subject to a range between 94% and 98%. In some embodiments, the administering the GM-CSF antagonist increases the sO2 level in the subject to 93% or higher, or 94% or higher.

In some embodiments, the administering the GM-CSF antagonist restores the level of partial pressure of oxygen (pO2) to the normal level. Typically, pO2 reflects the amount of oxygen gas dissolved in the blood. It primarily measures the effectiveness of the lungs in pulling oxygen into the blood stream from the atmosphere. The normal adult arterial value for pO2 is typically >80 torr. In some embodiments, the administering the GM-CSF antagonist increases the pO2 level in the subject to a range between 70 and 180 torr. In some embodiments, the administering the GM-CSF antagonist increases the pO2 level in the subject to a range between 80% and 160 torr. In some embodiments, the administering the GM-CSF antagonist increases the pO2 level in the subject to a range between 85 and 150 torr. In some embodiments, the administering the GM-CSF antagonist increases the pO2 level in the subject to 80 torr or higher, 85 torr or higher, 90 torr or higher, 95 torr or higher, or 100 torr or higher.

In some embodiments, the administering the GM-CSF antagonist restores measured partial pressure of arterial oxygen over the fraction of inspired oxygen (PaO2/FiO2). The fraction of fraction of inspired oxygen (FiO2). FiO2 is the molar or volumetric fraction of oxygen in the inhaled gas. Typically, medical patients experiencing difficulty breathing are provided with oxygen-enriched air, which means a higher-than-atmospheric FiO2. Natural air includes 21% oxygen, which is equivalent to FiO2 of 0.21. Normal person breathing room air (FiO2=0.21), whose PaO2 is approximately 100 mm Hg, would have a PaO2/FiO2 ratio of approximately 500. Typically, acute lung injury is present if PaO2/FiO2 ratio is less than 300, and acute respiratory distress syndrome is present if PaO2/FiO2 ratio is less than 200. In some embodiments, the administering the GM-CSF antagonist increases the PaO2/FiO2 ratio in the subject to 150 or higher. In some embodiments, the administering the GM-CSF antagonist increases the PaO2/FiO2 ratio in the subject to 160 or higher. In some embodiments, the administering the GM-CSF antagonist increases the PaO2/FiO2 ratio in the subject to 180 or higher. In some embodiments, the administering the GM-CSF antagonist increases the PaO2/FiO2 ratio in the subject to 200 or higher. In some embodiments, the administering the GM-CSF antagonist increases the PaO2/FiO2 ratio in the subject to 220 or higher. In some embodiments, the administering the GM-CSF antagonist increases the PaO2/FiO2 ratio in the subject to 240 or higher. In some embodiments, the administering the GM-CSF antagonist increases the PaO2/FiO2 ratio in the subject to 250 or higher. In some embodiments, the administering the GM-CSF antagonist increases the PaO2/FiO2 ratio in the subject to 260 or higher. In some embodiments, the administering the GM-CSF antagonist increases the PaO2/FiO2 ratio in the subject to 280 or higher. In some embodiments, the administering the GM-CSF antagonist increases the PaO2/FiO2 ratio in the subject to 300 or higher. In some embodiments, the administering the GM-CSF antagonist increases the PaO2/FiO2 ratio in the subject to 350 or higher. In some embodiments, the administering the GM-CSF antagonist increases the PaO2/FiO2 ratio in the subject to 400 or higher. In some embodiments, the administering the GM-CSF antagonist increases the PaO2/FiO2 ratio in the subject to 450 or higher. In some embodiments, the administering the GM-CSF antagonist increases the PaO2/FiO2 ratio in the subject to 500 or higher.

In some embodiments, the administering the GM-CSF antagonist alleviates fever within 1 day, within 2 days, or within 3 days. In some embodiments, the administering the GM-CSF antagonist prevents a subject from requiring mechanical ventilation.

In some embodiments, the step of administering comprises intravenous administration.

In some embodiments, the step of administering comprises subcutaneous administration.

In some embodiments, the step of administering comprises an initial loading dose. In some embodiments the initial loading dose is followed by at least one repeat dose.

In some embodiments, the therapeutically effective dose is between 37 mg and 750 mg.

In some embodiments, the therapeutically effective dose is about 30 mg, 35 mg, 40 mg, 45 mg, 50 mg, 55 mg, 60 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg. In some embodiments, the therapeutically effective dose is about 30 mg, 35 mg, 40 mg, 45 mg, 50 mg, 55 mg, 60 mg, 70 mg, 275 mg, 280 mg, 285 mg, 290 mg, 295 mg, 300 mg, 325 mg, 350 mg, 375 mg, 400 mg, 425 mg, 450 mg, 475 mg, 500 mg, 550 mg, 650 mg, 625 mg, 650 mg, 675 mg, 700 mg, 725 mg, or 750 mg.

In some embodiments, the therapeutically effective dose is about 225 mg. In some embodiments, the therapeutically effective dose is about 375 mg. In some embodiments, the therapeutically effective dose is about 450 mg. In some embodiments, the therapeutically effective dose is about 750 mg.

In some embodiments, the therapeutically effective dose is between 0.5 mg/kg and 3 mg/kg. In some embodiments, the therapeutically effective dose is about 0.5 mg/kg. In some embodiments, the therapeutically effective dose is about 1.0 mg/kg. In some embodiments, the therapeutically effective dose is about 1.5 mg/kg. In some embodiments, the therapeutically effective dose is about 2.0 mg/kg. In some embodiments, the therapeutically effective dose is about 2.5 mg/kg. In some embodiments, the therapeutically effective dose is about 3.0 mg/kg. In some embodiments, the therapeutically effective dose is between 3 mg/kg and 10 mg/kg. In some embodiments, the therapeutically effective dose is between 5 mg/kg and 10 mg/kg. In some embodiments, the therapeutically effective dose is about 3 mg/kg. In some embodiments, the therapeutically effective dose is about 4 mg/kg. In some embodiments, the therapeutically effective dose is about 5 mg/kg. In some embodiments, the therapeutically effective dose is about 6 mg/kg. In some embodiments, the therapeutically effective dose is about 7 mg/kg. In some embodiments, the therapeutically effective dose is about 8 mg/kg. In some embodiments, the therapeutically effective dose is about 9 mg/kg. In some embodiments, the therapeutically effective dose is about 10 mg/kg.

In some embodiments, the therapeutically effective dose is delivered to maintain a serum concentration of the GM-CSF antagonist between 100 ng/mL and 10000 ng/mL for at least 3 days. In some embodiments, the therapeutically effective dose is delivered to attain a serum concentration of the GM-CSF antagonist between about 100,000 ng/mL. In some embodiments, the therapeutically effective dose is delivered to attain a serum concentration of the GM-CSF antagonist between 3400 ng/mL and 8300 ng/ml.

In some embodiments, the therapeutically effective dose is delivered to maintain a serum concentration of the GM-CSF antagonist between 3400 ng/mL and 8300 ng/ml for at least 3 days, 4, days, 5 days, 1 week, 2 weeks, 3 weeks 5 weeks, or 6 weeks.

In some embodiments, the therapeutically effective dose is delivered to maintain a serum concentration of the GM-CSF antagonist between 3400 ng/mL and 8300 ng/ml for 1 day, 3 days, 4, days, 5 days, 1 week, 2 weeks, 3 weeks, 5 weeks, up to 6 weeks.

In some embodiments, the therapeutically effective dose is delivered to attain a serum concentration of GM-CSF antagonist at about 100 ng/mL. In some embodiments, the therapeutically effective dose is delivered to attain a serum concentration of GM-CSF antagonist at about 200 ng/mL. In some embodiments, the therapeutically effective dose is delivered to attain a serum concentration of GM-CSF antagonist at about 300 ng/mL. In some embodiments, the therapeutically effective dose is delivered to attain a serum concentration of GM-CSF antagonist at about 400 ng/mL. In some embodiments, the therapeutically effective dose is delivered to attain a serum concentration of GM-CSF antagonist at about 500 ng/mL. In some embodiments, the therapeutically effective dose is delivered to attain a serum concentration of GM-CSF antagonist at about 600 ng/mL. In some embodiments, the therapeutically effective dose is delivered to attain a serum concentration of GM-CSF antagonist at about 700 ng/mL. In some embodiments, the therapeutically effective dose is delivered to attain a serum concentration of GM-CSF antagonist at about 800 ng/mL. In some embodiments, the therapeutically effective dose is delivered to attain a serum concentration of GM-CSF antagonist at about 900 ng/mL. In some embodiments, the therapeutically effective dose is delivered to attain a serum concentration of GM-CSF antagonist at about 1,000 ng/mL. In some embodiments, the therapeutically effective dose is delivered to attain a serum concentration of GM-CSF antagonist at about 1,500 ng/mL. In some embodiments, the therapeutically effective dose is delivered to attain a serum concentration of GM-CSF antagonist at about 2,000 ng/mL. In some embodiments, the therapeutically effective dose is delivered to attain a serum concentration of GM-CSF antagonist at about 2,500 ng/mL. In some embodiments, the therapeutically effective dose is delivered to attain a serum concentration of GM-CSF antagonist at about 3,000 ng/mL. In some embodiments, the therapeutically effective dose is delivered to attain a serum concentration of GM-CSF antagonist at about 3,400 ng/mL. In some embodiments, the therapeutically effective dose is delivered to attain a serum concentration of GM-CSF antagonist at about 4,000 ng/mL. In some embodiments, the therapeutically effective dose is delivered to attain a serum concentration of GM-CSF antagonist at about 4,500 ng/mL. In some embodiments, the therapeutically effective dose is delivered to attain a serum concentration of GM-CSF antagonist at about 5,000 ng/mL. In some embodiments, the therapeutically effective dose is delivered to attain a serum concentration of GM-CSF antagonist at about 5,000 ng/mL. In some embodiments, the therapeutically effective dose is delivered to attain a serum concentration of GM-CSF antagonist at about 5,000 ng/mL. In some embodiments, the therapeutically effective dose is delivered to attain a serum concentration of GM-CSF antagonist at about 5,500 ng/mL. In some embodiments, the therapeutically effective dose is delivered to attain a serum concentration of GM-CSF antagonist at about 6,000 ng/mL. In some embodiments, the therapeutically effective dose is delivered to attain a serum concentration of GM-CSF antagonist at about 6,500 ng/mL. In some embodiments, the therapeutically effective dose is delivered to attain a serum concentration of GM-CSF antagonist at about 7,000 ng/mL. In some embodiments, the therapeutically effective dose is delivered to attain a serum concentration of GM-CSF antagonist at about 7,500 ng/mL. In some embodiments, the therapeutically effective dose is delivered to attain a serum concentration of GM-CSF antagonist at about 8,000 ng/mL. In some embodiments, the therapeutically effective dose is delivered to attain a serum concentration of GM-CSF antagonist at about 8,300 ng/mL. In some embodiments, the therapeutically effective dose is delivered to attain a serum concentration of GM-CSF antagonist at about 8,500 ng/mL. In some embodiments, the therapeutically effective dose is delivered to attain a serum concentration of GM-CSF antagonist at about 9,000 ng/mL. In some embodiments, the therapeutically effective dose is delivered to attain a serum concentration of GM-CSF antagonist at about 9,500 ng/mL. In some embodiments, the therapeutically effective dose is delivered to attain a serum concentration of GM-CSF antagonist at about 10,000 ng/mL. In some embodiments, the therapeutically effective dose is delivered to maintain a serum concentration of GM-CSF antagonist as recited above for about 1 day, 3 days, 4, days, 5 days, 6 days, 7 days, 8 days, 9 days, 10 days, 11 days, 12 days, 13 days, 1 week, 2 weeks, 3 weeks, 5 weeks, 6 weeks 7 weeks, 8 weeks, 9 weeks, 10 weeks, 11 weeks, 12 weeks, 13 weeks, 14 weeks, 1 month, 2 months, or up to 3 months.

In one aspect, a single administration of the GM-CSF antagonist is administered to the subject. In another embodiment, a single administration of the GM-CSF antagonist is sufficient to improve, stabilize or reduce one or more symptoms of CRS. In one embodiment the one or more symptoms of CRS is not a result of administering an immunotherapy (e.g., adoptive cell transfer, administration of monoclonal antibodies, administration of a cancer vaccine, T cell engaging therapies, or any combination thereof) to the subject. In another embodiment, the single administration of the GM-CSF antagonist is sufficient to improve, stabilize or reduce one or more symptoms of CRS associated with an infection. In some embodiments, a single administration of the GM-CSF antagonist is sufficient to improve, stabilize or reduce one or more symptoms for longer than seven days. For example, in some embodiments, a single administration of the GM-CSF antagonist is sufficient to improve, stabilize or reduce one or more symptoms for about 8 days, 9 days, 10 days, 11 days, 12 days, 13 days, or 14 days. In some embodiments, a single administration of the GM-CSF antagonist is sufficient to improve, stabilize or reduce one or more symptoms for greater than 14 days.

In some embodiments, the single administration of the GM-CSF antagonist is sufficient to improve, stabilize or reduce one or more symptoms for longer than twenty days. For example, in some embodiments, the single administration of the GM-CSF antagonist is sufficient to improve, stabilize or reduce one or more symptoms for about 21 days, 22 days, 23 days, 24 days, 25 days, 26 days, 27 days, 28 days, 29 days, 30 days, 31 days, 32 days, 33 days, 34 days, or 35 days. In some embodiments, the single administration of the GM-CSF antagonist is sufficient to improve, stabilize or reduce one or more symptoms for greater than 35 days.

In some embodiments, the administration interval is once every week.

In some embodiments, the administration interval is at least five days.

In some embodiments, the administration interval is once every two weeks.

In some embodiments, the administration interval is once every three weeks.

In some embodiments, the administration interval is once every four weeks.

In some embodiments, the administration interval is once every five weeks.

In some embodiments, a repeat dose is administered to the subject if one of more symptoms do not improve, stabilize or reduce one or more symptoms within 24 hours, 2 days, 3 days, 4 days, 5 days, 6 days, 7 days, 8 days, 9 days, 10 days. Accordingly, in some embodiments, a repeat dose is administered to the subject if one or more symptoms do not improve, stabilize or reduce one or more symptoms within 24 hours. In some embodiments, a repeat dose is administered to the subject if one or more symptoms do not improve, stabilize or reduce one or more symptoms after 24 hours. In some embodiments, a repeat dose is administered to the subject if one or more symptoms do not improve, stabilize or reduce one or more symptoms within 3 days. In some embodiments, a repeat dose is administered to the subject if one or more symptoms do not improve, stabilize or reduce one or more symptoms within 4 days. In some embodiments, a repeat dose is administered to the subject if one or more symptoms do not improve, stabilize or reduce one or more symptoms within 7 days.

In some embodiments, the repeat dose is same as the initial dose.

In some embodiments, the repeat dose is different from the initial dose. For example, in some embodiments, the repeat dose is greater than the initial dose. In some embodiments, the repeat dose is less than the initial dose.

In some embodiments, the repeat dose is between 0.5 mg/kg and 3 mg/kg. In some embodiments, the repeat dose is about 0.5 mg/kg. In some embodiments, the repeat dose is about 1.0 mg/kg. In some embodiments, the repeat dose is about 1.5 mg/kg. In some embodiments, the repeat dose is about 2.0 mg/kg. In some embodiments, the repeat dose is about 2.5 mg/kg. In some embodiments, the repeat dose is about 3.0 mg/kg. In some embodiments, the therapeutically effective dose is between 3 mg/kg and 10 mg/kg. In some embodiments, the therapeutically effective dose is between 5 mg/kg and 10 mg/kg. In some embodiments, the therapeutically effective dose is about 3 mg/kg. In some embodiments, the therapeutically effective dose is about 4 mg/kg. In some embodiments, the therapeutically effective dose is about 5 mg/kg. In some embodiments, the therapeutically effective dose is about 6 mg/kg. In some embodiments, the therapeutically effective dose is about 7 mg/kg. In some embodiments, the therapeutically effective dose is about 8 mg/kg. In some embodiments, the therapeutically effective dose is about 9 mg/kg. In some embodiments, the therapeutically effective dose is about 10 mg/kg.

In some embodiments, the GM-CSF antagonist is a GM-CSF antibody or fragment thereof.

In some embodiments, the GM-CSF antibody is lenzilumab or TJM2.

In some embodiments, the GM-CSF antagonist is a GM-CSF receptor alpha (GM-CSFRα) antagonist.

In some embodiments, the GM-CSFRα antagonist binds to a Tyr-Leu-Asp-Phe-Gln motif at position 226 to 330 of human GM-CSFRα.

In some embodiments, the GM-CSFRα antagonist is a GM-CSFRα antibody or fragment thereof.

In some embodiments, the GM-CSFRα antagonist is a GM-CSFRα antibody or fragment thereof that competes with an anti-GM-CSFRα antibody defined by a heavy chain variable domain of SEQ ID NO: 1 and a light chain variable domain of SEQ ID NO: 2.

In some embodiments, the GM-CSFRα antibody is human or humanized IgG4 antibody.

In some embodiments, the GM-CSFRα antibody is mavrilimumab.

In some embodiments, the anti-GM-CSFRα antibody or a fragment thereof comprises a light chain complementary-determining region 1 (LCDR1) defined by SEQ ID NO: 6, a light chain complementary-determining region 2 (LCDR2) defined by SEQ ID NO: 7, and a light chain complementary-determining region 3 (LCDR3) defined by SEQ ID NO: 8; and a heavy chain complementary-determining region 1 (HCDR1) defined by SEQ ID NO: 3, a heavy chain complementary-determining region 2 (HCDR2) defined by SEQ ID NO: 4, and a heavy chain complementary-determining region 3 (HCDR3) defined by SEQ ID NO: 5.

In some embodiments, the method further comprises a step of administering an antiviral drug.

In some embodiments, the antiviral drug is Remdesivir, Chloroquine (e.g., hydroxycholorquine), Lopinavir and ritonavir, APN01, Favilavir, or Baricitinib. Accordingly, in some embodiments, the antiviral drug is Remdesivir. In some embodiments, the antiviral drug is Chloroquine (e.g., hydroxycholorquine). In some embodiments, the antiviral drug is Lopinavir. In some embodiments, the ritonavir. In some embodiments, the antiviral drug is Lopinavir and ritonavir. In some embodiments, the antiviral drug is APN01. In some embodiments, the antiviral drug is Favilavir. In some embodiments, the antiviral drug is Baricitinib.

In some embodiments, the subject is not intubated. In some embodiments, the subject is not connected to a respirator or mechanical ventilation.

In some embodiments, the administering the GM-CSF antagonist results in discharge from the hospital and/or weaning off from on-going medical care within 12 days. In some embodiments, the administering the GM-CSF antagonist results in discharge from the hospital and/or weaning off from on-going medical care within 10 days. In some embodiments, the administering the GM-CSF antagonist results in discharge from the hospital and/or weaning off from on-going medical care within 8 days. In some embodiments, the administering the GM-CSF antagonist results in discharge from the hospital and/or weaning off from on-going medical care within 7 days. In some embodiments, the administering the GM-CSF antagonist results in discharge from the hospital and/or weaning off from on-going medical care within 6 days. In some embodiments, the administering the GM-CSF antagonist results in discharge from the hospital and/or weaning off from on-going medical care within 5 days. In some embodiments, the administering the GM-CSF antagonist results in discharge from the hospital and/or weaning off from on-going medical care within 4 days. In some embodiments, the administering the GM-CSF antagonist results in discharge from the hospital and/or weaning off from on-going medical care within 3 days. In some embodiments, the administering the GM-CSF antagonist results in discharge from the hospital and/or weaning off from on-going medical care within 2 days. In some embodiments, the administering the GM-CSF antagonist results in discharge from the hospital and/or weaning off from on-going medical care within 1 days.

In some embodiments, the administering the GM-CSF antagonist results in resolution of fever within 7 days. In some embodiments, the administering the GM-CSF antagonist results in resolution of fever within 5 days. In some embodiments, the administering the GM-CSF antagonist results in resolution of fever within 4 days. In some embodiments, the administering the GM-CSF antagonist results in resolution of fever within 3 days. In some embodiments, the administering the GM-CSF antagonist results in resolution of fever within 2 days. In some embodiments, the administering the GM-CSF antagonist results in resolution of fever within 1 day.

In some embodiments, the subject is administered an antiviral drug.

In some embodiments, the antiviral drug is hydroxychloroquine, corticosteroids, or combinations thereof.

BRIEF DESCRIPTION OF THE DRAWING

The drawings are for illustration purposes only, not for limitation.

FIG. 12 panel A is a baseline lung CT scan of Patient 1, showing presence of bilateral, blurred ground glass opacities with crazy paving pattern and small dense consolidation areas; patient febrile, receiving O2 through a facemask, FiO2 0.4, PAO2 86 mmHg, LDH 374 U/L, CRP 100 mg/L.

FIG. 12 panel B is CT scan of Patient 1 at discharge, 7 days later, showing significant reduction and regression of these findings; afebrile, on room air, SpO2 98%, CRP 12.5 mg/L, LDH normalized. FIG. 12 panel C is a baseline lung CT scan of Patient 2, showing extensive involvement of right lung with posterior large consolidation area and air bronchogram; ground glass opacities and crazy paving pattern predominant on the left side; patient febrile, receiving high-low O2 through a facemask with reservoir bag+12 hours/day of CPAP, PAO2 176 mmHg, LDH 944 U/L, CRP 177 mg/L. FIG. 12 panel D is a CT scan of Patient 2 at discharge, 14 days later, showing significant improvement in lung involvement; patient afebrile, on room air, SpO2 98%, CRP 28.2 mg/L, LDH normalized.

DEFINITIONS

Figure 1:
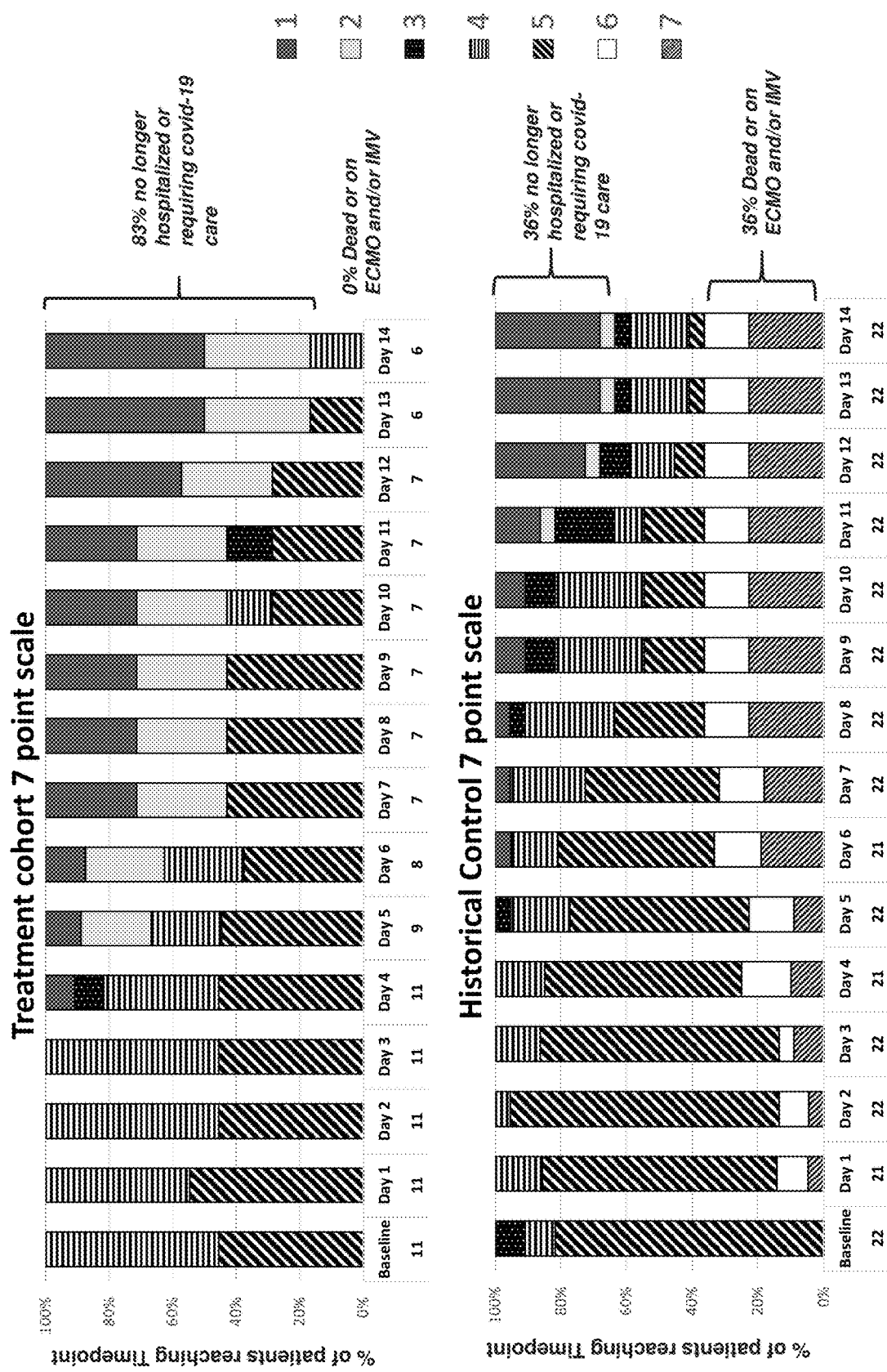
FIG. 1 is an exemplary bar graph illustrating the seven point scale over time for all patients in all categories. The top panel shows progression over time for the treated cohort, and the bottom panel shows progression over time for the historical control group. The seven point scale is: 1. Patient discharged from the hospital; 2. Hospitalized, not requiring supplemental oxygen, no longer requiring ongoing medical care for COVID-19; 3. Hospitalization, not requiring supplemental oxygen, requiring ongoing medical care (COVID-19 related or otherwise); 4. Hospitalization requiring supplemental low-flow oxygen therapy (O2 concentration 35% or below); 5. Hospitalization, requiring nasal high-flow oxygen therapy ($O_2$ concentration 40% or above), non-invasive mechanical ventilation, or both; 6. Hospitalization requiring invasive mechanical ventilation; 7. Death. For patients who were no longer hospitalized or requiring on-going medical care (score 1 or 2), last known score was carried forward assuming they will not be re-hospitalized. For patients who were scored 6 or 7, last known score was carried forward as patient had already died and/or progressed to invasive mechanical ventilation. 83% of the treated group was no longer hospitalized or required COVID-19 care and 0% of the patient died or required ECMO and/or IMV at day 14. For historical control group, 36% was no longer hospitalized required COVID-19 care, and 36% of the patients died or was on ECMO and/or IMV at day 14.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Antibody: As used herein, the term "antibody" refers to immunoglobulin molecules and immunologically active portions of immunoglobulin (Ig) molecules, i.e., molecules that contain an antigen binding site that binds (immunoreacts with) an antigen. By "binds" or "immunoreacts with" is meant that the antibody reacts with one or more antigenic determinants of the desired. Antibodies include, antibody fragments. Antibodies also include, but are not limited to, polyclonal, monoclonal, chimeric dAb (domain antibody), single chain, Fab, Fab', F(ab')2 fragments, scFvs, and Fab expression libraries. An antibody may be a whole antibody, or immunoglobulin, or an antibody fragment.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery.

Improve, increase, inhibit or reduce: As used herein, the terms "improve," "increase" "inhibit" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein, e.g., a subject who is administered a placebo. A "control subject" is a subject afflicted with the same form of disease as the subject being treated, who is about the same age as the subject being treated.

"Inhibition" or "inhibiting": As used herein "inhibition" or "inhibiting," or grammatical equivalents, means reduction, decrease or inhibition of biological activity. Neutralization: As used herein, neutralization means reduction or inhibition of biological activity of the protein to which the neutralizing antibody binds, in this case GM-CSFRα, e.g. reduction or inhibition of GM-CSF binding to GM-CSFRα, or of signaling by GM-CSFRα e.g. as measured by GM-CSFRα-mediated responses. The reduction or inhibition in biological activity may be partial or total. The degree to which an antibody neutralizes GM-CSFRα is referred to as its neutralizing potency.

Patient: As used herein, the term "patient" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLAS TN for nucleotide sequences and BLASTP, gapped BLAST, and PSI-BLAST for amino acid sequences. Exemplary such programs are described in Altschul, et al., Basic local alignment search tool, *J Mal. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. In some embodiments, the "therapeutically effective amount" is sufficient to prevent progression of a disease condition, an onset of one or more symptoms or complications associated with the condition, or a significant increase or a significant decrease in the level of one or more biomarkers associated with the condition from its normal level. For example, the "therapeutically effective amount" is sufficient to prevent progression of symptoms or complications associated with viral infection, such as, to prevent progression to non-invasive ventilation or mechanical ventilation. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease. In some embodiments, the term "treating" or its grammatically equivalents refers to preventing a disease condition, an onset of one or more symptoms associated with the condition, or a significant increase or a significant decrease in the level of one or more biomarkers associated with the condition from its normal level. For example, treating a patient infected with a virus (e.g., COVID-19) includes prevention of progression of symptoms or complications associated with viral infection, such as, prevention of progression to non-invasive ventilation or mechanical ventilation.

DETAILED DESCRIPTION

The present invention provides, among other things, method of treating cancer by inhibiting immunosuppressive activity of myeloid-derived suppressor cells (MDSCs) in a patient in need of treatment using a GM-CSF antagonist. In some embodiments, a GM-CSF antagonist is used in combination with an immune checkpoint inhibitor. It is contemplated that the present invention is particularly effective in treating immune checkpoint inhibitory (ICI) refractory or resistant cancers, or late stage or metastatic cancers.

Various aspects of the invention are described in detail in the following sections. The use of sections is not meant to limit the invention. Each section can apply to any aspect of the invention. In this application, the use of "or" means "and/or" unless stated otherwise.

Coronavirus Infection

Coronaviruses (CoVs) are enveloped viruses with a positive-strand RNA genome, which primarily target respiratory and intestinal mucosal surfaces to establish respiratory and enteric infections. Their name derives from their crown-like appearance in electron micrographs.

Coronaviruses such as the human CoV isolates 229E and OC43 cause mild and self-limiting infections of the respiratory tract such as the common cold. Novel isolates HCoV-NL63 and HCoV-HKU1 have also been associated with common cold.

Some novel emerging coronaviruses have resulted in serious global outbreaks such as SARS in 2003, MERS in 2012 and COVID-19 in 2019. These diseases are associated with acute and often severe respiratory complications, especially in elderly and immunocompromised individuals.

COVID-19 infection results in respiratory symptoms like a runny nose, headache, dry cough, sore throat, shortness of breath, fever and fatigue. Symptoms of COVID-19 may appear 2-14 days after exposure. Older adults and those with underlying health conditions and weakened immune systems may be at risk for more severe symptoms.

Once COVID-19 enters the human respiratory tract, it infects and propagates in cells lining the airway, causing damage that triggers local inflammation, recruiting immune cells in the vicinity to eradicate the virus. The immune response then recedes, and patients recover from mild disease. In elderly and other vulnerable individuals, there is instead an uncontrolled immune response, triggering an overproduction of immune cells and signaling molecules, leading to a cytokine storm often associated with a flood of immune cells into the lung. If an infection progresses to something more severe, it can cause bronchitis, pneumonia, kidney failure and even death.

Pneumonia associated with COVID-19 usually has bilateral lung involvement. Pneumonia is characterized by inflammation of the alveoli or air sacs, which may fill with fluid or pus (purulent material), causing cough with phlegm or pus, fever, chills, and difficulty breathing. Pneumonia may cause pleural effusion, i.e. fluid accumulation in the thin space between layers of tissue that line the lungs and chest cavity (pleura), which may lead to pus accumulation, infection and lung abscess. In severe cases, lung fibrosis may occur. Pulmonary fibrosis occurs when the lung tissue around and between the alveoli becomes thickened, damaged and scarred, making it more difficult for oxygen to pass into the bloodstream. This is accompanied by fibroblast proliferation and an increase in matrix proteins, abnormal alveolar structure leading to loss of lung function and severe respiratory failure. Some individuals may experience a rapid worsening of their symptoms (acute exacerbation), such as severe shortness of breath, that may last for several days to weeks. Individuals with acute exacerbations may be placed on a mechanical ventilator. Pulmonary fibrosis is usually irreversible and is managed by corticosteroid therapy, but could potentially be fatal.

Acute respiratory distress syndrome (ARDS), also known as Acute Lung Injury and Noncardiac Pulmonary Edema, is the most severe form of acute lung injury (ALI), is a devastating clinical syndrome with high mortality rate (30-60%). ARDS is characterized by breakdown of the alveolar-capillary barrier, leading to flooding of the alveolar space. Predisposing factors for ARDS are diverse and include sepsis, aspiration, and pneumonias including infections with coronavirus, H1N1 and H5N1 avian influenza virus. Several other pathogens including Spanish flu virus and anthrax can results in ARDS. To date, no effective cure exists for ARDS.

SARS-CoV and COVID-19 rapidly spread person-to-person through respiratory secretions. Upon exposure of the host to the virus, the viral Spike protein (which projects through the viral envelope forming the characteristic spikes in the coronavirus), binds to epithelial cells expressing virus entry receptors, of which the angiotensin-converting enzyme 2 (ACE2) is one of the main receptors. In the respiratory tract, ACE2 is widely expressed on epithelial cells of alveoli, trachea, bronchi, bronchial serous glands, and alveolar monocytes and macrophages. The virus enters and replicates in these target cells, releasing mature virions which infect new target cells. Atypical pneumonia with rapid respiratory deterioration and lung injury can result due to increased levels of activated proinflammatory chemokines and cytokines.

Other pathogens including the influenza H5N1 and H1N1 viruses and RSV employ the ACE2 receptor for entry and the angiotensin-renin system plays a role in host response to infection.

Cytokine Release Syndrome (Cytokine Storm)

Cytokine release syndrome (CRS), (also known as cytokine storm and hypercytokinemia, is a significant immune response to pathogens that invade the body. The precise causation of cytokine storms within the body has not been definitively established. A possible causation of cytokine storms is an encounter, by the immune system, of a new and highly pathogenic pathogen. Cytokine storms are also associated with a number of infectious and non-infectious diseases, including influenza, adult respiratory distress syndrome (ARDS), and systemic inflammatory response syndrome (SIRS). Cytokine storm has also been suggested to be an overreaction of the immune system which is considered a major factor behind catastrophic organ failure and death in some coronavirus patients During a cytokine storm, inflammatory mediators, for example pro-inflammatory cytokines such as Interleukin-1 (IL1), Interleukin-6 (IL6), tumor necrosis factor-alpha (TNF-alpha), oxygen free radicals, and coagulation factors are released by the immune cells of the body. Cytokine storms have the potential to cause significant damage to body tissues and organs. For example, occurrence of cytokine storms in the lungs can cause an accumulation of fluids and immune cells, for example macrophages, in the lungs, and eventually block off the body's airways thereby resulting in respiratory distress and even death.

Study demonstrated that in the pathogenesis of SARS, a cytokine storm occurred, involving a considerable release of proinflammatory cytokine including interleukins (IL)-6, tumour necrosis factor α (TNF-α), and IL-12. In the research of Middle East respiratory syndrome, caused by another coronavirus (MERS-CoV), cytokine genes of IL-6, IL-1β, and IL-8 can be markedly high. A delayed proinflammatory cytokine induction by MERS-CoV was also confirmed. Similar to the changes in SARS and MERS, in COVID-19, higher plasma levels of cytokines including IL-6, IL-2, IL-7, IL-10, granulocyte-colony stimulating factor (G-CSF), interferon-γ-inducible protein (IP10), monocyte chemoattractant protein (MCP1), macrophage inflammatory protein 1 alpha (MIP1A), and TNF-α were found in ICU patients, which implied a cytokine storm occurred and related to the severity and prognosis of the disease. In the biopsy samples at autopsy from a patient who died from the severe infection with COVID-19, histological examination showed bilateral diffuse alveolar damage with cellular fibromyxoid exudates. Mononuclear inflammatory lymphocytes were seen in both lungs. These studies suggested that an inflammatory factor or a cytokine storm have occurred. In another research, after analyzing the immune characteristics of patients with COVID-19, it was found that aberrant pathogenic T cells and inflammatory monocytes are rapidly activated and then producing a large number of cytokines and inducing an inflammatory storm. Among them, GM-CSF and IL-6 are the key cytokines leading to inflammatory storm which may result in increased alveolar-capillary blood-gas exchange dysfunction, especially impaired oxygen diffusion, and eventually lead to pulmonary fibrosis and organ failure.

Causes of Cytokine Release Syndrome

Coordination between innate and adaptive immunity against pathogens is indispensable in higher organisms including humans. In particular, innate immunity plays a critical role during primary infection with various bacteria and viruses. The specific recognition of microorganisms may represent the basis of innate immunity. Specific recognition systems have gradually been clarified and the common platforms are Toll-like receptors (TLRs), the NLR family (nucleotide-binding oligomerization domain-like receptors), and the RLR family [RIG (retinoic acid-inducible gene)-I-like receptors]. These molecules are called pattern recognition receptors (PRRs). PRRs can recognize lipopolysaccharides (LPS), viral antigens, and bacterial/viral genomes, leading to the activation of intrinsic signaling pathways (e.g., myeloid differentiation factor 88; MyD88) and the production of various cytokines. The production of such cytokines may activate leukocytes and eliminate the infective agents. In one embodiment, the organ dysfunction or failure that occurs as a result of the CRS-induced hyperinflammation that is not in direct response to the infectious insult itself, but is a consequence of the subject's immune response (e.g., ARDS in patients with pancreatitis). The symptoms of CRS include hypotension as well as high fever and can progress to an uncontrolled systemic inflammatory response with vasopressor-requiring circulatory shock, vascular leakage, disseminated intravascular coagulation, and multi-organ system failure. Laboratory abnormalities that are common in patients with CRS include cytopenias, hypertriglyceridemia, elevated creatinine, ferritin, and liver enzymes, deranged coagulation parameters, and elevated levels of CRP. Mild cases of CRS can present as flu-like symptoms, where more severe cases can show signs of life-threatening cardiovascular, pulmonary and renal involvement. Patients with severe CRS can develop renal failure or signs of cardiac dysfunction with reduced ejection fraction on ultrasound. In addition, patients with severe CRS frequently display vascular leakage with peripheral and pulmonary edema. Neurotoxicity can occur concurrent or with delay. Patients with CRS can also develop respiratory symptoms and can lead to life-threatening pneumonia and respiratory failure. Cytokine release syndromes can lead to hyperinflammation of lung tissue due to infection. In some embodiments, the infection is a viral infection, a bacterial infection, a fungal infection, or other infections driving hyperinflammation of the lung. Mild cases of CRS may display cough and tachypnea, but can progress to ARDS with dyspnea, hypoxemia, and bilateral opacities on chest X-ray. GM-CSF is present at high concentrations with the alveoli of patients with ARDS. Additionally, plasma of patients with ARDS inhibits PMN apoptosis through GM-CSFR. In some embodiments, CRS is associated with graft-versus-host disease (GVHD), pancreatitis, or acute kidney injury.

CRS can also lead to a life-threatening pneumonia and respiratory failure. GM-CSF strongly activates macrophages and is considered to be a proinflammatory cytokine. GM-CSF production is associated with tissue inflammation. GM-CSF-derived signals are critically involved in the differentiation of macrophages and in the proliferation and activation of other immune cells. GM-CSF-activated macrophages produce proinflammatory cytokines, including tumor necrosis factor (TNF), IL-1β, IL-6, IL-23 and IL-12. In addition, GM-CSF receptor activation triggers stimulation of multiple downstream signaling pathways, including Janus kinase 2 (JAK2)/signal transducer and activator of transcription 5 (STAT5), the mitogen-activated protein kinase (MAPK) pathway, and the phosphoinositide 3 kinase (PI3K) pathway, all relevant in activation and differentiation of myeloid cells. Under physiologic conditions, levels of circulating GM-CSF are low, but levels are elevated in inflammatory conditions. Several cell types can serve as a source of GM-CSF, including fibroblasts, endothelial cells, macrophages, dendritic cells, T cells, neutrophils, eosinophils, and cancer cells, with most production occurring locally at the site of inflammation. This in turn exacerbates the inflammatory reaction via cytokine pathways that have been termed the colony stimulating factor network. GM-CSF can be induced by inflammatory cytokines and in turn amplifies production of pro-inflammatory cytokines, thus functioning as a feed-forward inflammatory amplifier. GM-CSF signals through the GM-CSF receptor (GMCSF-R), which consists of a specific ligand-binding α-chain (GMCSF-Rα) and a signal-transducing β-chain (GMCSF-Rβ) that is common to IL-3 and IL-5 receptors. Hence, GMCSF-R signaling can be specifically targeted with antibodies directed at GM-CSF-Rα.

Acute Respiratory Distress Syndrome (ARDS)

Acute respiratory distress syndrome (ARDS) occurs when fluid builds up in the tiny, elastic air sacs (alveoli) in your lungs. The fluid keeps your lungs from filling with enough air, which means less oxygen reaches your bloodstream. This deprives your organs of the oxygen they need to function. The signs and symptoms of ARDS can vary in intensity, depending on its cause and severity, as well as the presence of underlying heart or lung disease. They include severe shortness of breath, labored and unusually rapid breathing, low blood pressure and confusion and extreme tiredness. As a result of the respiratory symptoms, the patients often require supplemental oxygen, and in severe cases require mechanical ventilation.

Acute respiratory distress syndrome (ARDS) is caused by infectious insults, such as a non-pulmonary infection (e.g., pancreatitis) or a pulmonary infection (e.g., pneumonia), or caused by noninfectious events, such as trauma or toxic exposure. Clinical and histopathologic characteristics are similar across severely affected patients, suggesting that a common mode of immune reaction may be involved in the immunopathogenesis of ARDS. There may be etiologic substances that have an affinity for respiratory cells and induce lung cell injury in cases of ARDS. These substances originate not only from pathogens, but also from injured host cells. Immune cells and immune proteins may recognize and act on these substances, including pathogenic proteins and peptides, depending upon the size and biochemical properties of the substances (this theory is known as the protein-homeostasis-system hypothesis). The severity or chronicity of ARDS depends on the amount of etiologic substances with corresponding immune reactions, the duration of the appearance of specific immune cells, or the repertoire of specific immune cells that control the substances. Therefore, treatment with early systemic immune modulators as soon as possible may reduce aberrant immune responses in the potential stage of ARDS.

Inflammatory insults, either locally from the lungs or systemically from extra-pulmonary sites, affect bronchial epithelium, alveolar macrophages, and vascular endothelium. TLR signaling pathways appear to play a major role in initiation of the signaling cascade in ARDS. Resident alveolar macrophages secrete pro-inflammatory cytokines, leading to neutrophil and monocyte or macrophage recruitment, as well as activation of alveolar epithelial cells and effector T cells, to promote and sustain inflammation and tissue injury. Hyperactivation of myeloid cells and T-cells produce large amounts of inflammatory cytokines, which in turn lead to endothelial activation and microvascular injury, ultimately leading to barrier disruption in ARDS, which can be worsened by mechanical stretch. Extensive damage to lung epithelia and endothelia results in an impaired alveolar-capillary barrier. Disruption of this barrier allows protein-rich fluid to enter the alveoli causing fluid accumulation in alveolar spaces (pulmonary edema) interfering with gas exchange.

Causes of Acute Respiratory Distress Syndrome

The mechanical cause of ARDS is fluid leaked from the smallest blood vessels in the lungs into the tiny air sacs where blood is oxygenated. Normally, a protective membrane keeps this fluid in the vessels. Severe illness or injury, however, can cause damage to the membrane, leading to the fluid leakage of ARDS. Typically, the most common underlying causes of ARDS include (i) severe non-thoracic trauma (head, chest or other major injury. Accidents, such as falls or car crashes can directly damage the lungs or the portion of the brain that controls breathing; massive blood transfusions and burns); (ii) post thoracic surgery; (iii) aspiration/toxic exposure (breathing high concentrations of smoke or chemical fumes can results in ARDS, as can inhaling (aspirating) commit or near-drowning episodes); (iv) non-pulmonary infections (a serious and widespread infections of the bloodstream with sources that include the peritoneum, urinary tract soft tissue and skin); (v) pulmonary infections (severe pneumonia, bacterial, fungal, and viral infections). Typically, 90% of ARDS is caused by an infectious agent.

In some embodiments, an infection is caused by bacteria. In some embodiments, bacteria is *Streptococcus pneumoniae, Haemophilus influenzae, Enterobacteriaceae, Staphylococcus aureus* (e.g., methicillin-resistant *Staphylococcus aureus*), *Legionella pneumophila, Clamydia pneumomae, Mycoplasma pneumoniae, Pseudomonas aeruginosa, Acinetobacter baumannii, Stenotrophompnas maltophilia*.

In some embodiments, an infection is caused by a virus. In some embodiments, a virus is an influenza A, an influenza B, a Rhinoviruses, a RSV, a Parainfluenza virus, a Coronavirus, an Enterovirus, a HSV, or a CMV.

In some embodiments, an infection is caused by fungi. In some embodiments, fungi is *Pneumocystis* (e.g., *Pneumocystis Jirovecii* and *Pneumocystis carinii*), *Aspergillus* (e.g., *Aspergillus fumigatus, Aspergillus flavus, Aspergillus niger, Aspergillus nidulans* and *Aspergillus terreus*), *Histoplasma capsulatum, Coccidioides immitis, Blastomyces dermatitidis, Paracoccidioides brasiliensis, Sporothrix schenckii* or *Cryptococcus neoformans*. In some embodiments the infection is pneumocystis pneumonia. In some embodiments the infection is aspergillosis. In some embodiments, an infection is caused by a parasite. In some embodiments, a parasite is *Toxoplasma gondii*.

Coronavirus, Influenza Viruses, Rhinovirus

Coronaviruses (CoVs) are a family of single-stranded RNA viruses. CoVs have been demonstrated to cross species barriers and can cause illness in human ranging in degrees of severity. Coronavirus infection, as used herein, means an infection, including a patient being infected, with any coronavirus virus including coronavirus COVID-19, HCoV-NL63, HCoV-OC43, HCoV-229E, HCoV-HKU1, SARS-CoV (Severe Acute Respiratory Syndrome-Corona Virus), and CoV MERS (Middle East Respiratory Syndrome virus, previously called "EMC").

Coronaviruses cause approximately 10-15% of all upper and lower respiratory tract infections. They account for significant hospitalizations of children under 18 years of age, the elderly and immunocompromised individuals. According to a number of international studies 5-10% of the acute respiratory diseases are caused by HCoV-NL63. These numbers are probably an underestimation since during diagnostic screening for respiratory viruses tests for HCoV's are frequently not included. Another aspect HCoV-NL63 infection is the co-infection with other human coronaviruses, influenza A, respiratory syncytial virus (RSV), parainfluenza virus human metapneumovirus. In children they are associated with acute respiratory tract illness, pneumonia and Croup leading in many cases to hospitalization.

Influenza viruses are divided into three types, type A, B and C, based upon differences in internal antigenic proteins. The Influenza A virus may be further classified into various subtypes according to the different HA and NA viral proteins displayed on the surface of the virus. Each subtype of virus can mutate into a variety of strains with differing pathogenic profiles. Currently, there are 16 known HA antigen subtypes (H1 to H16) and 9 known NA antigen subtypes (N1 to N9). Influenza A viruses can infect humans, birds, pigs, horses, and other animals. A subset of Influenza A virus subtypes, including but not limited to, H1N1, H2N2, H3N2, H5N1, H7N7, H1N2, H9N2, H7N2, H7N3, and H10N7 subtypes, have been confirmed to infect humans. All combinations of the 16 HA and 9 NA subtypes have been identified in avian species. In addition, Influenza B virus and Influenza C virus can also infect humans.

Due to viral recombination, prior immunity to one strain does not necessarily confer protection to the next. Upon infection, a new virus replicates unchecked, while the host mounts a highly inflammatory primary immune response. An influenza infection produces an acute set of symptoms including headache, cough, sore throat, rhinitis, fever and general malaise. In severe cases or situations involving pre-existing pulmonary or cardiovascular disease, hospitalization is required. Pneumonia due to direct viral infection or due to secondary bacterial or viral invasion is the most frequent complication.

The outcome of influenza infection is dependent on both the virus and the host. The genetic makeup of the HA and NA genes confers virulence. For example, introduction of HA and NA genes from pandemic H5N1 strains to a relatively mild virus transforms the virus into a highly virulent strain in mice. During replication, Influenza virus utilizes host protein production machinery and as a result, causes death of the infected cell (cytopathology). Such respiratory epithelial cell destruction produces an array of signals initiating an inflammatory reaction (cytokine cascade) that promotes the recruitment of inflammatory cells (e.g., neutrophils and CD4+/CD8+ T cells) to the delicate surface of the lung, leading to consolidation of air spaces and a decline in arterial oxygen saturation. In eliminating the virus, the host response causes further respiratory cell death, and the responding inflammatory cells (e.g., T cells) produce an additional battery of inflammatory mediators (e.g., TNF$\alpha$ and IFN$\gamma$), which in excess lead to a cytokine storm, causing capillary leak and resulting in pulmonary edema and leukocyte transudation into the airspaces, thereby initiating the acute respiratory distress syndrome (ARDS). More chronic symptoms of disease, such as cachexia, fever and appetite suppression, are directly linked to the concentration of systemic mediators/cytokines that accumulate. Therefore, the whole cascade is initiated by virus-induced cytopathology, but mortality is ultimately determined by the magnitude of the inflammation that results from the immune response. Both the viral-induced cytopathology and the host inflammatory response can predispose the infected subject to secondary bacterial infection, further increasing morbidity and mortality.

Rhinoviruses is one of the most common causative agent in humans for the common cold. Rhinoviruses belong to the Enterovirus genus in the family Picornaviridae. There are three species of rhinovirus (A, B, and C) which include approximately 160 recognized types of human rhinovirus that differ according to the virus's surface proteins. The species of rhinovirus have been associated with the severity of the infection caused by the virus. For example, rhinovirus C appear to cause more severe infections that rhinoviruses A and B. The mode of transmission for rhinoviruses are predominately via aerosols of respiratory droplets and from virus-contaminated surfaces.

GM-CSF Antagonists

GM-CSF Signaling

GM-CSF is a type I proinflammatory cytokine which enhances survival and proliferation of a broad range of hematopoietic cell types. It is a growth factor first identified as an inducer of differentiation and proliferation of myeloid cells (e.g., neutrophils, basophils, eosinophils, monocytes, and macrophages) (Wicks I P and Roberts A W. Nat Rev Rheumatol. 2016, 12(1):37-48). Studies using different approaches have demonstrated that with GM-CSF overexpression, pathological changes almost always follow (Hamilton J A et al., Growth Factors. 2004, 22(4):225-31). GM-CSF enhances trafficking of myeloid cells through activated endothelium of blood vessels and can also contribute to monocyte and macrophage accumulation in blood vessels during inflammation. GM-CSF also promotes activation, differentiation, survival, and proliferation of monocytes and macrophages as well as resident tissue macrophages in inflamed tissues. It regulates the phenotype of antigen-presenting cells in inflamed tissues by promoting the differentiation of infiltrating monocytes into M1 macrophages and monocyte-derived dendritic cells (MoDCs). Moreover, the production of IL-23 by macrophages and MoDCs, in combination with other cytokines such as IL-6 and IL-1, modulates T-cell differentiation.

Together with M-CSF (macrophage-colony stimulating factor), GM-CSF regulates the number and function of macrophages. Macrophages activated by GM-CSF acquire a series of effector functions, all of which identify them as inflammatory macrophages. GM-CSF-activated macrophages produce proinflammatory cytokines, including TNF, IL-1β, IL-6, IL-23 and IL-12 and chemokines, such as CCL5, CCL22, and CCL24, which recruit T cells and other inflammatory cells into the tissue microenvironment.

The GM-CSF receptor is a member of the haematopoietin receptor superfamily. It is heterodimeric, consisting of an alpha and a beta subunit. The alpha subunit is highly specific for GM-CSF, whereas the beta subunit is shared with other cytokine receptors, including IL-3 and IL-5. This is reflected in a broader tissue distribution of the beta receptor subunit. The alpha subunit, GM-CSFRα, is primarily expressed on myeloid cells and non-haematopoietic cells, such as neutrophils, macrophages, eosinophils, dendritic cells, endothelial cells and respiratory epithelial cells. Full length GM-CSFRα is a 400 amino acid type I membrane glycoprotein that belongs to the type I cytokine receptor family and consists of a 22 amino acid signal peptide (positions 1-22), a 298 amino acid extracellular domain (positions 23-320), a transmembrane domain from positions 321-345 and a short 55 amino acid intra-cellular domain. The signal peptide is cleaved to provide the mature form of GM-CSFRα as a 378 amino acid protein. Complementary DNA (cDNA) clones of the human and murine GM-CSFRα are available and, at the protein level, the receptor subunits have 36% identity. GM-CSF is able to bind with relatively low affinity to the α subunit alone (Kd 1-5 nM) but not at all to the β subunit alone. However, the presence of both α and β subunits results in a high affinity ligand-receptor complex (Kd~100 pM). GM-CSF signaling occurs through its initial binding to the GM-CSFRα chain and then cross-linking with a larger subunit the common β chain to generate the high affinity interaction, which phosphorylates the JAK-STAT pathway. This interaction is also capable of signaling through tyrosine phosphorylation and activation of the MAP kinase pathway.

Pathologically, GM-CSF has been shown to play a role in exacerbating inflammatory, respiratory and autoimmune diseases. Neutralization of GM-CSF binding to GM-CSFRα is therefore a therapeutic approach to treating diseases and conditions mediated through GM-CSFR. Accordingly, the invention relates to a binding member that binds human GM-CSF or GM-CSFRα, or inhibits the binding of human GM-CSF to GM-CSFRα, and/or inhibits signaling that results from GM-CSF ligand binding to the receptor. Upon ligand binding, GM-CSFR triggers stimulation of multiple downstream signaling pathways, including JAK2/STATS, the MAPK pathway, and the PI3K pathway; all relevant in activation and differentiation of myeloid cells. The binding member may be a reversible inhibitor of GM-CSF signaling through the GM-CSFR.

GM-CSF Antagonists

A GM-CSF antagonist suitable for the present invention includes those therapeutic agents that can reduce, inhibit or abolish one or more GM-CSF mediated signaling including those described herein. For example, a suitable GM-CSF antagonist according to the invention includes, but is not limited to an anti-GM-CSF antibody or a fragment thereof, a soluble GM-CSF receptor and variants thereof including fusion proteins such as a GM-CSF soluble receptor-Fc fusion protein, an anti-GM-CSF receptor antibody or a fragment thereof, to name but a few.

In some embodiments, a suitable GM-CSF antagonist is an anti-GM-CSFRα antibody. Exemplary anti-GM-CSFRα monoclonal antibodies include those described in the international application PCT/GB2007/001108 filed on Mar. 27, 2007 which published as WO2007/110631, the EP application 120770487 filed on Oct. 10, 2010, U.S. application Ser. No. 11/692,008 filed on Mar. 27, 2007, U.S. application Ser. No. 12/294,616 filed on Sep. 25, 2008, U.S. application Ser. No. 13/941,409 filed on Jul. 12, 2013, U.S. application Ser. No. 14/753,792 filed on Nov. 30, 2010, international application PCT/EP2012/070074 filed on Oct. 10, 2012, which published as WO/2013/053767, international application PCT/EP2015/060902 filed on May 18, 2015, which published as WO2015/177097, international application PCT/EP2017/062479, filed on May 23, 2017, each of which are hereby incorporated by reference in their entirety. In one embodiment, the anti-GM-CSFRα monoclonal antibody is mavrilimumab. WO2007/110631 reports the isolation and characterization of the anti-GM-CSFRα antibody mavrilimumab and variants of it, which share an ability to neutralize the biological activity of GM-CSFRα with high potency. The functional properties of these antibodies are believed to be attributable, at least in part, to binding a Tyr-Leu-Asp-Phe-Gln motif at positions 226 to 230 of human GM-CSFRα, thereby inhibiting the association between GM-CSFRα and its ligand GM-CSF. Mavrilimumab is a human IgG4 monoclonal antibody designed to modulate macrophage activation, differentiation and survival by targeting the GM-CSFRα. It is a potent neutralizer of the biological activity of GM-CSFRα and, was shown to exert therapeutic effects by binding GM-CSFRα on leukocytes within the synovial joints of RA patients, leading to reduced cell survival and activation. The safety profile of the GM-CSFRα antibody mavrilimumab for in vivo use to date has been established in a Phase II clinical trial for rheumatoid arthritis (RA).

In certain embodiments, the antibody is comprised of two light chains and two heavy chains. The heavy chain variable domain (VH) comprises an amino acid sequence identified in SEQ ID NO: 1. The light chain variable domain (VL) comprises an amino acid sequence identified in SEQ ID NO: 2. The heavy and light chains each comprise complementarity determining regions (CDRs) and framework regions in the following arrangement:

FR1-CDR1-FR2-CDR2-FR3-CDR3-FR4

The mavrilimumab antibody heavy chain comprises CDRs: HCDR1, HCDR2, HCDR3 as identified by the amino acid sequences in SEQ ID NO: 3, 4 and 5 respectively. The light chain comprises CDRs: LCDR1, LCDR2, LCDR3 as identified by the amino acid sequences in SEQ ID NO: 6, 7 and 8 respectively.

```
Anti-GM-CSFRα Heavy Chain Variable Domain Amino
Acid Sequence
                                         (SEQ ID NO: 1)
QVQLVQSGAEVKKPGASVKVSCKVSGYTLTELSIHWVRQAPGKGLEWM

GGFDPEENEIVYAQRFQGRVTMTEDTSTDTAYMELSSLRSEDTAVYYCAI

VGSFSPLTLGLWGQGTMVTVSS

Anti-GM-CSFRα Light Chain Variable Domain Amino
Acid Sequence
                                         (SEQ ID NO: 2)
QSVLTQPPSVSGAPGQRVTISCTGSGSNIGAPYDVSWYQQLPGTAPKLLI

YHNNKRPSGVPDRFSGSKSGTSASLAITGLQAEDEADYYCATVEAGLSGS

VFGGGTKLTVL

Anti-GM-CSFRα Heavy Chain Variable Domain CDR1
(HCDR1) Amino Acid Sequence
                                         (SEQ ID NO: 3)
ELSIH Anti-GM-CSFRα Heavy Chain Variable Domain CDR2
(HCDR2) Amino Acid Sequence
                                         (SEQ ID NO: 4)
GFDPEENEIVYAQRFQG Anti-GM-CSFRα Heavy Chain Variable Domain CDR3
(HCDR3) Amino Acid Sequence
                                         (SEQ ID NO: 5)
VGSFSPLTLGL Anti-GM-CSFRα Light Chain Variable Domain CDR1
(LCDR1) Amino Acid Sequence
                                         (SEQ ID NO: 6)
TGSGSNIGAPYDVS Anti-GM-CSFRα Light Chain Variable Domain CDR2
(LCDR2) Amino Acid Sequence
                                         (SEQ ID NO: 7)
HNNKRPS Anti-GM-CSFRα Light Chain Variable Domain CDR3
(LCDR3) Amino Acid Sequence
                                         (SEQ ID NO: 8)
ATVEAGLSGSV
```

In some embodiments the anti-GM-CSFRα antibody for cancer treatment is a variant of mavrilimumab, selected from the GM-CSFα binding members disclosed in the application WO2007/11063 and WO2013053767, which is incorporated by reference in its entirety.

In some embodiments the anti-GM-CSFRα antibody for cancer treatment comprises CDR amino acid sequences with at least 75%, 80%, 85%, 90%, 91%, 92%, 93%, 94%, 95%, 96%, 97%, 98%, 99% or more identity with one or more of SEQ ID NO:3, SEQ ID NO: 4, SEQ ID NO: 5, SEQ ID NO: 6, SEQ ID NO: 7, and SEQ ID NO: 8.

In some embodiments the anti-GM-CSFRα antibody comprises a light chain variable domain having an amino acid sequence at least 90% identical to SEQ ID NO: 2 and a heavy chain variable domain having an amino acid sequence at least 90% identical to SEQ ID NO: 1. In some embodiments of the invention, an anti-GM-CSFRα antibody has a light chain variable domain amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 2 and a heavy chain variable domain amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 1. In some embodiments of the invention, an anti-GM-CSFRα antibody comprises a light chain variable domain that has the amino acid sequence set forth in SEQ ID NO: 2 and a heavy chain variable domain that has the amino acid sequence set forth in SEQ ID NO: 1. In some embodiments of the invention, a heavy chain constant region of an anti-GM-CSFRα antibody comprises CH1, hinge and CH2 domains derived from an IgG4 antibody fused to a CH3 domain derived from an IgG1 antibody. In some embodiments of the invention, a heavy chain constant region of an anti-GM-CSFRα antibody is, or is derived from, an IgG1, IgG2 or IgG4 heavy chain constant region. In some embodiments of the invention, a light chain constant region of an anti-GM-CSFRα antibody is, or is derived from, a lambda or kappa light chain constant region.

In some embodiments, the anti-GM-CSFRα inhibitor is a fragment of mavrilimumab antibody. In some embodiments the inhibitor comprises a single chain variable fragment (ScFv) comprising at least any one of the CDR sequences of SEQ ID NO: 3, 4, 5, 6, 7, or 8. In some embodiments the inhibitor is a fusion molecule comprising at least any one of the CDR sequences of SEQ ID NO: 3, 4, 5, 6, 7, or 8. In some embodiments, the anti-GM-CSFRα inhibitor sequence is a bispecific antibody comprising at least one of the CDR sequences of SEQ ID NO: 3, 4, 5, 6, 7, or 8.

In other embodiments, a suitable GM-CSF antagonist is an anti-GM-CSF antibody. Exemplary anti-GM-CSF monoclonal antibodies include those described in the international application PCT/EP2006/004696 filed on May 17, 2006 which published as WO2006/122797, international application PCT/EP2016/076225 filed on Oct. 31, 2016, which published as WO2017/076804, and international application PCT/US2018/053933 filed on Oct. 2, 2018, which published as WO/2019/070680 each of which are hereby incorporated by reference in their entirety. In one embodiment, the anti-GM-CSF monoclonal antibody is otilimab.

An anti-GM-CSFRα or anti-GM-CSF antibody of the present disclosure may be multispecific, e.g., bispecific. An antibody of the may be mammalian (e.g., human or mouse), humanized, chimeric, recombinant, synthetically produced, or naturally isolated. Exemplary antibodies of the present disclosure include, without limitation, IgG (e.g., IgG1, IgG2, IgG3, and IgG4), IgM, IgA (e.g., IgA1, IgA2, and IgAsec), IgD, IgE, Fab, Fab', Fab'2, F(ab')2, Fd, Fv, Feb, scFv, scFv-Fc, and SMIP binding moieties. In certain embodiments, the antibody is an scFv. The scFv may include, for example, a flexible linker allowing the scFv to orient in different directions to enable antigen binding. In various embodiments, the antibody may be a cytosol-stable scFv or intrabody that retains its structure and function in the reducing environment inside a cell (see, e.g., Fisher and DeLisa, J. Mol. Biol. 385(1): 299-311, 2009; incorporated by reference herein). In particular embodiments, the scFv is converted to an IgG or a chimeric antigen receptor according to methods known in the art. In embodiments, the antibody binds to both denatured and native protein targets. In embodiments, the antibody binds to either denatured or native protein.

In most mammals, including humans, whole antibodies have at least two heavy (H) chains and two light (L) chains connected by disulfide bonds. Each heavy chain consists of a heavy chain variable region (VH) and a heavy chain constant region (CH). The heavy chain constant region consists of three domains (CH1, CH2, and CH3) and a hinge region between CH1 and CH2. Each light chain consists of a light chain variable region (VL) and a light chain constant region (CL). The light chain constant region consists of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Antibodies include all known forms of antibodies and other protein scaffolds with antibody-like properties. For example, the anti-GM-CSFRα antibody can be a monoclonal antibody, a polyclonal antibody, human antibody, a humanized antibody, a bispecific antibody, a monovalent antibody, a chimeric antibody, or a protein scaffold with antibody-like properties, such as fibronectin or ankyrin repeats. The antibody can have any of the following isotypes: IgG (e.g., IgG1, IgG2, IgG3, and IgG4), IgM, IgA (e.g., IgA1, IgA2, and IgAsec), IgD, or IgE.

An antibody fragment may include one or more segments derived from an antibody. A segment derived from an antibody may retain the ability to specifically bind to a particular antigen. An antibody fragment may be, e.g., a Fab, Fab', Fab'2, F(ab')2, Fd, Fv, Feb, scFv, or SMIP. An antibody fragment may be, e.g., a diabody, triabody, affibody, nanobody, aptamer, domain antibody, linear antibody, single-chain antibody, or any of a variety of multispecific antibodies that may be formed from antibody fragments.

Examples of antibody fragments include: (i) a Fab fragment: a monovalent fragment consisting of VL, VH, CL, and CH1 domains; (ii) a F(ab')2 fragment: a bivalent fragment comprising two Fab fragments linked by a disulfide bridge at the hinge region; (iii) a Fd fragment: a fragment consisting of VH and CH1 domains; (iv) an Fv fragment: a fragment consisting of the VL and VH domains of a single arm of an antibody; (v) a dAb fragment: a fragment including VH and VL domains; (vi) a dAb fragment: a fragment that is a VH domain; (vii) a dAb fragment: a fragment that is a VL domain; (viii) an isolated complementarity determining region (CDR); and (ix) a combination of two or more isolated CDRs which may optionally be joined by one or more synthetic linkers. Furthermore, although the two domains of the Fv fragment, VL and VH, are coded for by separate genes, they can be joined, using recombinant methods, e.g., by a synthetic linker that enables them to be expressed as a single protein, of which the VL and VH regions pair to form a monovalent binding moiety (known as a single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more antigen-determining regions or constant regions derived from a first species and one or more antigen-determining regions or constant regions derived from a second species. Chimeric antibodies may be constructed, e.g., by genetic engineering. A chimeric antibody may include immunoglobulin gene segments belonging to different species (e.g., from a mouse and a human).

An antibody may be a human antibody. A human antibody refers to a binding moiety having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, e.g., mutations. A variation or additional amino acid may be introduced, e.g., by human manipulation. A human antibody of the present disclosure is not chimeric.

An antibody may be humanized, meaning that an antibody that includes one or more antigen-determining regions (e.g., at least one CDR) substantially derived from a non-human immunoglobulin or antibody is manipulated to include at least one immunoglobulin domain substantially derived from a human immunoglobulin or antibody. An antibody may be humanized using the conversion methods described herein, for example, by inserting antigen-recognition sequences from a non-human antibody encoded by a first vector into a human framework encoded by a second vector. For example, the first vector may include a polynucleotide encoding the non-human antibody (or a fragment thereof) and a site-specific recombination motif, while the second vector may include a polynucleotide encoding a human framework and a site-specific recombination complementary to a site-specific recombination motif on the first vector. The site-specific recombination motifs may be positioned on each vector such that a recombination event results in the insertion of one or more antigen-determining regions from the non-human antibody into the human framework, thereby forming a polynucleotide encoding a humanized antibody.

In certain embodiments, an antibody is converted from scFv to an IgG (e.g., IgG1, IgG2, IgG3, and IgG4). There are various methods in the art for converting scFv fragments to IgG. One such method of converting scFv fragments to IgG is disclosed in US patent application publication number 20160362476, the contents of which are incorporated herein by reference.

Treatment with GM-CSF Antagonist

In some embodiments, the present invention provides, among other things, a method of treating a subject infected with a virus, such as a coronavirus, by administering a GM-CSF antagonist. In some embodiments, the present invention provides, among other things, a method of treating a subject infected with a virus is provided comprising administering to the subject a (GM-CSF) antagonist at a therapeutically effective dose and an administration interval for a treatment period sufficient to improve, stabilize or reduce one or more symptoms of viral infection.

In some embodiments, the present invention provides, among other things, a method of inhibiting or reducing cytokine release syndrome (CRS) associated with an infection in a subject comprising administering to the subject a granulocyte-macrophage colony-stimulating factor (GM-CSF) antagonist at a therapeutically effective dose and an administration interval for a treatment period sufficient to improve, stabilize or reduce one or more symptoms of CRS. In some embodiments the infection is viral, bacterial or fungal.

In some embodiments, the one or more symptoms are associated with a respiratory tract infection, pneumonia (e.g., pneumocystis pneumonia), aspergillosis, pulmonary fibrosis, asthma, or acute respiratory distress syndrome. In some embodiments, the one or more symptoms are associated with a lung disease. In one embodiment, the lung disease is COVID-19 pneumonia.

In some embodiments, the therapeutically effective dose is delivered to attain a serum concentration of the GM-CSF antagonist between 100 ng/mL and 10000 ng/mL. Typically, the serum concentration of the GM-CSF antagonist is measured to determine the Cmax. In some embodiments, serum concentration of the GM-CSF antagonist is measured to determine the AUC. In some embodiments, the therapeutically effective dose is delivered to attain a serum concentration of the GM-CSF antagonist between about 100,000 ng/mL. In some embodiments, the therapeutically effective dose is delivered to attain a serum concentration of the GM-CSF antagonist between 3400 ng/mL and 8300 ng/ml.

Pro-Inflammatory and Anti-Inflammatory Cytokines

In some embodiments, the administering the GM-CSF antagonist decreases a quantity of a pro-inflammatory cytokine within the subject by between approximately 10% to approximately 90%.

In most embodiments, the composition described herein therapeutically affects a proinflammatory cytokine condition, for instance by facilitating or effectuating a decrease or reduction in a quantity of pro-inflammatory cytokines or pro-inflammatory mediators, within biological tissue (e.g., a body of a living organism when consumed thereby). In the context of the present disclosure, the term living organism refers to human beings and animals (i.e., organisms from the kingdom Animalia).

Examples of pro-inflammatory cytokines or pro-inflammatory mediators include interleukin-1 alpha (IL-1 a) and interleukin-1beta (IL-1/3) (hereinafter collectively referred to as interleukin-1 or IL-1), interleukin-6 (IL-6), interleukin-8 (IL-8), interleukin-11 (IL-11), interleukin-12 (IL-12), interleukin-17 (IL-17), interleukin-18 (IL-18), tumor necrosis factor-alpha (TNF-$\alpha$), interferon-gamma (IFN-$\gamma$), granulocyte-macrophage colony stimulating factor (GM-CSF), and transforming growth factor-beta (TGF-/3). It will be understood by a person having ordinary skill in the art that references to pro-inflammatory cytokines in most embodiments of the present disclosure can refer any one or more of pro-inflammatory cytokines known in the art, and including one or more of the above-listed examples of proinflammatory cytokines.

In some embodiments, the decrease in quantity of pro-inflammatory cytokines within the living organism helps to prevent, control, down-regulate, and/or stop the occurrence of a cytokine storm within the living organism. This is to say, in some embodiments, the phytochemical composition provides an anti-cytokine storm effect or function when consumed by the living organism. In several embodiments, the decrease in quantity of proinflammatory cytokines within the living organism helps to prevent, control, down-regulate, and/or stop inflammation within the living organism. This is to say, in several embodiments, the phytochemical composition facilitates or provides an anti-inflammatory effect or function when consumed by the living organism. In numerous embodiments, the decrease in quantity of pro-inflammatory cytokines within the living organism contributes to an anti-viral (e.g., anti-influenza) or viral modulatory effect or function (e.g., viral activity inhibitory effect) within the living organism. In some embodiments, the phytochemical composition therapeutically affects an antiinflammatory cytokine, anti-inflammatory mediator, or anti-inflammatory factor condition, for instance by facilitating or effectuating increase in a quantity of the anti-inflammatory cytokine, anti-inflammatory mediator, and/or anti-inflammatory factor within the living organism. Examples of anti-inflammatory cytokines, anti-inflammatory mediators, and/or anti-inflammatory factors include interleukin-2 (IL-2), interleukin-4 (IL-4), interleukin-13 (IL-13), and interferon-alpha (IFN-oi). A person having ordinary skill in the art will understand that a reference to anti-inflammatory cytokines, anti-inflammatory mediators, and/or anti-inflammatory factors in most embodiments of the present disclosure can relate to any one or more of anti-inflammatory cytokines, anti-inflammatory mediators, and/or anti-inflammatory factors known in the art, which includes the above-listed examples.

In some embodiments, the GM-CSF antagonist facilitates or effectuates inhibition of a viral neuraminidase (e.g., a decrease in an action of viral neuraminidase). In some embodiments of the present disclosure, the GM-CSF antagonist facilitates or effectuates a decrease in gene expression of one or more pro-inflammatory cytokines within the body. For example, in several embodiments, the GM-CSF antagonist facilitates or effectuates decrease in IL-1 gene expression of an immune cell (i.e. a cell that is involved in immune responses) of the body. Examples of immune cells include lymphocytes, phagocytic cells, fibroblasts, monocytes, neutrophils, and macrophages.

In some embodiments of the present disclosure, the GM-CSF antagonist facilitates or effectuates a decrease in secretion or release of one or more pro-inflammatory cytokines by an immune cell within the body. For example, in several embodiments, the GM-CSF antagonist facilitates or effectuates a decrease in IL-1 release or secretion from the immune cell.

In numerous embodiments, the decrease in gene expression of the pro-inflammatory cytokine (e.g., gene expression of IL-1) results in the decrease of secretion of the pro-inflammatory cytokine (e.g., decrease secretion of IL-1) by the immune cell, and hence a lower quantity of pro-inflammatory cytokine (e.g., lower quantity of IL-1) within the body. The lower quantity of pro-inflammatory cytokines (e.g., IL-1) within the body facilitates or effectuates or provides an anti-inflammatory effect.

In some embodiments of the present disclosure, the GM-CSF antagonist facilitates or effectuates an increase in gene expression of one or more anti-inflammatory cytokine within the body. For example, in several embodiments, the GM-CSF antagonist facilitates or effectuates increased gene expression of IL-2 by the immune cells of the body. In some embodiments of the GM-CSF antagonist facilitates or effectuates an increase in secretion or release of one or more anti-inflammatory cytokine by immune cells within the body. For example, in several embodiments, the GM-CSF antagonist facilitates or effectuates increased secretion of IL-2 by the immune cells of the body. In numerous embodiments, the increase in the gene expression of one or more antiinflammatory cytokines (e.g., IL-2) results in the increased secretion of the one or more antiinflammatory cytokines by the immune cells of the body, and therefore a higher quantity of anti-inflammatory cytokines within the body. The higher quantity of anti-inflammatory cytokines within the body facilitates or effectuates or provides an anti-inflammatory effect.

Glass-Ground Opacity (GGO)

In some embodiments, the administering of a GM-CSF antagonist according to the present invention decreases an area of ground-glass opacity in the lung.

Ground-glass opacification/opacity (GGO) is a descriptive term referring to an area of increased attenuation in the lung on computed tomography (CT) with preserved bronchial and vascular markings. CT scans of GGO also show a hazy opacity that does not obscure the underlying bronchial structures or pulmonary vessels, that indicates a partial filling of air spaces in the lungs by exudate or transudate, as well as interstitial thickening or partial collapse of lung alveoli. Ground-glass opacities are common but nonspecific, as they can be caused by viral or pyogenic infection.

Non-Cardiogenic Pulmonary Edema

In some embodiments, the administering of a GM-CSF antagonist decreases an intensity of non-cardiogenic pulmonary edema.

Pulmonary edema is a condition caused by excess fluid in the lungs. This fluid collects in the numerous air sacs in the lungs, making it difficult to breathe. Pulmonary edema that isn't caused by increased pressures in your heart is called noncardiogenic pulmonary edema.

In this condition, fluid may leak from the capillaries in your lungs' air sacs because the capillaries themselves become more permeable or leaky, even without the buildup of back pressure from your heart. Some factors that can cause noncardiogenic pulmonary edema include acute respiratory distress syndrome, high altitudes, nervous system conditions, averse drug reaction, negative pressure pulmonary edema, pulmonary embolism, viral infections, exposure to toxins, smoke inhalation, and near drowning.

In acute respiratory distress syndrome (ARDS) occurs when your lungs suddenly fill with fluid and inflammatory white blood cells. Many conditions can cause ARDS, including severe injuries (trauma), systemic infection (sepsis), pneumonia and severe bleeding.

Pulmonary edema can be caused by viral infections such as the coronavirus, hantavirus and dengue virus.

Combination Therapy with Antiviral Drug

In some embodiments, the method of the present invention comprises administering to a subject in need thereof a GM-CSF antagonist in combination with an antiviral drug. Various antiviral are known in the art and, in some embodiments, are administered to a subject in combination with a GM-CSF antagonist. For example, in some embodiments, a GM-CSF antagonist is administered in combination with a neuraminidase inhibitor and/or an adamantine derivative. Non-limiting examples of suitable neuraminidase inhibitor include Tamiflu® and Relenza®. Non-limiting examples of adamantine derivatives include amantadine and rimantadine. In some embodiments, a GM-CSF antagonist is administered in combination with one or more of the following antiviral drugs: Remdesivir, Chloroquine (e.g., hydroxychloroquine), Lopinavir and ritonavir, APN01, Favilavir, Baricitinib, Abacavir, Acyclovir, Adefovir, Amantadine, Ampligen, Amprenavir, Arbidol, Atazanavir, Atripla, Balavir, Baloxavir marboxil, Biktarvy, Cidofovir, Combivir, Darunavir, Delavirdine, Descovy, Didanosine, Docosanol, Dolutegravir, Ecoliever, Edoxudine, Efavirenz, Emtricitabine, Enfuvirtide, Entecavir, Famciclovir, Fomivirsen, Fosamprenavir, Foscarnet, Fosfonet, Ibacitabine, Idoxuridine, Imiquimod, Imunovir, Indinavir, Inosine, Integrase inhibitor, Interferon type I, Interferon type II, Interferon type III, Interferon, Lamivudine, Lopinavir, Loviride, Maraviroc, Methisazone, Moroxydine, Nelfinavir, Nevirapine, Nexavir, Nitazoxanide, Norvir, Nucleoside analogues, Oseltamivir, Peginterferon alfa-2a, Penciclovir, Peramivir, Pleconaril, Podophyllotixin, Protease inhibitor, Pyramidine, Raltegravir, Reverse transcriptase inhibitor, Ribavirin, Rimantadine, Ritonavir, Saquinavir, Sofosbuvir, Stavudine, Telaprevir, Tenofovir alafenamide, Tenofovir disoproxil, Tenofovir, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine.

In some embodiments, administering to a subject in need thereof a GM-CSF antagonist occurs simultaneously with the antiviral drug.

In some embodiments, administering to a subject in need thereof a GM-CSF antagonist occurs after administration of the antiviral drug. For example, administration of the GM-CSF antagonist occurs about 6 hours, 12 hours, 24 hours, 2 days, 3 days, 4 days, or 5 days after administration of the antiviral drug. In some embodiments, administration of the GM-CSF antagonist occurs more than 5 days after administration of the antiviral drug.

In some embodiments, administering to a subject in need thereof a GM-CSF antagonist occurs before administration of the antiviral drug. For example, administration of the antiviral drug occurs about 6 hours, 12 hours, 24 hours, 2 days, 3 days, 4 days, or 5 days after administration of the GM-CSF antagonist. In some embodiments, administration of the antiviral drug occurs more than 5 days after administration of the anti-GM-CSF antagonist.

Pharmaceutical Compositions and Administration

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Dosing Methods

In certain embodiments, the GM-CSF antagonist is administered by any route suitable for the administration of the GM-CSF antagonist, such as, for example, intravenous, or subcutaneous.

In some embodiments, the GM-CSF antagonist administered as an initial loading dose followed by a subsequent maintenance dose. In some embodiments, the maintenance dose is lower than the initial loading dose. In some embodiments, the maintenance dose is higher than the initial loading dose.

In some embodiments, a single administration of the GM-CSF antagonist is sufficient to improve, stabilize or reduce one or more symptoms for longer than five days, 1 week, 2 weeks, 4 weeks, 5 weeks, 7 weeks, 12 weeks or more.

In some embodiments a single administration of the GM-CSF antagonist is sufficient to improve, stabilize or reduce one or more symptoms so that the subject does not require a repeat dose.

In some embodiments, the therapeutic effective dose is between about 10 mg and 750 mg. In some embodiments, the therapeutic effective dose is between about 30 mg and 250 mg. For example, In some embodiments, the therapeutically effective dose is about 30 mg, 35 mg, 40 mg, 45 mg, 50 mg, 55 mg, 60 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 300 mg, 325 mg, 350 mg, 375 mg, 400 mg, 425 mg, 450 mg, 500 mg, 550 mg, 600 mg, 350 mg, 700 mg, or 750 mg.

In some embodiments, the therapeutically effective dose is between 37 and 225 mg.

In some embodiments, the therapeutically effective dose is between 0.5 mg/kg and 10 mg/kg. In some embodiments, the therapeutically effective dose is between 1 mg/kg and 3 mg/kg. In some embodiments, the therapeutically effective dose is about 0.5 mg/kg. In some embodiments, the therapeutically effective dose is about 1.0 mg/kg. In some embodiments, the therapeutically effective dose is about 1.5 mg/kg. In some embodiments, the therapeutically effective dose is about 2.0 mg/kg. In some embodiments, the therapeutically effective dose is about 2.5 mg/kg. In some embodiments, the therapeutically effective dose is about 3.0 mg/kg. In some embodiments, the therapeutically effective dose is about 3.5 mg/kg. In some embodiments, the therapeutically effective dose is about 4.0 mg/kg. In some embodiments, the therapeutically effective dose is about 4.5 mg/kg. In some embodiments, the therapeutically effective dose is about 5.0 mg/kg. In some embodiments, the therapeutically effective dose is about 6.0 mg/kg. In some embodiments, the therapeutically effective dose is about 7.0 mg/kg. In some embodiments, the therapeutically effective dose is about 8.0 mg/kg. In some embodiments, the therapeutically effective dose is about 9.0 mg/kg. In some embodiments, the therapeutically effective dose is about 10.0 mg/kg.

In some embodiments, the GM-CSF antagonist is administered to maintain a serum concentration of the GM-CSF antagonist between 100 ng/mL and 10,000 ng/mL for a period of time, such as for example for at least 3 days, 4 days, 5 days, 1 week, 2 weeks, 5 weeks, 6 weeks or more.

In some embodiments, the therapeutically effective dose is delivered to attain a serum concentration of the GM-CSF antagonist above 3400 ng/mL after 1 day, 3 days, 4, days, 5 days, 1 week, 2 weeks, 3 weeks, 5 weeks, up to 6 weeks.

In some embodiments, the therapeutically effective dose is delivered to attain a serum concentration of the GM-CSF antagonist above 8300 ng/mL after 1 day, 3 days, 4, days, 5 days, 1 week, 2 weeks, 3 weeks, 5 weeks, up to 6 weeks.

In some embodiments, the therapeutically effective dose is delivered to attain a serum concentration of the GM-CSF antagonist between 3400 ng/mL and 8300 ng/ml for 1 day, 3 days, 4, days, 5 days, 1 week, 2 weeks, 3 weeks, 5 weeks, up to 6 weeks.

In some embodiments, the frequency of the administration of GM-CSF is once every 5 days, once every week, once every two weeks, once every three weeks, once every four weeks, or once every five weeks.

In some embodiments, a repeat dose of the GM-CSF antagonist is administered to the subject. For example, a repeat dose is administered to the subject if one or more symptoms do not improve, stabilize or reduce one or more symptoms within 24 hours, 3 days, 4 days, or 7 days. In some embodiments, a repeat dose is administered to the subject if one or more symptoms do not improve, stabilize or reduce one or more symptoms after 24 hours. In some embodiments, repeat dose is the same dose as the initial dose. In some embodiments, the repeat dose is higher than the initial dose. In some embodiments, the repeat does is lower than the initial dose. In some embodiments, the repeat dose is between 0.5 mg/kg and 10 mg/kg. In some embodiments, the repeat dose is between 1.0 mg/kg and 3 mg/kg. In some embodiments, the repeat dose is about 0.5 mg/kg. In some embodiments, the repeat dose is about 1.0 mg/kg. In some embodiments, the repeat dose is about 1.5 mg/kg. In some embodiments, the repeat dose is about 2.0 mg/kg. In some embodiments, the repeat dose is about 2.5 mg/kg. In some embodiments, the repeat dose is about 3.0 mg/kg. In some embodiments, the repeat dose is about 3.5 mg/kg. In some embodiments, the repeat dose is about 4.0 mg/kg. In some embodiments, the repeat dose is about 5.0 mg/kg. In some embodiments, the repeat dose is about 6.0 mg/kg. In some embodiments, the repeat dose is about 7.0 mg/kg. In some embodiments, the repeat dose is about 8.0 mg/kg. In some embodiments, the repeat dose is about 10.0 mg/kg.

In some embodiments, the GM-CSF antagonist is administered in combination with a second active agent. In some embodiments, the second active agent is an antiviral drug. In some embodiments, the second active agent is an antibiotic, a decongestant, an antihistamine, a pain reliever, a fever reducer, and/or a cough suppressant. In some embodiments, administration of the second active agent occurs simultaneously with administration of the GM-CSF antagonist. In some embodiments, administration of the second active agent occurs after administration of the GM-CSF antagonist. In some embodiments, administration of the second active agent occurs before administration of the GM-CSF antagonist.

Patient Selection

In some embodiments, a method comprises selecting a subject prior to administering the GM-CSF antagonist. In some embodiments, a method comprises selecting a subject based on one or more biomarkers associated with the disease condition.

In some embodiments, a method comprises selecting a subject who has an elevated level of the inflammation marker in a subject's serum. In some embodiments, the method comprises selecting a subject based on the level of C-reactive protein (CRP). In some embodiments, a subject's CRP level is between 0.5 and 10 mg/dL at baseline. In some embodiments, a subject's CRP level is between 1 and 8 mg/dL at baseline. In some embodiments, a subject's CRP level is between 5 and 7 mg/dL at baseline. In some embodiments, a subject's CRP level is above normal ($\geq 0.5$ mg/dL) at baseline. One skilled in the art would easily convert mg/dL to mg/L, by multiplying 10. In some embodiments, a subject's CRP level is between 5 and 100 mg/L at baseline. In some embodiments, a subject's CRP level is between 10 and 80 mg/L at baseline. In some embodiments, a subject's CRP level is between 50 and 70 mg/L at baseline. In some embodiments, a subject's CRP level is above normal ($\geq 5$ mg/L) at baseline.

In some embodiments, a method comprises selecting a subject based on the level of D-dimer. D-dimer is a fibrin degradation product, a small protein fragment present in the blood after a blood clot is degraded by fibrinolysis. In some embodiments, a subject's D-dimer level is greater than 0.1

µg/ml at baseline. In some embodiments, a subject's D-dimer level is greater than 0.5 µg/ml at baseline. In some embodiments, a subject's D-dimer level is greater than 0.6 µg/ml at baseline. In some embodiments, a subject's D-dimer level is greater than 0.7 µg/ml at baseline. In some embodiments, a subject's D-dimer level is greater than 0.8 µg/ml at baseline. In some embodiments, a subject's D-dimer level is greater than 0.9 µg/ml at baseline. In some embodiments, a subject's D-dimer level is greater than 1.0 µg/ml at baseline. In some embodiments, a subject's D-dimer level is greater than 1.5 µg/ml at baseline. In some embodiments, a subject's D-dimer level is greater than 2.0 µg/ml at baseline. In some embodiments, a subject's D-dimer level is greater than 2.5 µg/ml at baseline. In some embodiments, a subject's D-dimer level is greater than 3.0 µg/ml at baseline. In some embodiments, a subject's D-dimer level is greater than 4.0 µg/ml at baseline. In some embodiments, a subject's D-dimer level is greater than 5.0 µg/ml at baseline. In some embodiments, a subject's D-dimer level is greater than 8.0 µg/ml at baseline. In some embodiments, a subject's D-dimer level is greater than 10.0 µg/ml at baseline. In some embodiments, a subject's D-dimer level is greater than 12.0 µg/ml at baseline. In some embodiments, a subject's D-dimer level is greater than 15.0 µg/ml at baseline. In some embodiments, a subject's D-dimer level is greater than 20.0 µg/ml at baseline. In some embodiments, a subject's D-dimer level is greater than 25.0 µg/ml at baseline. In some embodiments, a subject's D-dimer level is greater than 30.0 µg/ml at baseline. In some embodiments, a subject's D-dimer level is greater than 40.0 µg/ml at baseline. In some embodiments, a subject's D-dimer level is greater than 50.0 µg/ml at baseline.

In some embodiments, a subject's D-dimer level is between 0.1 and 50 µg/ml at baseline. In some embodiments, a subject's D-dimer level is between 0.1 and 50 µg/ml at baseline. In some embodiments, a subject's D-dimer level is between 0.5 and 30 µg/ml at baseline. In some embodiments, a subject's D-dimer level is between 1.0 and 10 µg/ml at baseline. In some embodiments, a subject's D-dimer level is between 0.5 and 1.0 µg/ml at baseline. In some embodiments, a subject's D-dimer level is between 0.5 and 4.0 µg/ml at baseline. In some embodiments, a subject's D-dimer level is between 1.5 and 25 µg/ml at baseline. In some embodiments, a subject's D-dimer level is between 0.3 and 1.0 µg/ml at baseline. In some embodiments, a subject's D-dimer level is less than 50 µg/ml at baseline. In some embodiments, a subject's D-dimer level is less than 40 µg/ml at baseline. In some embodiments, a subject's D-dimer level is less than 30 µg/ml at baseline. In some embodiments, a subject's D-dimer level is less than 25 µg/ml at baseline. In some embodiments, a subject's D-dimer level is less than 20 µg/ml at baseline. In some embodiments, a subject's D-dimer level is less than 15 µg/ml at baseline. In some embodiments, a subject's D-dimer level is less than 10 µg/ml at baseline. In some embodiments, a subject's D-dimer level is less than 8 µg/ml at baseline. In some embodiments, a subject's D-dimer level is less than 6.0 µg/ml at baseline. In some embodiments, a subject's D-dimer level is less than 5.0 µg/ml at baseline. In some embodiments, a subject's D-dimer level is less than 4.0 µg/ml at baseline. In some embodiments, a subject's D-dimer level is less than 3.5 µg/ml at baseline. In some embodiments, a subject's D-dimer level is less than 3.0 µg/ml at baseline. In some embodiments, a subject's D-dimer level is less than 2.5 µg/ml at baseline. In some embodiments, a subject's D-dimer level is less than 2.0 µg/ml at baseline. In some embodiments, a subject's D-dimer level is less than 1.5 µg/ml at baseline. In some embodiments, a subject's D-dimer level is less than 1.0 µg/ml at baseline. In some embodiments, a subject's D-dimer level is about or less than 0.5 µg/ml at baseline.

In some embodiments, a method comprises selecting a subject based on lymphocyte count. In some embodiments, a subject's lymphocyte count is less than $5.0 \times 10^9$ per L at baseline. In some embodiments, a subject's lymphocyte count is less than $2.0 \times 10^9$ per L at baseline. In some embodiments, a subject's lymphocyte count is less than $1.8 \times 10^9$ per L at baseline. In some embodiments, a subject's lymphocyte count is less than $1.6 \times 10^9$ per L at baseline. In some embodiments, a subject's lymphocyte count is less than $1.4 \times 10^9$ per L at baseline. In some embodiments, a subject's lymphocyte count is less than $1.2 \times 10^9$ per L at baseline. In some embodiments, a subject's lymphocyte count is less than $1.0 \times 10^9$ per L at baseline. In some embodiments, a subject's lymphocyte count is less than $0.8 \times 10^9$ per L at baseline. In some embodiments, a subject's lymphocyte count is less than $0.6 \times 10^9$ per L at baseline. In some embodiments, a subject's lymphocyte count is less than $0.4 \times 10^9$ per L at baseline. In some embodiments, a subject's lymphocyte count is less than $0.2 \times 10^9$ per L at baseline. In some embodiments, a subject's lymphocyte count is between $0.1 \times 10^9$ and $2.0 \times 10^9$ per L at baseline. In some embodiments, a subject's lymphocyte count is between $0.5 \times 10^9$ and $1.5 \times 10^9$ per L at baseline. In some embodiments, a subject's lymphocyte count is between $0.8 \times 10^9$ and $2.0 \times 10^9$ per L at baseline. In some embodiments, a subject's lymphocyte count is between $0.3 \times 10^9$ and $0.8 \times 10^9$ per L at baseline.

In some embodiments, a method comprises selecting a subject based on the level of IL-6. In some embodiments, a subject's IL-6 level is greater than 1.0 pg/mL at baseline. In some embodiments, a subject's IL-6 level is greater than 2.0 pg/mL at baseline. In some embodiments, a subject's IL-6 level is greater than 3.0 pg/mL at baseline. In some embodiments, a subject's IL-6 level is greater than 4.0 pg/mL at baseline. In some embodiments, a subject's IL-6 level is greater than 5.0 pg/mL at baseline. In some embodiments, a subject's IL-6 level is greater than 5.5 pg/mL at baseline. In some embodiments, a subject's IL-6 level is greater than 6.0 pg/mL at baseline. In some embodiments, a subject's IL-6 level is greater than 6.5 pg/mL at baseline. In some embodiments, a subject's IL-6 level is greater than 7.0 pg/mL at baseline. In some embodiments, a subject's IL-6 level is greater than 8.0 pg/mL at baseline. In some embodiments, a subject's IL-6 level is greater than 9.0 pg/mL at baseline. In some embodiments, a subject's IL-6 level is greater than 10.0 pg/mL at baseline. In some embodiments, a subject's IL-6 level is greater than 11.0 pg/mL at baseline. In some embodiments, a subject's IL-6 level is greater than 12.0 pg/mL at baseline. In some embodiments, a subject's IL-6 level is greater than 14.0 pg/mL at baseline. In some embodiments, a subject's IL-6 level is greater than 15.0 pg/mL at baseline. In some embodiments, a subject's IL-6 level is greater than 16.0 pg/mL at baseline. In some embodiments, a subject's IL-6 level is greater than 18.0 pg/mL at baseline. In some embodiments, a subject's IL-6 level is greater than 20.0 pg/mL at baseline. In some embodiments, a subject's IL-6 level is greater than 25.0 pg/mL at baseline.

In some embodiments, a subject's IL-6 level is between 1.0 and 20 pg/mL at baseline. In some embodiments, a subject's IL-6 level is between 5.0 and 15 pg/mL at baseline. In some embodiments, a subject's IL-6 level is between 5.0 and 7.0 pg/mL at baseline. In some embodiments, a subject's IL-6 level is less than 30 pg/mL at baseline. In some embodiments, a subject's IL-6 level is less than 20 pg/mL at baseline. In some embodiments, a subject's IL-6 level is less than 18 pg/mL at baseline. In some embodiments, a subject's IL-6 level is less than 15 pg/mL at baseline. In some embodiments, a subject's IL-6 level is less than 12 pg/mL at baseline. In some embodiments, a subject's IL-6 level is less than 10 pg/mL at baseline. In some embodiments, a subject's IL-6 level is less than 9 pg/mL at baseline. In some embodiments, a subject's IL-6 level is less than 8 pg/mL at baseline. In some embodiments, a subject's IL-6 level is less than 7 pg/mL at baseline. In some embodiments, a subject's IL-6 level is less than 6 pg/mL at baseline. In some embodiments, a subject's IL-6 level is less than 5 pg/mL at baseline. In some embodiments, a subject's IL-6 level is less than 4 pg/mL at baseline. In some embodiments, a subject's IL-6 level is less than 3 pg/mL at baseline.

In some embodiments, a method comprises selecting a subject based on the level of ferritin in serum. In some embodiments, a subject's serum ferritin level is greater than 10 μg/L at baseline. In some embodiments, a subject's serum ferritin level is greater than 20 μg/L at baseline. In some embodiments, a subject's serum ferritin level is greater than 50 μg/L at baseline. In some embodiments, a subject's serum ferritin level is greater than 100 μg/L at baseline. In some embodiments, a subject's serum ferritin level is greater than 150 μg/L at baseline. In some embodiments, a subject's serum ferritin level is greater than 200 μg/L at baseline. In some embodiments, a subject's serum ferritin level is greater than 250 μg/L at baseline. In some embodiments, a subject's serum ferritin level is greater than 300 μg/L at baseline. In some embodiments, a subject's serum ferritin level is greater than 350 μg/L at baseline. In some embodiments, a subject's serum ferritin level is greater than 400 μg/L at baseline. In some embodiments, a subject's serum ferritin level is greater than 450 μg/L at baseline. In some embodiments, a subject's serum ferritin level is greater than 500 μg/L at baseline. In some embodiments, a subject's serum ferritin level is greater than 550 μg/L at baseline. In some embodiments, a subject's serum ferritin level is greater than 600 μg/L at baseline. In some embodiments, a subject's serum ferritin level is greater than 650 μg/L at baseline. In some embodiments, a subject's serum ferritin level is greater than 700 μg/L at baseline. In some embodiments, a subject's serum ferritin level is greater than 800 μg/L at baseline. In some embodiments, a subject's serum ferritin level is greater than 900 μg/L at baseline. In some embodiments, a subject's serum ferritin level is greater than 1000 μg/L at baseline. In some embodiments, a subject's serum ferritin level is greater than 1200 μg/L at baseline. In some embodiments, a subject's serum ferritin level is greater than 1400 μg/L at baseline. In some embodiments, a subject's serum ferritin level is greater than 1500 μg/L at baseline. In some embodiments, a subject's serum ferritin level is greater than 1600 μg/L at baseline. In some embodiments, a subject's serum ferritin level is greater than 1800 μg/L at baseline. In some embodiments, a subject's serum ferritin level is greater than 2000 μg/L at baseline.

In some embodiments, the method comprises selecting a subject based on the level of troponin. Typically, the normal range for troponin is between 0 and 0.4 ng/mL. In some embodiments, a subject's troponin level is elevated two-, five-, ten-fold above normal. In some embodiments, a subject's troponin level is above 0.4 ng/mL at baseline. In some embodiments, a subject's troponin level is above 0.8 ng/mL at baseline. In some embodiments, a subject's troponin level is above 1.0 ng/mL at baseline. In some embodiments, a subject's troponin level is above 2.0 ng/mL at baseline. In some embodiments, a subject's troponin level is above 4.0 ng/mL at baseline. In some embodiments, a subject's troponin level is above 10 ng/mL at baseline.

In some embodiments, the method comprises selecting a subject based on the level of lactate dehydrogenase (LDH). Typically, the normal range for LDH is between 140 and 280 U/L. In some embodiments, a subject's troponin level is elevated two-, five-, ten-fold above normal. In some embodiments, a subject's LDH level is above 200 U/L at baseline. In some embodiments, a subject's LDH level is above 250 U/L at baseline. In some embodiments, a subject's LDH level is above 280 U/L at baseline. In some embodiments, a subject's LDH level is above 300 U/L at baseline. In some embodiments, a subject's LDH level is above 320 U/L at baseline. In some embodiments, a subject's LDH level is above 340 U/L at baseline. In some embodiments, a subject's LDH level is above 360 U/L at baseline. In some embodiments, a subject's LDH level is above 380 U/L at baseline. In some embodiments, a subject's LDH level is above 400 U/L at baseline. In some embodiments, a subject's LDH level is above 450 U/L at baseline. In some embodiments, a subject's LDH level is above 500 U/L at baseline. In some embodiments, a subject's LDH level is above 550 U/L at baseline. In some embodiments, a subject's LDH level is above 600 U/L at baseline.

In some embodiments, the method comprises selecting a subject based on the Sequential Organ Failure Assessment (SOFA) score. The Sequential Organ Failure Assessment (SOFA) Score is a mortality prediction score that is based on the degree of dysfunction of six organ systems. The score is calculated on admission and every 24 hours until discharge using the worst parameters measured during the prior 24 hours. In some embodiments, a subject has a SOFA score of about or greater than 2 at baseline. In some embodiments, a subject has a SOFA score of about or greater than 5 at baseline. In some embodiments, a subject has a SOFA score of about or greater than 7 at baseline. In some embodiments, a subject has a SOFA score of about or greater than 9 at baseline. In some embodiments, a subject has a SOFA score of about or greater than 10 at baseline. In some embodiments, a subject has a SOFA score of about or greater than 12 at baseline. In some embodiments, a subject has a SOFA score of about or greater than 14 at baseline. In some embodiments, a subject has a SOFA score of about or greater than 15 at baseline. In some embodiments, a subject has a SOFA score of about or greater than 20 at baseline. In some embodiments, a subject has a SOFA score between 0 and 6 at baseline at baseline. In some embodiments, a subject has a SOFA score between 7 and 9 at baseline at baseline. In some embodiments, a subject has a SOFA score between 10 and 12 at baseline at baseline. In some embodiments, a subject has a SOFA score between 13 and 14 at baseline at baseline. In some embodiments, a subject has a SOFA score between 15 and 24 at baseline at baseline. In some embodiments, a subject has a SOFA score between 10 and 24 at baseline at baseline.

In some embodiments, a method comprises selecting a subject based on age, comorbidities, lymphocytopenia, elevated alanine aminotransferase, creatine kinase, and/or prothrombin.

In some embodiments, a method comprises selecting a subject who has hypoxia. In some embodiments, a subject is administered with the GM-CSF antagonist prior to the worsening of hypoxia. In some embodiments, a subject is administered GM-CSF antagonist prior to respiratory compromise or failure. In some embodiments, a subject is administered GM-CSF antagonist prior to receiving respiratory support, wherein the respiratory support is supplemental oxygen, non-invasive ventilation, non-invasive mechanical ventilation (e.g. continuous positive airway pressure (CPAP) or bi-level positive airway pressure (Bi-PAP)), or mechanical ventilation. In some embodiments, a subject is administered GM-CSF antagonist after receiving respiratory support, wherein the respiratory support is supplemental oxygen, non-invasive ventilation, non-invasive mechanical ventilation (e.g. continuous positive airway pressure (CPAP) or \ bi-level positive airway pressure (Bi-PAP)), or mechanical ventilation. In some embodiments, a method comprises selecting a subject who is present with fever. In some embodiments, a method comprises selecting a subject who is present with cough. In some embodiments, a subject is present with fever. In some embodiments, a subject is present with cough. In some embodiments, a subject is not in an ambulatory care setting or in an intensive care center. In some embodiments, a subject is in an ambulatory care setting or in an intensive care center. In some embodiments, a subject is treated early that the subject does not require ventilation. In some embodiments, a subject is treated early that the subject does not experience respiratory compromise or respiratory failure.

In some embodiments, a method comprises selecting a subject based on the use of intubation prior to the treatment. In some embodiments, the subjects are not intubated prior to the administration of the GM-CSF antagonist.

EXAMPLES

While certain compounds, compositions and methods of the present invention have been described with specificity in accordance with certain embodiments, the following examples serve only to illustrate the invention and are not intended to limit the same. While certain compounds, compositions and methods of the present invention have been described with specificity in accordance with certain embodiments, the following examples serve only to illustrate the invention and are not intended to limit the same.

Example 1. Treatment of COVID-19 with an Anti-GM-CSFRα Antibody

The study in this example is a Phase II, interventional study to evaluate the efficacy, safety and tolerability of an anti-GM-CSFRα antibody in subjects with COVID-19. Non-mechanically ventilated patients suffering from severe pulmonary involvement of COVID-19, acute respiratory distress, fever and clinical and biological markers of systemic hyperinflammation status, were treated with a single-dose of anti-GM-CSFRα antibody. The objective was to reduce incidence of progression of acute respiratory failure, the need of mechanical ventilation, and the transfer to the intensive care unit.

The primary objective of this study was also to demonstrate that the early treatment with the anti-GM-CSFRα antibody administered intravenously in addition to the best available antiviral therapy with protease inhibitors and hydroxychloroquine is able to reduce the progression of acute respiratory failure, the need of mechanical ventilation and the transfer to the intensive care unit, in patients with severe COVID-19 pneumonia/or with CT scan imaging suggestive of pulmonary involvement due to COVID-19 and clinical and biological features of hyper inflammation. The secondary objectives of this study were to evaluate i) the safety of the anti-GM-CSFRα antibody in the cohort of patients treated (incidence of adverse events), ii) the overall mortality rate and during hospitalization at day 28 and 90, iii) the length of hospitalization, iv) the continuous progression of respiratory failure, v) the incidence of PCR 2019-nCoV negativity in swab samples, and (vi) the titers of anti-2019-nCoV protective antibodies after treatment.

Primary Outcome

The primary outcome is the Respiratory failure free survival according to the following criteria:
 For those patients with a baseline PaO2/FiO2≥200 (Nava, Lancet 2009): Progression of respiratory failure is defined by severe gas transfer deficit (PaO2/FiO2<200) or persistent respiratory distress while receiving oxygen (persistent marked dyspnea, use of accessory respiratory muscles, paradoxical respiratory movements)
 For those patients with a baseline PaO2/FiO2<200 (Nava, Lancet 2009): increase in $O_2$ support up to intubation and mechanical ventilation
 For those patients who are already on mechanical ventilation Progression of respiratory failure is defined by prolonged mechanical ventilation (more than 14 days).

Secondary Outcomes

The secondary outcomes are:
 Overall mortality at day 28, and day 90 and overall hospital-related mortality
 Incidence of negativity of 2019-nCoV PCR on upper respiratory tract specimen (nasopharyngeal swab (NPS) or viral throat swab)
 Days of intensive care unit hospitalization
 Days of sub-intensive care unit hospitalization
 Frequency and incidence of adverse drug reactions (ADR) and SAE
 Continuous progression based on P/F monitoring Study Population The study enrolled consecutive patients suffering from severe pulmonary involvement of COVID-19 or CT scan suggestive of severe pulmonary involvement with acute respiratory distress and clinical and biological markers of systemic hyperinflammation status.
 Inclusion Criteria:
  Documented COVID-19 pneumonia: defined as upper respiratory tract specimen (nasopharyngeal swab (NPS) or viral throat swab) positive for 2019-nCoV and/or imaging at computed tomography scan suggestive of COVID-19 pneumonia
  Concomitant treatment for COVID19 with protease inhibitors and with hydroxychloroquine (or the equivalent standard base treatment for COVID-19)
  SpO2<92% on air without oxygen support or decrease in 3% of basal SpO2 or P/F≤300
  Lactate dehydrogenase (LDH)>normal range and at least one of the following increased level of: C-reactive Protein (CRP≥100 mg/L) or IL-6 (≥40 pg/ml) or ferritin (≥900 ng/ml).
  Informed consent or as per IRB indication
 Exclusion Criteria:
  Onset of Covid19 pneumonia ≥14 days
  Uncontrolled systemic infection (other than 2019-nCoV)
  Hypersensitivity to the active substance or to any of the excipients of the experimental drug
  Total neutrophil count <1500/mm3
  Severe concomitant illness:
   patients with severe hepatic cirrhosis
   patients with diverticulitis/diverticulosis or other medical condition at risk of diverticular perforation
   Patients who, on the basis of the investigator's clinical judgement, are not able to receive the treatment Shortage of drug Pregnancy or lactation Safety Monitoring The Data Safety Monitoring Board (DSMB) in collaboration with the Writing Committee will make one monitoring at 20 evaluable patients (concomitantly with the interim analysis) to ensure the safety of patients enrolled in the study. In case of response rate less than 50% an increase of the drug dose up to 800 mg will be performed.

End of the Study and Timing

The end of enrollment is based on the interim analysis results, according to the adaptive model of the study. The follow-up according to the protocol is 3 months for each patient enrolled. The end of the study, including statistical analysis and drafting of the final report, is expected at 1 months from the last follow-up of the last patient enrolled. The study is performed in 3 months starting from the first patient enrolled.

Study Procedure for Patients Evaluation—Baseline (Study Eligibility Screening)

Patients were be treated according to the standard institutional procedures and will be tested at enrollment for:

Complete blood count (CBC), serum biochemical tests (including renal and liver function), albumin, total protein, coagulation profile and D-dimer, myocardial enzymes, lactate dehydrogenase (LDH), C-reactive protein, serum ferritin, IL-6, quantiferon, HBV, HCV, HIV serology.

Patients should receive the best available therapy, a combination of antiviral with protease inhibitors and with hydroxychloroquine in combination to an anti-GM-CSFRα antibody 6 mg/kg body weight infused intravenously in one hour.

Adverse Event Reporting

For the purpose of this protocol adverse events are classified into the following categories:

Adverse Event (AE): Adverse event' means any untoward medical occurrence in a subject to whom a medicinal product is administered and which does not necessarily have a causal relationship with this treatment;

Adverse Drug Reaction (ADR): is "a response to a medicine which is noxious and unintended, and which occurs at doses normally used in man".

In this description it is of importance that it concerns the response of a patient, in which individual factors may play an important role, and that the phenomenon is noxious (an unexpected therapeutic response, for example, may be a side effect but not an adverse reaction).

Serious Adverse Event (SAE): Serious adverse event' means any untoward medical occurrence that at any dose requires inpatient hospitalization or prolongation of existing hospitalization, results in persistent or significant disability or incapacity, results in a congenital anomaly or birth defect, is life-threatening, or results in death;

Unexpected Serious Adverse Event (USAE): means a serious adverse reaction, the nature, severity or outcome of which is not consistent with the reference safety information;

Unexpected Adverse Event: An unexpected adverse event is an event, the nature or severity of which is not consistent with applicable product information.

During study follow up SAEs and AEs were documented using CTC AE v4.

For unconscious or obnubilated patients ethical committee indications are followed.

Study Results

To date, 13 patients have received a single dose of anti-GM-CSFRα antibody 6 mg/kg IV via 60-minute infusion as an add-on to standard-of-care. The patients received treatment with hydroxychloroquine, a 3-day course of azathioprine, and ritonavir/lopinavir as per local treatment protocol, and maximal supportive therapy with oxygen and/or NIV with continuous positive airway pressure (CPAP), as clinically indicated. All patients have tolerated the infusion well. Of these, one patient was on ventilation at the time of the infusion. He tolerated the infusion well and remains in stable condition.

The data for the first cohort of six of the treated patients enrolled in the study are shown below. These patients were suffering from severe pulmonary involvement of COVID-19, acute respiratory distress, fever and clinical and biological markers of systemic hyperinflammation status. The patient characteristics are summarized in Table 1.

TABLE 1

Patent Data prior to the treatment

| Patient | Male/Female | Age | Respiratory requirement | Systematic Inflammation | Fever | Other characteristics | Days between screening and treatment |
|---|---|---|---|---|---|---|---|
| 1 | M | 52 | Requires CPAP | severe | Feverish | Carrier of thalassemia trait; otherwise healthy | 3 |
| 2 | F | 57 | Requires placement of high-flow-oxygen-facemask with reservoir-bag | Severe | Febrile | Hypertensive on treatment; history of NSTEMI | 3 |
| 3 | M | 59 | Requires placement of high-flow-oxygen-facemask with reservoir-bag (FiO2 40%) | Severe | Febrile | | 3 |

TABLE 1-continued

Patent Data prior to the treatment

| Patient | Male/Female | Age | Respiratory requirement | Systematic Inflammation | Fever | Other characteristics | Days between screening and treatment |
|---|---|---|---|---|---|---|---|
| 4 | M | 59 | Requires placement of high-flow-oxygen-facemask with reservoir-bag (FiO2 40%) | Severe | Febrile | | 1 |
| 5 | M | 66 | Requires placement of high-flow-oxygen-facemask with reservoir-bag (FiO2 40%) | Severe | Febrile | | 3 |
| 6 | M | 56 | CPAP | Severe | Febrile | | 4 |

All first cohort of 6 patients showed an initial resolution of fever and improvement in oxygenation within 1-3 days. No patient progressed to require mechanical ventilation. 2 patients were discharged from the hospital after 4-5 days breathing room air. Anti-GM-CSFRα antibody was well-tolerated.

TABLE 2

Efficacy of the anti-GM-CSFRa antibody in treating COVID-19 for 6 patients

| Patient 1 | FiO2 | sO2 (%) | pO2 (torr) | PaO2/FiO2 | NIV | fever | Worse/Improved | CRP mg/dL | IL-6 | LDH |
|---|---|---|---|---|---|---|---|---|---|---|
| Screening | 21 | 96 | 72 | 342.86 | | yes - 8 d | N/A | | | |
| Baseline | 90 | 93 | 87 | 96.67 | no | yes | N/A | 22.3 | | 422 |
| 24 h | 90 | 100 | | | yes | yes | Worse | 16.8 | | 592 |
| 48 h | 90 | 98 | 169.5 | 188 | yes | yes | Stable | 16.8 | | 592 |
| 72 h | 90 | 100 | 133 | 148 | yes | no | Stable | | | |
| d4 | 90 | 97 | | 107 | yes | no | Stable | | | |
| d5 | 90 | 98 | | 124 | yes | yes | Stable | 5.4 | | 686 |
| d6 | 90 | 96 | | 95 | | yes | Worse | 8.8 | | 687 |

| Patient 2 | FiO2 | sO2 | pO2 | PaO2/FiO2 | NIV | fever | Worse/Improved | CRP mg/dL | IL-6 | LDH |
|---|---|---|---|---|---|---|---|---|---|---|
| Screening | 90 | 96 | 112 | 124 | | yes - 7 d | N/A | | | |
| Baseline | 90 | 99 | 150 | 167 | yes | yes | N/A | 18.6 | 22.6 | 471 |
| 24 h | 90 | 100 | | 167 | yes | no | Stable | 5.3 | 15.3 | |
| 48 h | 90 | 100 | | 167 | yes | no | Stable | | | |
| 72 h | 60 | 100 | | 250 | yes | no | Improved | 3.26 | | 290 |
| d4 | 50 | 99 | | 290 | yes | no | Improved | 1.27 | | 254 |
| d5 | 50 | 100 | | 290 | yes | | Improved | | | |

| | FiO2 | sO2 (%) | pO2 (torr) | PaO2/FiO2 | NIV | fever | Worse/Improved | CRP mg/dL | IL-6 | LDH |
|---|---|---|---|---|---|---|---|---|---|---|
| Patient 3 | | | | | | | | | | |
| Screening | 24 | 98 | 60.4 | 252 | | yes - 9 d | N/A | | | |
| Baseline | 40 | 96 | | 215 | no | yes | N/A | 10 | | 374 |
| 24 h | 35 | 98 | | 329 | no | no | Improved | 9.7 | | 340 |
| 48 h | 31 | 99 | | 467 | no | no | Improved | | | |
| 72 h | 28 | 98 | | 400 | | no | Improved | 8.5 | | 281 |
| d4 | 28 | 98 | | 400 | | no | Stable | | | |
| d5 | 21 | 98 | | 533 | | | Discharged | | | |
| Patient 4 | | | | | | | | | | |
| Screening | 21 | 95 | 58 | 276 | | yes - 10 d | N/A | | | |
| Baseline | 40 | 94 | 73 | 182 | no | yes | N/A | 14.3 | | 377 |
| 24 h | 31 | 95 | | 254 | no | no | Improved | 13.9 | | 336 |
| 48 h | 31 | 95 | | 254 | | no | Stable | | | |

TABLE 2-continued

Efficacy of the anti-GM-CSFRa antibody in treating COVID-19 for 6 patients

| | | | | | | | | | | |
|---|---|---|---|---|---|---|---|---|---|---|
| 72 h | 31 | 96 | | 277 | no | | Stable | 13.6 | | 312 |
| d4 | 31 | 96 | | 277 | no | | Stable | | | |
| d5 | 28 | 96 | | 307 | no | | Improved | | | |
| Patient 5 | | | | | | | | | | |
| Screening | 21 | 98 | 62.5 | 297 | | yes - 1 d | N/A | | | |
| Baseline | 40 | 96 | 86 | 215 | no | yes | N/A | 14.6 | 44.6 | 420 |
| 24 h | 31 | 95 | | 255 | no | no | Improved | 11.7 | 12.2 | 437 |
| 48 h | 28 | 95 | | 282 | no | no | Improved | 7.4 | | 380 |
| 72 h | 24 | 96 | | 358 | no | no | Improved | | | |
| d4 | 21 | 95 | | 376 | no | no | Discharged | | | |
| d5 | | | | | | | | | | |
| Patient 6 | | | | | | | | | | |
| Screening | 21 | 93 | 63.3 | 201 | | yes - 7 d | N/A | | | |
| Baseline | 90 | 93 | 176 | 195 | yes | yes | N/A | 17.7 | | 944 |
| 24 h | 90 | 97 | 102 | 113 | yes | no | stable | 9.1 | | 838 |
| 48 h | 90 | 95 | | 88 | yes | no | stable | | | |
| 72 h | 60 | 96 | | 143 | yes | no | stable | 7.4 | | 682 |
| d4 | 60 | 97 | | 160 | yes | no | stable | | | |
| d5 | | | | | | | | | | |

Normal ranges for LDH: 125-220
CRP Reference levels:
    Range
        Normal: 0.5 mg/dL
        Mild: ~1-5 mg/dL
        Moderate: ~5-9 mg/dL
        Severe: >9 mg/dL
    Sepsis: 15.2±8.2 mg/dL
    Severe sepsis: 20.3±10.9 mg/dL
    Septic shock: 23.3±8.7 mg/d
IL-6 Reference level:
    Normal: <7
    Inflammation: >40
FiO2 Reference Level
    Normal: ~21
    Mild: ~22-50
    Moderate: ~50-80
    Severe: >~80
SO2 Reference Level
    Normal: >~93
PO2 Reference Level
    Normal: >~90
    Mild: ~70-~90
    Severe: <~70

ARDS Severity for PaO/FiO2 ratio (Mortality %)
    Mild: 200-300 (27%)
    Moderate: 100-200 (32%)
    Severe: <100 (45%)
    NIV=Non-invasive ventilation
Fever column: "#d" represents the number of days that the subject had a fever at the time of initial screening.

As shown in Table 2, the anti-GM-CSFRα antibody was effective in improve COVID-19 associated symptoms. Administration of the anti-GM-CSFRα antibody was able to reduce incidence of progression of acute respiratory failure, the need of mechanical ventilation.

In addition, the clinical data from 26 patients in an age-matched contemporaneous historical cohort who were treated with the same standard of care was provided for comparison. In general, these two cohorts were comparable in age. The majority of controls were males (17 [65%]) with fever (21 [80.8%], duration of fever 7 [5-10] days) and the most common comorbidity was systemic arterial hypertension in 10 patients (38.4%). Demographics and clinical characteristics of patients are summarized in Table 3. No patients were on mechanical ventilation at baseline. Duration of follow-up ranges from 4 days to fourteen days.

TABLE 3

Demographic and baseline clinical characteristics of patients treated with anti-GM-CSFRα antibody and controls.

| | anti-GM-CSFRα (n = 13) | Controls (n = 26) | p |
|---|---|---|---|
| Age (years), median (IQR) | 57 (51.5-58.5) | 59.5 (52.7-67.7) | P = 0.187 |
| Males, n (%) | 12 (92) | 17 (65) | P = 0.120 |
| P/F ratio, median (IQR) | 195.5 (163.8-219.5) | 216.5 (134.6-258.3) | P = 0.607 |
| Patients (n[%]) with p/f 200-300 | 6 (46) | 14 (54) | P = 0.741 |
| p/f 100-200 | 6 (46) | 9 (35) | P = 0.508 |
| p/f <100 | 1 (8) | 3 (11) | P = 0.999 |
| Patients on NIV, n (%)* | 3 (23) | 6 (23) | P = 0.999 |
| High-flow oxygen, n (%)* | 6 (46) | 10 (38) | P = 0.736 |
| Low-flow oxygen, n (%)** | 4 (31) | 10 (38) | P = 0.728 |
| Patients with fever, n (%) | 11 (85%) | 18 (69%) | P = 0.445 |

TABLE 3-continued

Demographic and baseline clinical characteristics of patients treated with anti-GM-CSFRα antibody and controls.

|  | anti-GM-CSFRα (n = 13) | Controls (n = 26) | p |
|---|---|---|---|
| Fever duration (days), median (IQR) | 11 (9.5-12.5) | 7 (5.0-10.0) | P = 0.006 |
| CRP (mg/L), median (IQR) | 152.4 (95.8-181.5) | 123.3 (76.5-190.2) | P = 0.758 |
| LDH (U/L), median (IQR) | 420 (376-537) | 467 (349-527) | P = 0.713 |
| Ferritin (ng/ml), median (IQR) | 2302.0 (926.0-3325.72) | 1269.0 (809.5-3617.5) | P = 0.749 |

N = number; IQR = interquartile range; P/F ratio: ratio of the partial pressure of oxygen ($Pao_2$) to the fraction of inspired oxygen ($Fio_2$); NIV = non-invasive ventilation with continuous positive airway pressure; CRP = C-reactive protein serum levels; LDH = lactate dehydrogenase;
*corresponding to a category of 5 on the 7-point ordinal scale;
**corresponding to a category of 4 on the 7-point ordinal scale.

Figure 2:
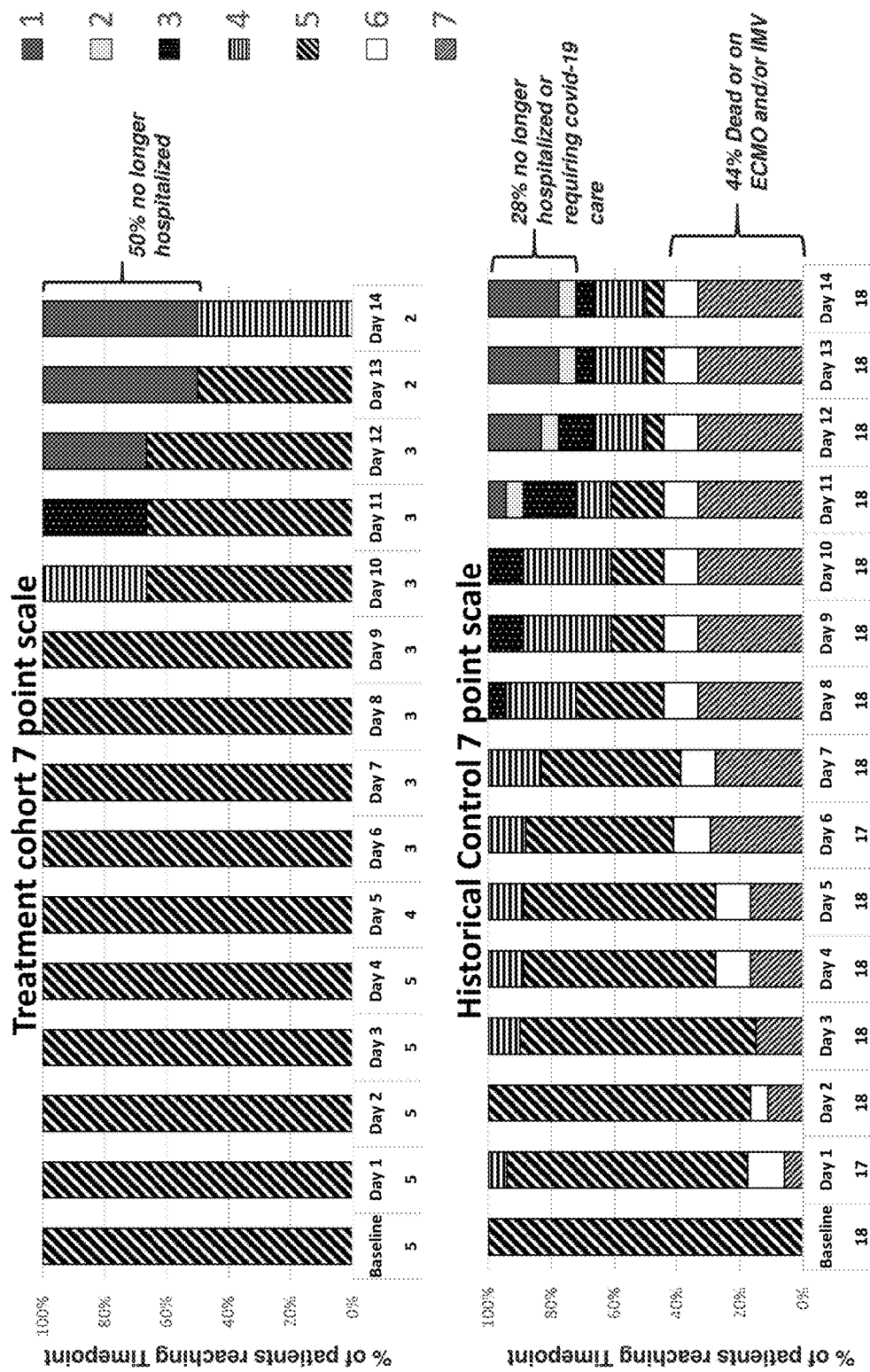
FIG. 2 is an exemplary bar graph illustrating the seven point scale over time for patients in category 5—i.e., hospitalized patients with varying degrees of need for non-invasive oxygen therapy, who are at risk for rapid clinical deterioration. The top panel shows progression over time for the treated cohort, and the bottom panel shows progression over time for the historical control group. The seven point scale is: 1. Patient discharged from the hospital; 2. Hospitalized, not requiring supplemental oxygen, no longer requiring ongoing medical care for COVID-19; 3. Hospitalization, not requiring supplemental oxygen, requiring ongoing medical care (COVID-19 related or otherwise); 4. Hospitalization requiring supplemental low-flow oxygen therapy (O2 concentration 35% or below); 5. Hospitalization, requiring nasal high-flow oxygen therapy ($O_2$ concentration 40% or above), non-invasive mechanical ventilation, or both; 6. Hospitalization requiring invasive mechanical ventilation; 7. Death. For patients who were no longer hospitalized or requiring on-going medical care (score 1 or 2), last known score was carried forward assuming they will not be re-hospitalized. For patients who were scored 6 or 7, last known score was carried forward as patient had already died and/or progressed to invasive mechanical ventilation. 50% of the treated group was no longer hospitalized or required COVID-19 care at day 14. For historical control group, 28% was no longer hospitalized required COVID-19 care, and 44% of the patients died or was on ECMO and/or IVM at day 14.
Figure 3:
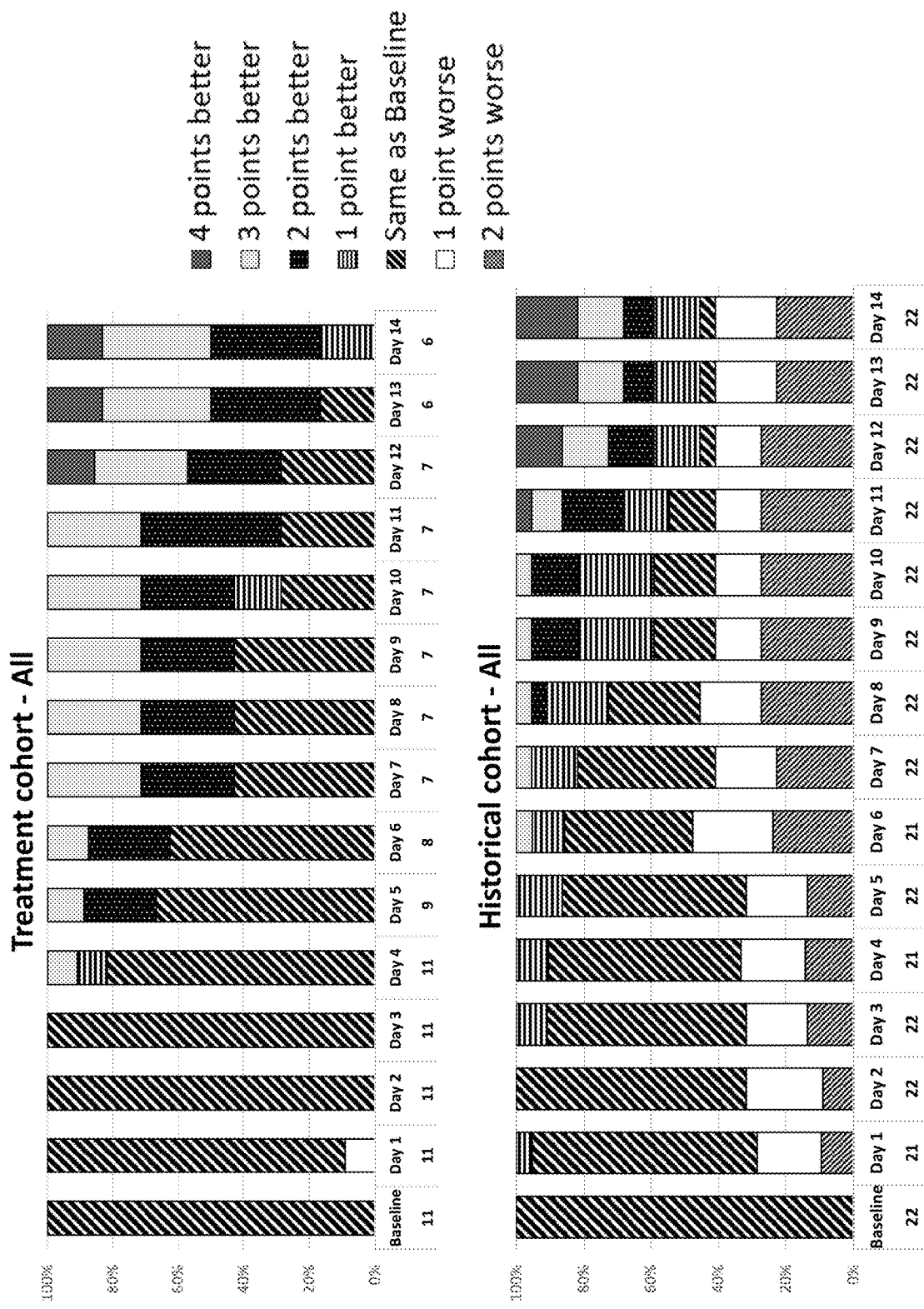
FIG. 3 is an exemplary bar graph illustrating progression over time for all patients in all categories in terms of 7-category ordinal scale. The top panel shows progression over time for the treated cohort, and the bottom panel shows progression over time for the historical control group. The treated cohort shifts away from baseline, showing better progression over time (decrease in point in the ordinal scale), whereas the historical control group progresses towards more severe (worst) condition (increase in point in the ordinal scale).
Figure 4:
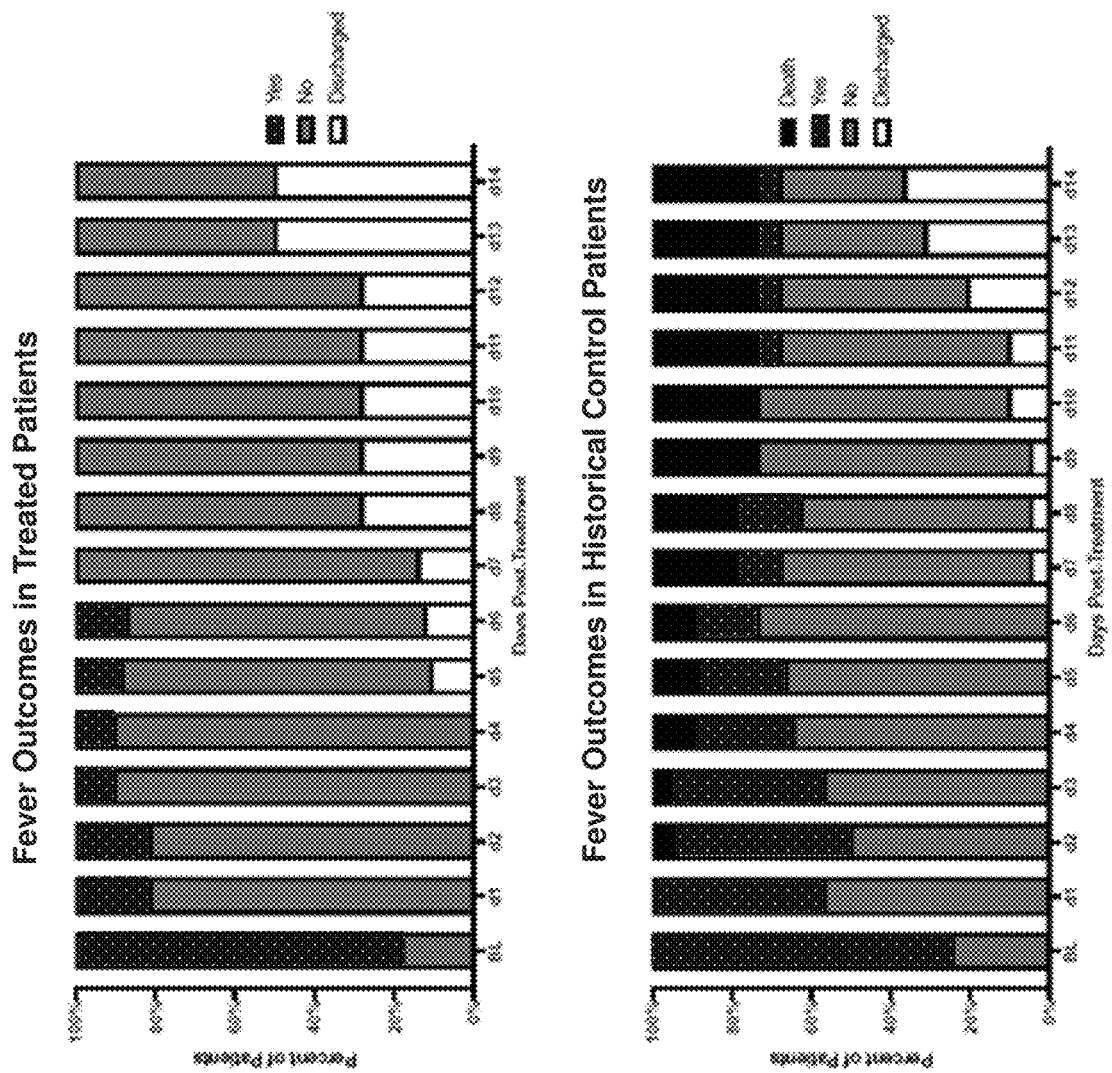
FIG. 4 is an exemplary bar graph illustrating progression over time for all patients in all categories in terms of fever resolution. The left panel shows fever outcome over time for the treated cohort, and the right panel shows fever outcome over time for the historical control group. The treated cohort shows fever resolution within a few days ("No") with about half of the patients being discharged at day 14.
Figure 5:
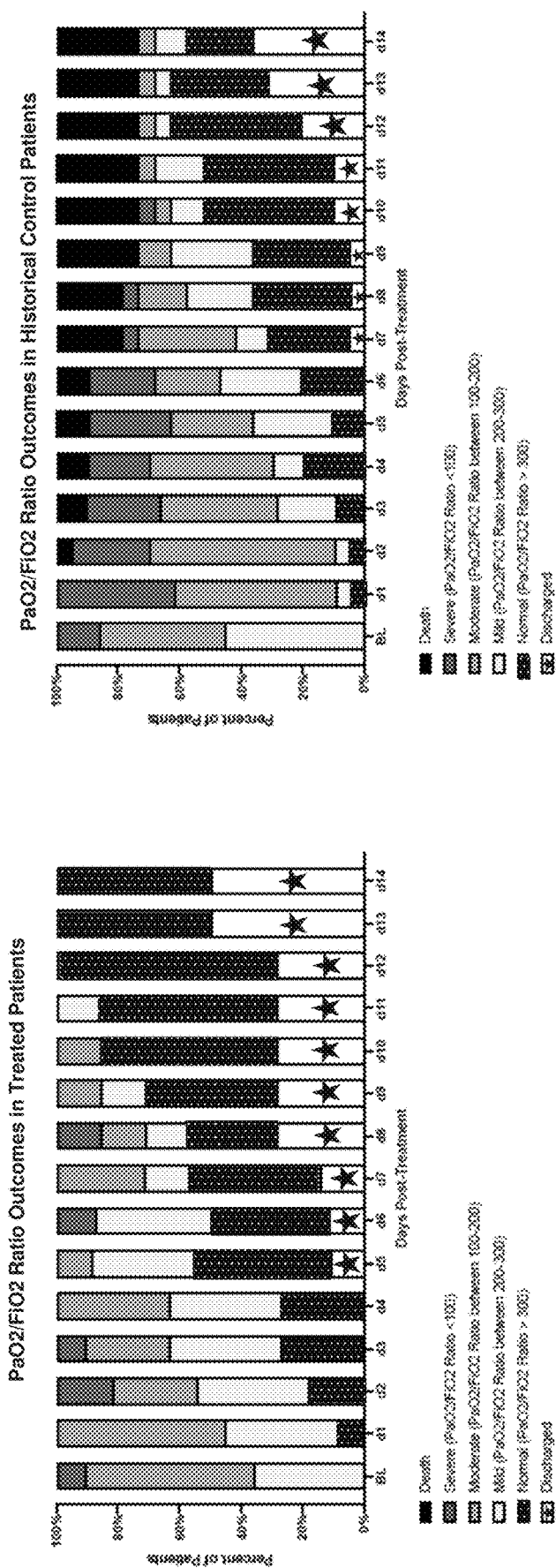
FIG. 5 is an exemplary bar graph illustrating progression over time for all patients in all categories in terms of improvement in $PaO_2/FiO_2$ ratio. The left panel shows $PaO_2/FiO_2$ ratio over time for the treated cohort, and the right panel shows $PaO_2/FiO_2$ ratio over time for the historical control group. The treated cohort shows improvement in $PaO_2/FiO_2$ ratio over time.

The preliminary results observed in the study appear to support a clinical benefit vs historical controls as assessed by several clinical endpoints. The clinical benefits include:
  No deaths (0%) were reported in all 13 patients receiving anti-GM-CSFRα antibody at 6 mg/kg dose vs 7 (27%) deaths of the 26 patients in the control group.
  Only one patient (9.1%) of the 13 patients in treated non-ventilated cohort, who were non-ventilated at baseline, started mechanical ventilation on Day 13 post dose. This patient was clinically stable while on observation and non-ventilated. The decision to start ventilatory support was not driven necessarily by a worsening of the patient's clinical status. The patient had been in severe respiratory distress at baseline (time of dosing) and therefore was a candidate for mechanical ventilation at that time; however, there were no mechanical ventilators available. In the post-treatment follow up, the patient remained stable on facemask $O_2$ and cycled non-invasive ventilatory support, with apparent improving oxygenation and decreasing oxygen requirement; however, when a ventilator and ICU bed became available on Day 13 post dose, the patient was electively intubated to provide more effective PEEP. The patient continues to improve in clinical course.
  There were apparent improvements in anti-GM-CSFRα antibody-treated patients vs. historical controls in terms of clinical progression, as assessed by a commonly used 7-point ordinal scale.
    1. Patient discharged from the hospital;
    2. Hospitalized, not requiring supplemental oxygen, no longer requiring ongoing medical care for COVID-19;
    3. Hospitalization, not requiring supplemental oxygen, requiring ongoing medical care (COVID-19 related or otherwise);
    4. Hospitalization requiring supplemental low-flow oxygen therapy (O2 concentration 35% or below);
    5. Hospitalization, requiring nasal high-flow oxygen therapy (O2 concentration 40% or above), non-invasive mechanical ventilation, or both;
    6. Hospitalization requiring invasive mechanical ventilation;
    7. Death.
  The clinical improvement was defined as improvement ≥2 categories on the 7-point ordinal scale for clinical assessment. The primary end-point was progression to a point of 1 or 2 on the seven-category ordinal scale Other clinical secondary end-points included: the percentage of patients reaching 1 or 2 point on the same scale, the percentage of patients without fever at the end of follow-up and time to resolution of fever without need for antipyretics for at least 48 hours; overall survival and mechanical-ventilation free survival; serum CRP.
  This scale tracks clinical progression across a wide spectrum from Patient discharged from the hospital (best) to Hospitalization with/without need for oxygen and through to Death (worst). On this 7-point ordinal scale it is noted that:
    Apparent trends confirming lack of progression to ventilation or death vs. notable progression in the historical cohort (FIG. 1); this was true also when only patient in Category 5 are considered, i.e.: hospitalized patients with varying degrees of need for non-invasive oxygen therapy, who are at risk for rapid clinical deterioration (FIG. 2)
    Apparent trends confirming better outcomes for anti-GM-CSFRα antibody-treated patients vs historical controls, in terms of supplemental-oxygen-free survival (as assessed by progression towards more severe (worst) for controls vs. shifts away (better) from baseline for anti-GM-CSFRα antibody cohort) (FIG. 3);
    Support from data on fever resolution (FIG. 4) and improvement in $PaO_2/FiO_2$ ratio (FIG. 5) over time.

Safety

Overall, anti-GM-CSFRα antibody has been well-tolerated with no drug-related SAEs. One patient, a 75-year-old Caucasian male who was on mechanical ventilation in the ICU since 30 Mar. 2020 for severe COVID-19 pneumonia, received anti-GM-CSFRα antibody on 31 Mar. 2020. Concomitant medications were hydroxychloroquine and darunavir. He was diagnosed with bacterial sepsis based on blood cultures drawn 2 days after receiving the anti-GM-CSFRα antibody. Briefly, the baseline, pre-infusion level of C-reactive protein was 2.1 mg/dL, which remained stable at 1.9 mg/dL at the following testing (about 5 hours after anti-GM-CSFRα antibody infusion). At hour 34 after anti-GM-CSFRα antibody administration (morning of 2 Apr. 2020), the C-reactive protein (CRP) was 1.6 mg/dL. On that same day (in the afternoon), the patient experienced a slight deterioration of respiratory function. An infection was suspected, and blood cultures were drawn.

On the following morning of 3 Apr. 2020, (58 hours after anti-GM-CSFRα antibody administration) the CRP increased to 9.5 mg/dL with a procalcitonin level of 1.5 ng/L (NR<0.5 ng/L). Empiric treatment with linezolid was initiated pending the results of blood cultures. On the following day (4 Apr. 2020), four days after anti-GM-CSFRα antibody administration, the blood cultures turned positive for Gram positive cocci (initially interpreted at light microscopy as possible Staphylococci). At the same time, a single blood culture (out of 3 drawn on admission on 30 Mar. 2020 for microbiological screening (note: the patient was transferred from another institution) turned positive for *Corynebacterium* spp. This finding was considered irrelevant and the bacterium a possible contaminant since the patient didn't show any sign of infection at the time of blood culture withdrawal (30 Mar. 2020). Also, linezolid would have covered this infection, so no further action was taken, and linezolid treatment was continued. At that time (4 Apr. 2020), the CRP was 23.3 mg/dL. As of 5 Apr. 2020, the patient was improving, and the CRP fell to below 20 mg/dL, and he was not showing other symptoms. On 6 Apr. 2020, the definitive microbiological identification become available, indicating *Streptococcus constellatum* as the infectious agent. The CRP of the patient remains stable and an infectious disease consultation has been asked to evaluate if a change in the antibiotic treatment is needed. An echocardiogram has been requested.

It was concluded that in this patient, who transferred from another institution, the initiation of positive end-expiratory pressure (PEEP) may have brought out the bacteremia. The timing of the positive blood culture (44 hours post infusion) makes it poorly credible that the recent immunosuppressive treatment with anti-GM-CSFRα antibody was the risk factor for the infection. The investigator contrasted this timeline with other monoclonal antibodies used in COVID-19 (tocilizumab/sarilumab), in which secondary bacteremia had been seen typically after 1015 days. The patient is now responding to the antibiotics. The investigator independently assessed the event of bacterial sepsis as not related to anti-GM-CSFRα antibody.

Conclusion and Statistical Analysis

Patients treated with anti-GM-CSFRα antibody responded apparently faster and better than in the historical control or real-world evidence group, as measured by the endpoints described above. During a 28-days follow-up, no patient treated with anti-GM-CSFRα antibody (0%) and 7 patients in the control group died. All deaths occurred in patients with severe respiratory failure, defined as a score higher than 4 on the 7-category ordinal scale (p=0.023); 6 out of 7 deaths occurred during the first week of follow-up, and the remaining one on day 8. At 28 days of follow up, 100% of the anti-GM-CSFRα antibody-treated patients (n=13) and 65% (n=17) of untreated comparing patients attained a clinical improvement ≥2 points on the 7-category ordinal scale (p=0.018) and were discharged from the hospital. One patient treated with the anti-GM-CSFRα antibody (8%) progressed to mechanical ventilation, compared to 9 patients in the comparison group (35%) (p=0.120). Notably, the ventilated patient in the treated group weaned off from mechanical ventilation and no longer required supplemental oxygen. This is significant when put in perspective with the control group in which, at 28 days of follow up, none of the patients who progressed to mechanical ventilation recovered, and either died or continued to receive mechanical ventilation. Moreover, at 14 days of follow up, 72.6% of treated patients reached the primary end-point (point 1 or 2 based on the 7-point ordinal scale) whereas only 42.3% of the control patients reached the primary end-point.

Considering the whole cohort of 13 cases and 26 controls, patients treated with anti-GM-CSFRα antibody needed a significant lower number of days to satisfy the primary end-point compared to controls (7.0 [5.0-13.0] days vs 14.0 [11.7-14.0] days) (p=0.001). The time to primary end-point was assessed after all patients had reached day 14, with failure to reach the end-point or mechanical ventilation or death before day 14 considered as right-censored at day 14 (right-censoring occurs when an event may have occurred after the last time a person was under observation, but the specific timing of the event is unknown). The time to primary end-point was portrayed by Kaplan-Meier plot and compared with a log-rank test. Similarly, time to fever disappearance was portrayed by Kaplan-Meier plot and compared with a log-rank test. Univariate survival analysis considering a composite end-point of death or need for mechanic ventilation was performed using the Kaplan Meier approach and with log-rank test. Statistical significance was defined as a p-value <0.05.

Figure 6:
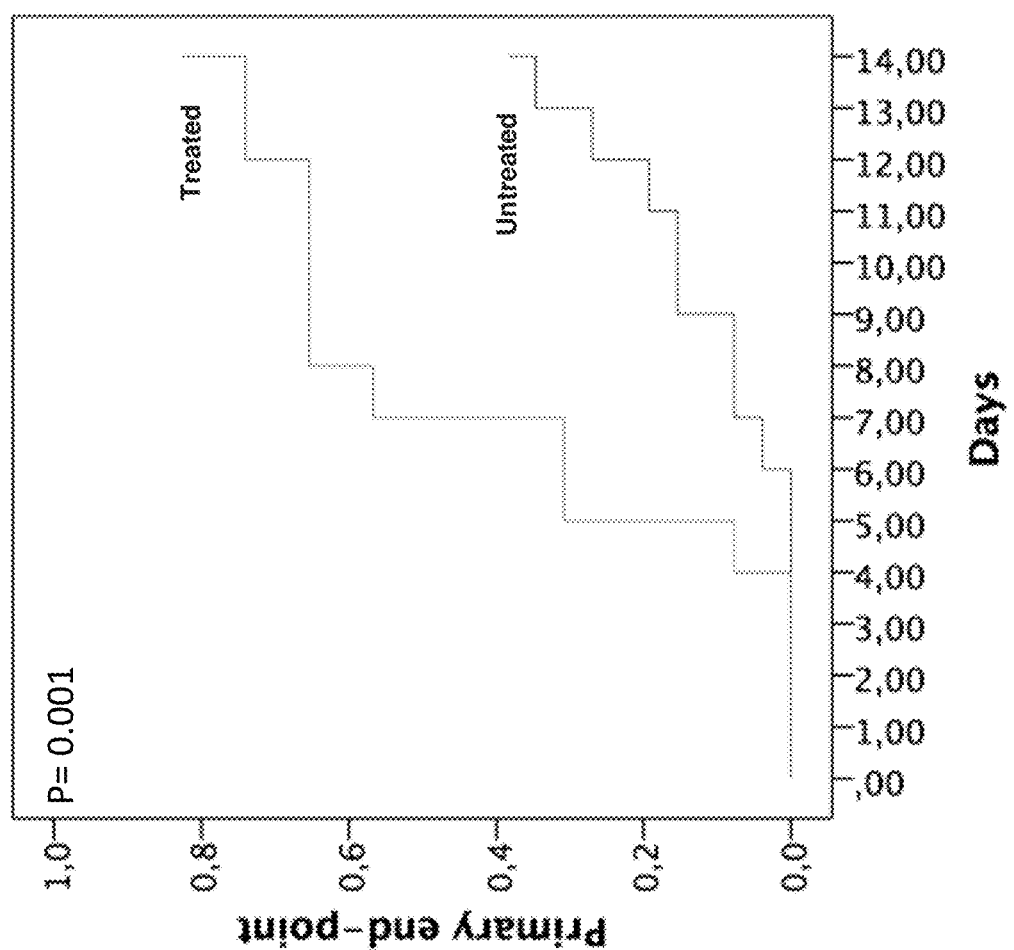
FIG. 6 is an exemplary Kaplan-Meier plot for the time to primary end-point compared with a log-rank test. The time to primary end-point (point 1 or 2 on 7-point ordinal scale) was significantly shorter in patients treated with anti-GM-CSFRα antibody compared to controls using the Kaplan-Meier plot and compared with a log-rank test ($\chi 2=11.8$, p=0.001). A higher number of patients treated with anti-GM-CSFRα antibody satisfied the primary end-points compared to untreated patients.

The time to primary end-point was significantly shorter in patients treated with anti-GM-CSFRα antibody compared to controls, using the Kaplan-Meier plot and compared with a log-rank test ($\chi2$=11.8, p=0.001) (FIG. 6). Moreover, a higher number of patients treated with anti-GM-CSFRα antibody satisfied the primary end-points compared to untreated patients (10 [76.2%] vs 11 [42.3%]) (p=0.041). The difference in days to primary end-point remained significant even after exclusion of patients who died or were admitted to ICU (7.0 [5.0-11.0] days for patients treated with anti-GM-CSFRα antibody vs 12.0 [10.0-14.0] for controls) (p=0.004).

Figure 7:
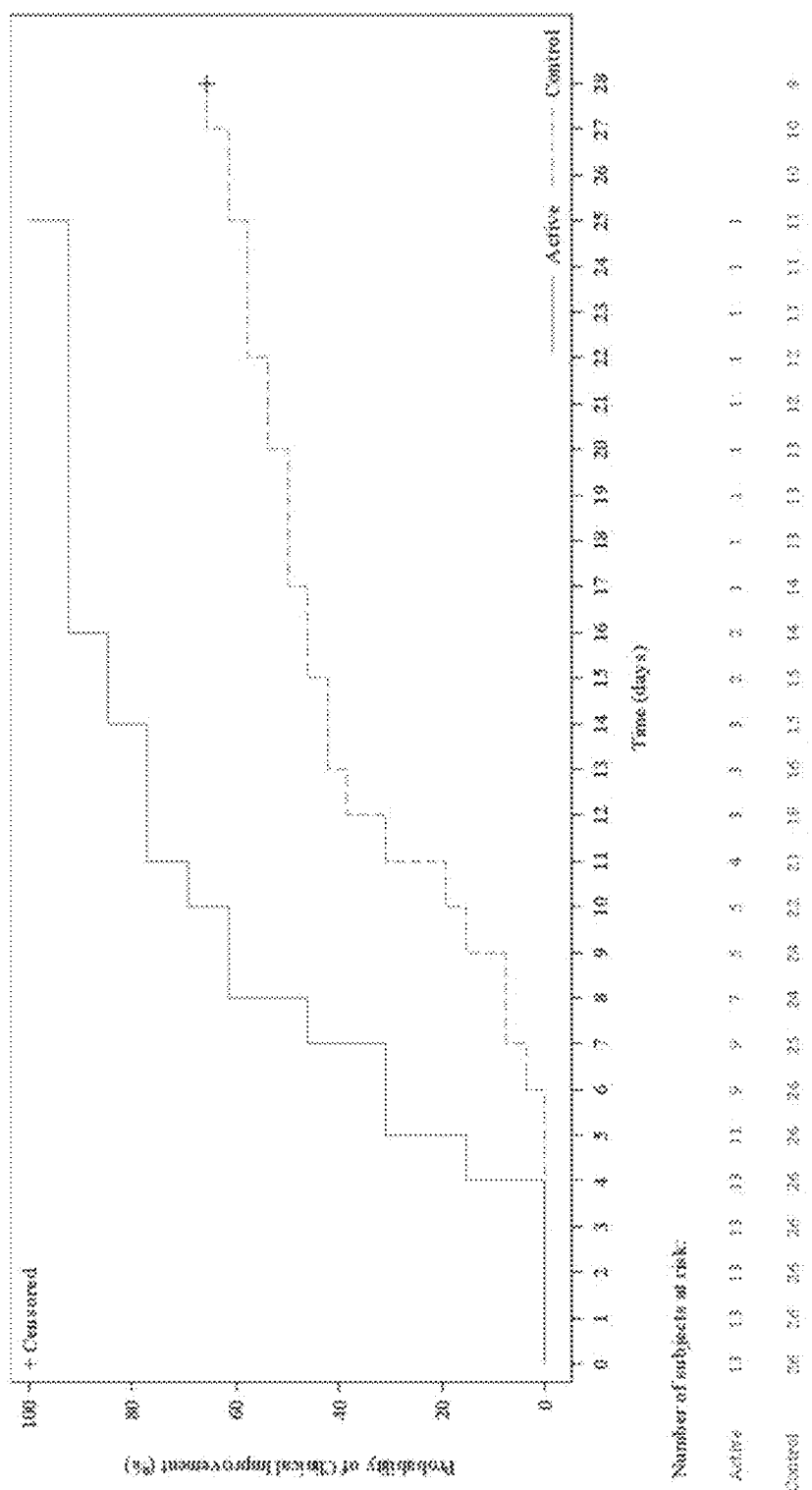
FIG. 7 is an exemplary Kaplan-Meier plot for time to clinical improvement as compared with a log-rank test ($\chi 2=14.59$, p≤0.001). The plot illustrates that patients treated with anti-GM-CSFRα antibody reached the clinical improvement (improvement ≥2 points on a 7-point ordinal scale) in fewer days compared to untreated patients (8.0 [5.0-11.0] days vs 18.5 [11.0-NE] (NE=non-estimable) days. At day 28, 13 anti-GM-CSFRα antibody-treated patients (100%) and 13 (65%) untreated patients obtained a clinical improvement (p=0.018).

The time to clinical improvement was assessed after all patients had reached day 28. Notably, patients treated with anti-GM-CSFRα antibody reached the clinical improvement in significantly fewer days compared to the comparison group (8.0 [5.0-11.0] vs 18.5 [11.0-NE]; NE: non-estimable), as demonstrated by the Kaplan-Meier plot and compared with a log-rank test ($\chi2$=14.59, p≤0.001) (FIG. 7). Accordingly, anti-GM-CSFRα antibody treatment was associated with earlier discharge from hospital (8.0 [5.0-11.0] vs 18.5 [11.0-NE]).

Figure 8:
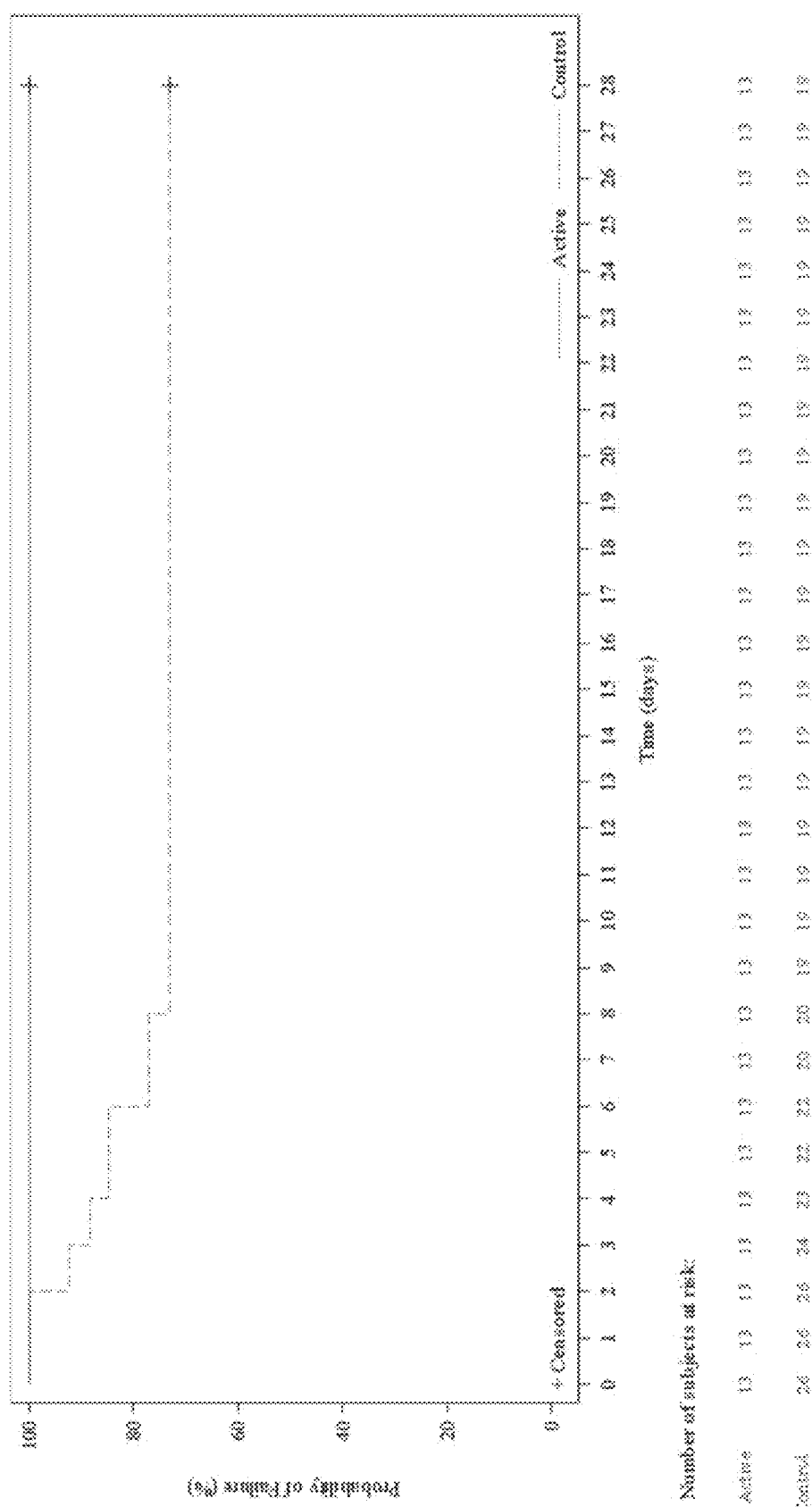
FIG. 8 is an exemplary Kaplan-Meier plot for survival. Cumulative survival estimated by Kaplan-Meier curve at 28 days of patients treated with anti-GM-CSFRα antibody and of the untreated control group ($\chi 2=4.0$, p=0.046). No anti-GM-CSFRα antibody-treated patients and 7 patients of the untreated group (27%) died during follow-up.

During the 28-day follow-up period, no anti-GM-CSFRα antibody-treated patients (0%) and 7 patients of the comparison group (27%) died ($\chi2$=4.0, p=0.046) (FIG. 8). All deaths occurred in patients with severe respiratory failure, defined as a score higher than 4 on the 7-category ordinal scale (p=0.023).

Figure 9:
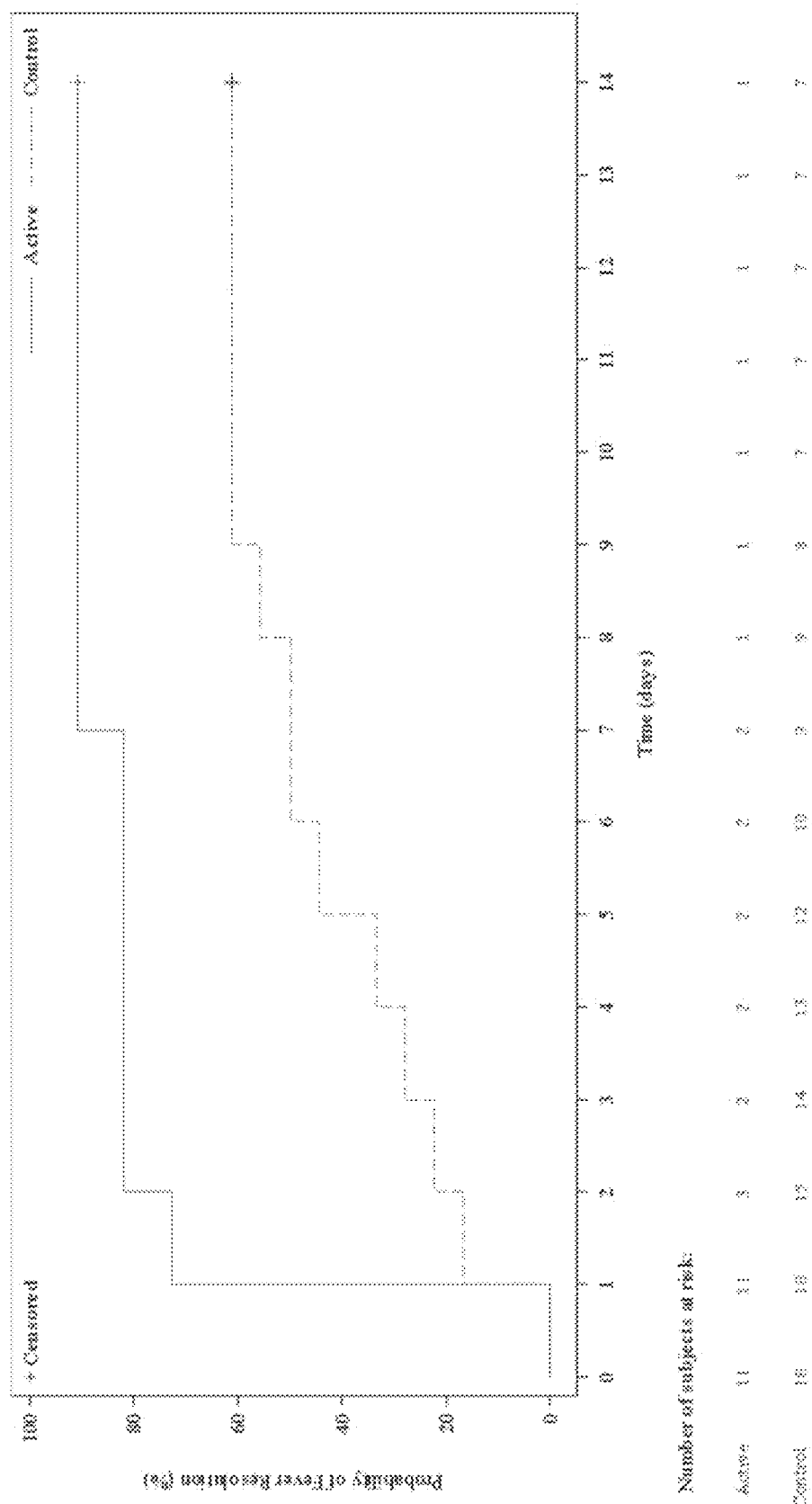
FIG. 9 is an exemplary Kaplan-Meier plot for time to fever resolution compared with a log-rank test ($\chi 2=6.75$, p=0.009) showing a shorter time to resolution of fever in patients treated with anti-GM-CSFRα antibody (active) compared to comparison group (control) (1.0 [1.0-2.0] days vs 7.0 [3.0-NE] (NE=non-estimable) days). Fever resolved in 91% patients treated with mavrilimumab who were febrile at baseline, compared to 61% in the comparison cohort who were febrile at baseline.

Fever resolved in 91% (n=10 out of 11 febrile patients) of patients treated with anti-GM-CSFRα, compared to 61% (n=11 out of 18 febrile patients) in the comparison cohort (p=0.202); time to resolution of fever was significantly shorter in mavrilimumab-treated patients than the comparison group (1.0 [1.0-2.0] days vs 7.0 [3.0-NE] days, respectively, $\chi2$=6.75, p=0.009) (FIG. 9). Patients treated with anti-GM-CSFRα antibody, however, showed a significantly longer duration of fever before hospitalization compared to controls (11.0 [9.5-12.5] vs 7.0 [5.0-10.0]), p=0.006) that could potentially affect this result.

Figure 10:
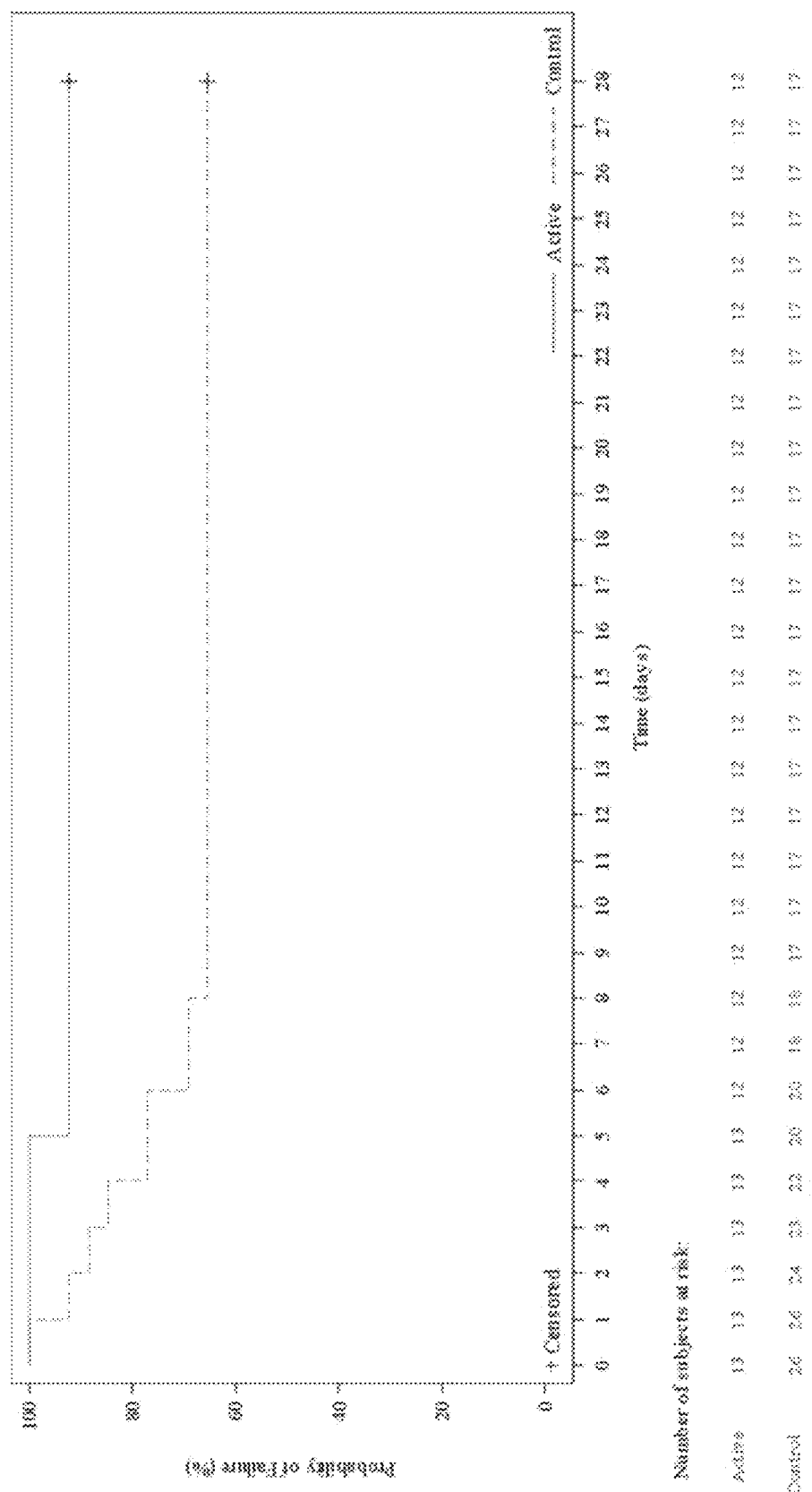
FIG. 10 is an exemplary Kaplan-Meier plot for mechanical ventilation-free survival and comparison with a log-rank test. Considering the secondary composite end-point of death and mechanical ventilation, no statistically significant differences emerged between treated and untreated patients, probably due to the low number of patients and the low rate of events ($\chi 2=3.12$, p=0.077).

Considering the secondary composite end-point of death and mechanical ventilation, no differences emerged between treated and untreated patients, probably due to the low number of patients and the low rate of events (FIG. 10) ($\chi2$=3.12, p=0.077).

Figure 11:
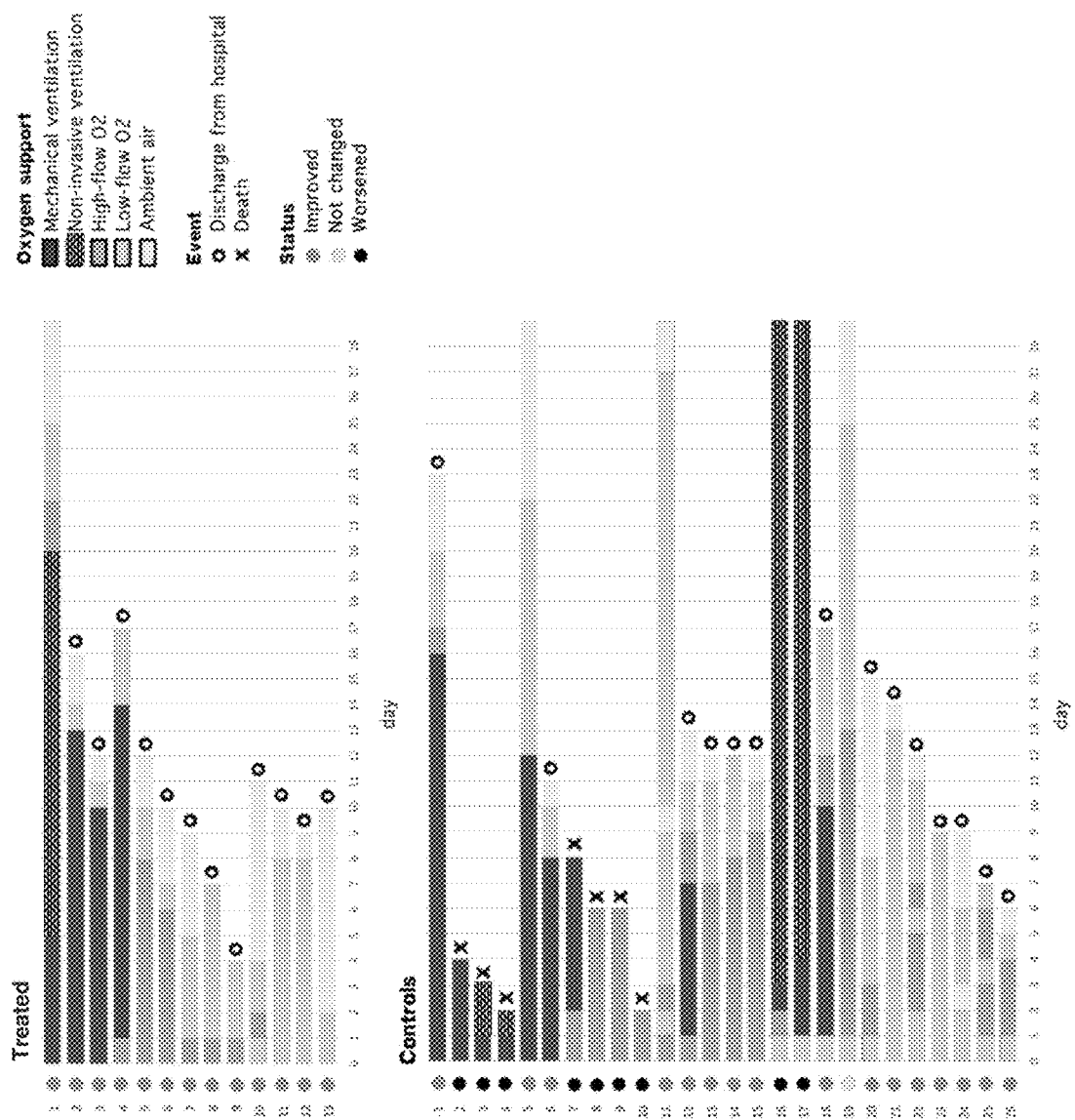
FIG. 11 is an exemplary graphs showing changes in clinical status and oxygen-support from baseline in individual patients for 28 days. Baseline (day 0) was the day on which treatment with anti-GM-CSFRα antibody was started for patients, and the day of first fulfillment of eligibility criteria for controls. For each patient, the shades in the line represent the oxygen-support status of the patient over time. The circles at the end of a line indicates the patient's overall change in status from baseline. A patient's status "improved" if the oxygen-support status improved by at least two points on a 7-point scale before day 28, or the patient was discharged. The blank circles at the end of a line indicates "patient discharged from the hospital". The cross at the end of a line indicates that the patient died.

The follow-up data of patients treated with anti-GM-CSFRα antibody (at day 28, unless indicated otherwise) are summarized in Table 4, and individual patient's changes in clinical status are shown in FIG. 11.

TABLE 4

Follow-up data of patients treated with anti-GM-CSFRα antibody and controls.

| | anti-GM-CSFRα (n = 13) | Controls (n = 26) | p |
|---|---|---|---|
| #Primary end-point*, n (%) | 10 (76.2) | 11 (42.3) | P = 0.041 |
| #Days to primary end-point, median (IQR) | 7.0 (5.0-13.0) | 14.0 (11.7-14.0) | P = 0.001 |
| #Days to primary end-point, mean ± SD§ | 7.0 (5.0-11.0) | 12.0 (10.0-14.0) | P = 0.004 |
| Clinical improvement*, n (%) | 13 (100) | 17 (65) | P = 0.018 |
| Days to clinical improvement, median (IQR) | 8.0 (5.0-11.0) | 18.5 (11.0-NE) | P ≤ 0.001 |
| Days to clinical improvement, median (IQR)§ | 8.0 (5.0-11.0) | 18.5 (11.0-NE) | P ≤ 0.001 |
| Days to resolution of fever in the first 2 weeks, median (IQR) | 1.0 (1.0-2.0) | 7.0 (3.0-NE) | P = 0.009 |
| Fever resolution by day 14, n (%)$^a$ | 10 (91)$^a$ | 11 (61)$^a$ | P = 0.110 |
| Mechanical ventilation, n (%) | 1 (8) | 9 (35) | P = 0.12 |
| Death, n (%) | 0 (0) | 7 (27) | P = 0.07 |
| CRP reduction ≥ 75%, n (%) | 11 (85) | 11 (44) | P = .0.036 |

Figure 12:
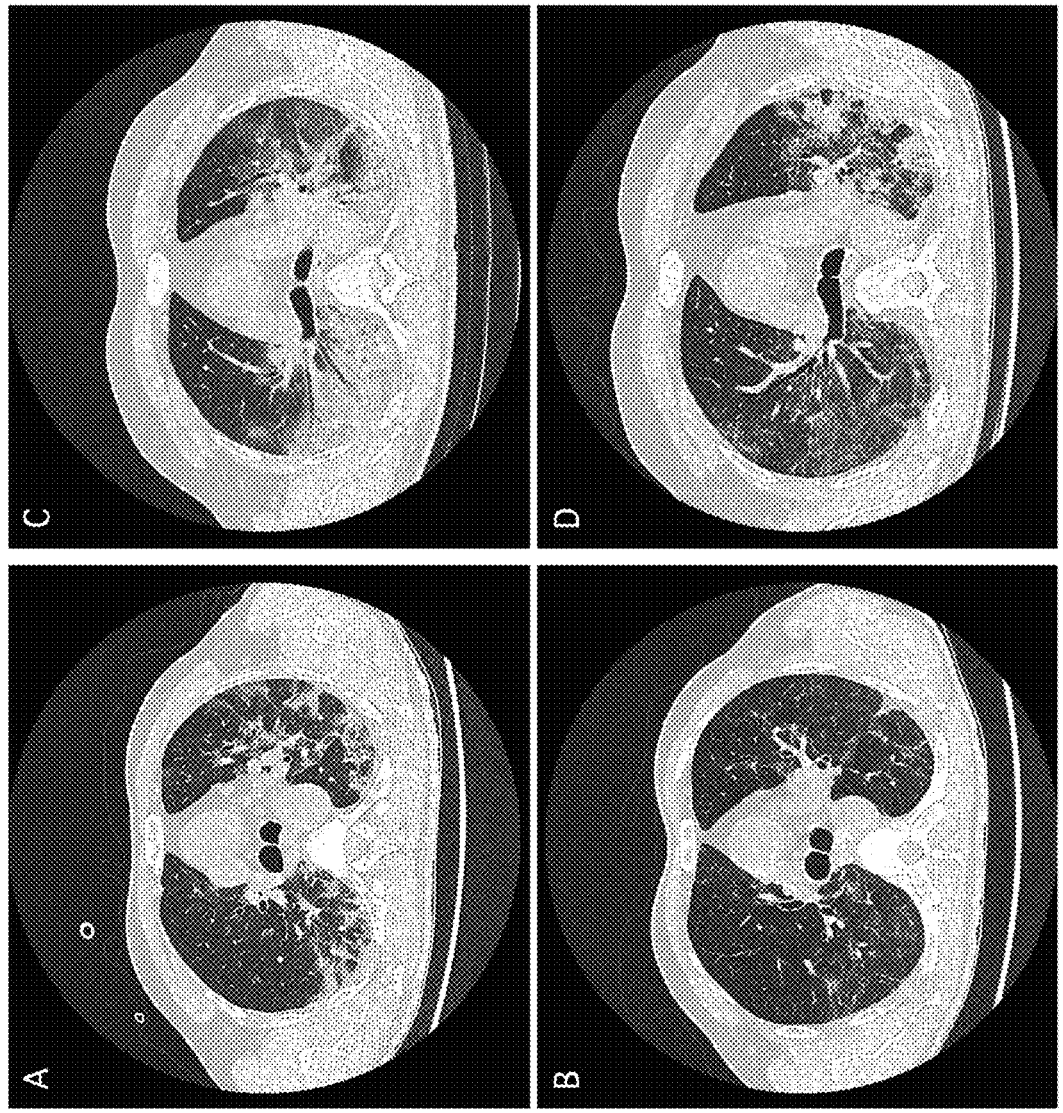
FIG. 12 is an exemplary lung CT scans of two patients at baseline, and after treatment with anti-GM-CSFRα antibody.

N = number; NE = non-estimable IQR = interquartile range; the primary end point is progression to point or 1 or 2 on the seven-category ordinal scale;
*clinical improvement defined by live discharge from the hospital, a decrease of at least 2 points from baseline on a modified ordinal scale (as recommended by the WHO R&D Blueprint Group), or both;
§after exclusion of patients who died or were admitted to ICU and are still in ICU;
$^a$fever resolution calculated on febrile patients, i.e. 11 patients treated with anti-GM-CSFRα antibody and 18 patients of the comparison group;
results at 14 days follow-up Radiological Findings As part of the monitoring of patients with pneumonia, regular CT scans were performed on all patients to assess radiological evolution of the disease. Imaging obtained at baseline and discharge for 2 representative patients treated with anti-GM-CSFRα antibody tended to show significant improvement in lung opacification (FIG. 12), consistent with the overall improvement in their clinical status. The lung CT scan of Patient 1 performed at baseline showed presence of bilateral, blurred ground glass opacities with crazy paving pattern and small dense consolidation areas (FIG. 12, panel A). At the baseline, Patient 1 was patient febrile, receiving $O_2$ through a facemask, $FiO_2$ 0.4, $PaO_2$ 86 mmHg, LDH 374 U/L, CRP 100 mg/L. The CT scan obtained on discharge, 7 days after the administration of an anti-GM-CSFRα antibody, showed significant reduction and regression of these findings (FIG. 12, panel B). The Patient 1 at day 7 was afebrile, on room air, with $SpO_2$ of 98%, CRP 12.5 mg/L, and LDH normalized. Similarly, CT scan of Patient 2 at baseline showed extensive involvement of right lung with posterior large consolidation area and air bronchogram, and ground-glass opacities and crazy paving pattern predominantly on the left side of the lung (FIG. 12, panel C). At the baseline, Patient 2 was febrile, receiving high-low $O_2$ through a facemask with reservoir bag+12 hours/day of CPAP, $PaO_2$ 176 mmHg, LDH 944 U/L, CRP 177 mg/L. CT scan of Patient on discharge, at 14 days after the administration of an anti-GM-CSFRα antibody showed significant improvement of the lung involvement (FIG. 12, panel D), and was afebrile, on room air, with $SpO_2$ 98%, CRP 28.2 mg/L, and LDH normalized.

Overall, the data in this example illustrates that the treatment with a single dose of anti-GM-CSFRα antibody was effective in treating patients with severe COVID-19 pneumonia and systemic hyper-inflammation. The clinical status of the treated patients at day 14 and at day 28 day both show that the treatment with an anti-GM-CSFRα increased the probability of survival and achieved early improvement as compared to the control group. Additionally, none of the treated patients has died or showed adverse effects, including, for example, no infections resulting from immune modulation by GM-CSF antagonism.

Based on improvement and/or adverse events, dosage and/or administration interval are adjusted accordingly.

Example 2. Phase 2/3 Study for the Treatment of COVID-19 with an Anti-GM-CSFRα Antibody This example illustrates a Phase 2/3, randomized, double-blind, placebo-controlled study to evaluate the efficacy and safety of anti-GM-CSFRα antibody treatment in adult subjects hospitalized with severe COVID-19 pneumonia and hyper-inflammation.

In this study, patients with severe COVID-19 pneumonia for evidence of hyper-inflammation status as demonstrated by elevated levels of one or more biomarkers (e.g., C-reactive protein and Lactate Dehydrogenase [LDH] as well as increased IL-6, ferritin, D-dimer, or erythrocyte sedimentation rate) are screened to identify the subgroup of patients for whom targeted immunomodulation could prevent worsening of pulmonary status, including the need for ventilatory support, with the aim ultimately to improve mortality and to reduce the need for ventilatory support (i.e., prevent progression to invasive ventilation or death, and/or reduce days on ventilation for recently-ventilated patients).

A dose of up to 10 mg/kg (the highest tested in humans) may be required to confer significant pharmacodynamic effects in the lung to inhibit cytokine storm and prevent further lung damage. It would be reasonable to administer a single dose of anti-GM-CSFRα antibody at levels up to 10 mg/kg in an attempt to provide desired pharmacodynamics in COVID-19 patients, where direct inhibition of GM-CSF in the lung may be a requirement. Hypothetically, a dose of 3 mg/kg may be sufficient and reasonable to be tested, but only if the higher proposed dosages, i.e., 10 mg/kg and 6 mg/kg are found not to be safe for the target population or if efficacy, if observed, is not apparently dose-dependent. Given the lethality of pulmonary complications from COVID-19, in Phase 2, higher doses (higher than 3 mg/kg, given that this dose is apparently sufficient to completely block the signaling axis only in the periphery) will be tested first.

A single IV infusion of 10 mg/kg or 6 mg/kg will be administered to study subjects. Immediate access to an emergency crash cart will be required. The infusion should last approximately one hour. Premedication to avoid or treat potential infusion-related reaction is at the discretion of the investigator. The initial 15 minutes of infusion will be administered at an infusion rate to allow for delivery of approximately ⅙ of the total volume of the infusion. If no moderate or severe infusion reactions are observed, the rate will be doubled for the next 15 minutes. After the first 30 minutes the rate will be increased to deliver another 50% of the total volume, if the infusion continues to be well tolerated. At any time during the infusion, if a moderate reaction occurs, the infusion will be stopped and restarted at the discretion of the investigator only after the events have resolved. The infusion rate should be re-started at the last rate tolerated by the subject. The infusion should be stopped permanently if a severe reaction is observed. The infusion rate may be adjusted to allow for a slower risk-based infusion rate. Slow infusion rates are the most efficient mitigation factor to potential infusion-related reactions.

Objectives

The primary objective of this study is to evaluate the clinical efficacy of a single intravenous (IV) dose of anti-GM-CSFRα antibody (10 mg/kg or 6 mg/kg) relative to placebo in adult subjects hospitalized with severe Corona Virus Disease 2019 (COVID-19) pneumonia and hyper-inflammation to reduce progression to respiratory failure or death. The secondary objective of this study is to assess impact of treatment on time to return to room air, changes in need for invasive ventilation or critical care over time, mortality, respiratory parameters, and safety of a single IV dose of anti-GM-CSFRα antibody (10 mg/kg or 6 mg/kg) relative to placebo in adult subjects hospitalized with severe COVID-19 pneumonia and hyper-inflammation. Additionally, the study is done to assess supplemental clinical information, including temporal changes in serum markers of hyper-inflammation and virology. Health economic outcomes will also be evaluated.

Methodology

Figure 13:
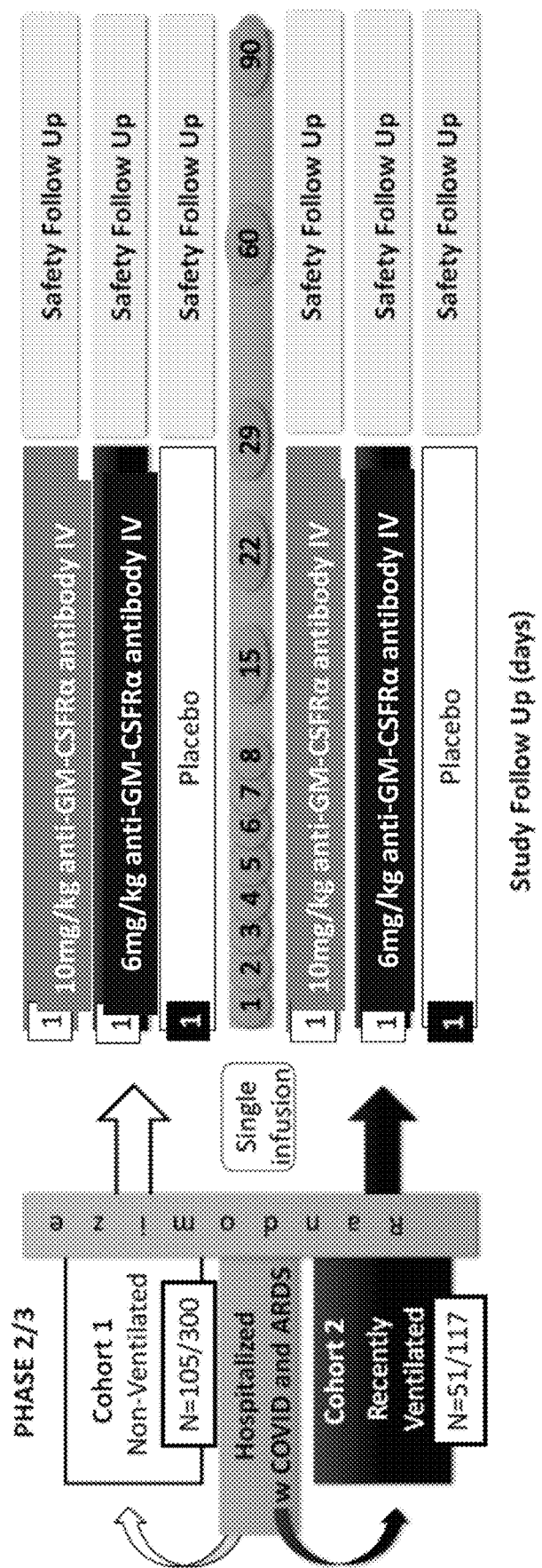
FIG. 13 is an exemplary study schematic of a Phase 2/3, randomized, double-blind, placebo-controlled study to evaluate the efficacy and safety of anti-GM-CSFRα antibody treatment in adult subjects hospitalized with severe COVID-19 pneumonia and hyper-inflammation.

This is an interventional, randomized, double-blind, placebo-controlled study encompassing 2 development phases (Phase 2 and Phase 3). The Phase 2 portion of the study is intended to evaluate the efficacy and safety of 2 dose levels of anti-GM-CSFRα antibody relative to placebo (standard of care) in subjects who have tested positive for SARS-CoV-2 and have x-ray/CT evidence of bilateral pneumonia, active or recent fever, and clinical laboratory results indicative of hyper-inflammation. The Phase 3 portion is intended to confirm Phase 2 efficacy and safety findings. In both Phase 2 and Phase 3, subjects will be enrolled into 2 cohorts: Cohort 1 will include non-intubated, hospitalized subjects who require supplemental oxygen to maintain SpO2≥92%, ie, "non-ventilated" subjects; Cohort 2 will include hospitalized subjects for whom mechanical ventilation was recently initiated (within 48 hours prior to randomization), ie, "ventilated" subjects. Following Screening, enrolled subjects in each cohort will be randomized 1:1:1 to receive anti-GM-CSFRα antibody 10 mg/kg or 6 mg/kg, or placebo as a single IV infusion (Day 1). There will be a seamless transition in enrollment of subjects in both cohorts between the Phase 2 and Phase 3 portions of the study. For each cohort, once the last subject in Phase 2 is enrolled, all subsequent subjects will be considered Phase 3 subjects. This will allow for continued enrollment during the analysis of the Phase 2 cohort-specific data. Once the last subject in Phase 2 completes Day 15, primary efficacy and safety analyses of the Phase 2 data will be conducted by the Sponsor. Following demonstration of efficacy and safety in Phase 2, the Phase 3 portion of the study will be continued/completed. An exemplary study schematic is shown in FIG. 13.

Number of Subjects (Exemplary)
    Phase 2: Approximately 156 subjects
        Cohort 1: Approximately 105 non-ventilated subjects
        Cohort 2: Approximately 51 ventilated subjects
    Phase 3: Approximately 417 subjects
        Cohort 1: Approximately 300 non-ventilated subjects
        Cohort 2: Approximately 117 ventilated subjects The sample size for the Phase 3 part of the study may be modified after review of the Phase 2 data. Phase 2 subjects will not be included in the analysis of Phase 3 results.

Diagnosis and Main Criteria for Inclusion

Adult subjects who have tested positive for SARS-CoV-2 with confirmed pneumonia and hyper-inflammation.

Investigational Product, Dosage and Mode of Administration

An anti-GM-CSFRα antibody (mavrilimumab), 10 mg/kg or 6 mg/kg (total dose not to exceed 1000 mg), administered as a single IV infusion over approximately 60.

Duration of Treatment

Subjects will receive a single IV dose of anti-GM-CSFRα antibody or placebo infused approximately 60 minutes on Day 1.

Reference Therapy, Dose and Mode of Administration

Placebo administered as a single IV infusion over approximately 60 minutes.

Criteria for Evaluation

The following efficacy endpoints will be used for both the Phase 2 and Phase 3 parts of the study. Endpoints will be evaluated for both Cohorts 1 and 2, unless otherwise specified.

Efficacy

Primary Efficacy Endpoint
    Cohort 1 (Non-Ventilated Subjects)

Proportion of subjects alive and without respiratory failure at Day 15, where respiratory failure is defined as the need for high flow oxygen (HFO), non-invasive ventilation (NIV), invasive mechanical ventilation (IMV), or extracorporeal membrane oxygenation (ECMO).

Respiratory failure status will be evaluated based on the National Institute of Allergy and Infectious Diseases (NIAID) clinical outcome 8-point ordinal scale. Subjects whose clinical outcome meets NIAID categories 2 or 3 will be considered as having respiratory failure.

1. Death;
2. Hospitalized, on invasive mechanical ventilation or ECMO;
3. Hospitalized, on non-invasive ventilation or high flow oxygen devices;
4. Hospitalized, requiring supplemental oxygen;
5. Hospitalized, not requiring supplemental oxygen—requiring ongoing medical care (COVID-19 related or otherwise);
6. Hospitalized, not requiring supplemental oxygen—no longer requires ongoing medical care;
7. Not hospitalized, limitation on activities and/or requiring home oxygen;
8. Not hospitalized, no limitations on activities.

Cohort 2 (Ventilated Subjects)

The primary efficacy endpoint is mortality rate, defined as the proportion of subjects who die by Day 15.

Key Secondary Endpoints
   Key secondary efficacy endpoints will be examined based on the hierarchical order as specified below:
   Cohort 1 (non-ventilated subjects)
   1. Time to return to room air by Day 15
      Defined as time from the date of randomization to the start of a period of 24 hours while breathing room air (NIAID scale ≥5), or discharge from the hospital, whichever occurs first. Subjects who die before Day 15 will be censored at Day 15.
   2. Time to 2-point clinical improvement by Day 15
      Defined as time from randomization to a 2-point improvement on the NIAID 8-point ordinal scale, or discharge from the hospital, whichever comes first. Subjects who die before Day 15 will be censored at Day 15.
   3. Mortality rate at Day 29
   Cohort 2 (Ventilated Subjects)
   1. Time to 1-point clinical improvement by Day 15
      Defined as time from randomization to a 1-point improvement on the NIAID 8-point ordinal scale, or discharge from the hospital, whichever comes first. Subjects who die before Day 15 will be censored at Day 15.
   2. Mortality rate at Day 29
Other Secondary Endpoints
   Proportion of subjects alive and without respiratory failure at Day 15 (Cohort 2)
   Proportion of subjects alive and without respiratory failure at Day 29
   Time to return to room air by Day 29
   Time to 1-point clinical improvement by Day 15 (Cohort 1)
   Time to 2-point clinical improvement by Day 15 (Cohort 2)
   Time to 1-point clinical improvement by Day 29
   Time to 2-point clinical improvement by Day 29
   Respiratory failure-free survival by Day 15 (Cohort 1)
      Subjects who have died or who have respiratory failure will be considered as events. Subjects who have no events will be censored at Day 15
   Respiratory failure-free survival by Day 29 (Cohort 1)
   Proportion of subjects who return to room air by Day 15 (Cohort 1)
      Return to room air is defined as a period of 24 hours while breathing room air or discharge from the hospital, whichever occurs first. Subjects who die before Day 15 will be considered treatment failures and included in the denominator for the calculation of proportion.
   Proportion of subjects who return to room air at Day 29
   Mortality rate at Day 15 (Cohort 1)
   Overall survival by Day 29 defined as time from date of randomization to the date of death; subjects still alive will be censored at Day 29
   Odds ratio for clinical status based on the NIAID 8-point ordinal scale over time at Days 4, 8, 15, 22, and 29
   Clinical status (NIAID 8-point scale) over time through Day 29
   Days alive and out of hospital through Day 90
Safety Endpoints and Oversight
   Safety endpoints will include adverse events, laboratory parameters, vital signs, ECG, and other condition-specific events. Frequency and specific details will be described in the Clinical Monitoring Plan.
   A Safety Review Committee (SRC) including safety physicians from the Sponsor, the Sponsor's contract research organization (CRO), and at least 1 medical expert in COVID-19 treatment will meet periodically to review AEs/SAEs, reasons for study discontinuations, and key clinical and laboratory assessments. The initial SRC meeting will be triggered once 4 subjects have completed Day 8. SRC members will be blinded to treatment assignment.
   A Data Monitoring Committee (DMC) will be established by the Sponsor to conduct periodic reviews of unblinded safety data from study Phases 2 and 3. The initial meeting will be triggered at 1 month after enrollment of the first patient. More details on the DMC are provided in the protocol and the DMC charter.
Statistical Methods
   The df Phase 2 and Phase 3 parts of this study and the cohorts within each phase will be independently analyzed unless otherwise specified.
Analysis Sets
   Intent-to-Treat Analysis Set
   All randomized subjects will be included in the intent-to-treat (ITT) analysis set.
   Modified Intent-to-Treat Analysis Set
   All randomized subjects who received study drug will be included in the modified intent-to-treat (mITT) analysis set.
   Safety Analysis Set
   All randomized subjects who received study drug will be included in the safety analysis set.
   Per-Protocol Analysis Set
   All mITT/ITT subjects without protocol deviations deemed to impact efficacy or ethical conduct will be included in the per-protocol (PP) analysis set.
Randomization Strata
   There will be 3 stratification factors for randomization:
   1. Use of approved standard of care antiretroviral therapy: yes vs. no
   2. Age: <65 vs. ≥65 years
   3. Acute respiratory distress syndrome (ARDS) status by PaO2/FiO2*: normal-mild (>200 mmHg) vs. moderate-severe (≤200 mmHg). ARDS status will only be used for Cohort 1 (non-ventilated subjects).
      * If PaO2 is unavailable, use SpO2/FiO2: normal-mild (>235 mmHg) vs. moderate-severe (≤235 mmHg).
Statistical Analysis
   All statistical analyses will be performed using SAS® Version 9.4 or higher. Descriptive statistics will be presented for all endpoints and will include number of subjects (n), mean, standard deviation (SD), median, interquartile range, minimum and maximum for continuous variables, and frequency and percentage for categorical and ordinal variables.
   Efficacy Analysis
   All efficacy analyses will be based on the mITT for the Phase 2 endpoints and based on the ITT analysis set for the Phase 3 endpoints. Analyses based on other analysis sets will be considered as sensitivity analyses.
   Primary Efficacy Endpoint
   For the Phase 2 part of the study, the Fisher's exact test will be performed for the primary efficacy endpoint for both cohorts.
   For the Phase 3 part of the study, the Cochran-Mantel-Haenszel (CMH) test adjusted by the randomization strata will be used to test the primary efficacy endpoint for Cohort 1 (non-ventilated subjects). Fisher's exact test will be performed for Cohort 2 (ventilated subjects).
   The number of subjects and percentages will be summarized by treatment. The 80% (for Phase 2) and 95% (for Phase 3) confidence intervals will also be provided as appropriate.

Secondary Efficacy Endpoint

Time to return to room air, time to clinical improvement, and all other time to event endpoints will be analyzed using log-rank test stratified by the randomization strata. The hazard ratio for anti-GM-CSFRα antibody vs. placebo and the corresponding Wald 80% (for Phase 2) and 95% (for Phase 3) CI will be calculated based on a Cox proportional-hazards model with treatment as covariate, stratified by randomization strata.

Mortality rate and all other binary endpoints in both cohorts for Phase 2, and in Cohort 2 only for Phase 3 will be analyzed using the Fisher's exact test. For Cohort 1 in Phase 3 they will be analyzed using a CMH test adjusted by the randomization strata.

Safety Analysis

All safety summaries will be presented for the safety analysis set. No formal statistical analysis of safety endpoints will be performed.

Descriptive statistics will be used to summarize all safety endpoints by treatment group and/or study visit. Data summaries will display parameters such as incidence of adverse events, clinical laboratory variables, vital signs, body weight and body mass index, ECG parameters, and physical examinations, where available.

Other Analyses

Pharmacokinetic parameters of anti-GM-CSFRα antibody will be summarized. The association between serum pharmacodynamic biomarkers and assessments of clinical response including antidrug antibodies (ADAs) will be explored. Parameters of mechanical ventilation, respiratory status, SOFA/qSOFA, and health care resource utilization (eg, days and/or length in hospital/ICU) will be summarized.

Interim Analysis

There is no interim analysis planned for the Phase 2 part of the study. Instead the Sponsor will conduct a primary efficacy analysis (ie, review of unblinded study results) when the last subject in Phase 2 completes the Day 15 assessments.

For the Phase 3 study part, one interim analysis for each cohort will be done when 50% of the subjects are randomized and have been followed up for 15 days. The DMC will review the unblinded interim analysis results and recommend if the trial should be stopped for efficacy based on the pre-specified early stopping rule. There is no futility analysis planned.

The O'Brien-Fleming stopping boundary based on the Lan-DeMets alpha spending function (Jennison and Turnbull, 2000) will be applied at the interim and final analyses. If the information fraction at the interim analysis is 50%, the two-sided significance levels at the interim and final analyses will be given by $\alpha 1=0.0030$ and $\alpha 2=0.0490$. The significance levels will be calculated based on the actual information fraction at the interim analysis.

Sample Size Estimation

Phase 2

Approximately 156 subjects will be randomized to the Phase 2 part of this study.

Sample size estimation for Cohort 1 (non-ventilated subjects) in Phase 2 is based on the primary efficacy endpoint proportion of subjects alive and without respiratory failure at Day 15, using a Fisher's exact test.

Approximately 105 subjects will be randomized with a 1:1:1 allocation ratio. Assuming the proportions of subjects alive and without respiratory failure at Day 15 are 90% and 65% for the active treatment arm and placebo arm, respectively, 35 subjects per arm will achieve a minimum 80% power for a pairwise comparison versus control when the two-sided alpha value is 0.20.

Sample size for Cohort 2 (ventilated subjects) in Phase 2 is based on the primary efficacy endpoint mortality rate at Day 15, using a Fisher's exact test. Approximately 51 subjects will be randomized with a 1:1:1 allocation ratio. Assuming the mortality rates at Day 15 are 40% and 80% for the active treatment arm and placebo arm, respectively, 17 subjects per arm will achieve an 80% power for a pairwise comparison versus control when the two-sided alpha value is 0.20.

Phase 3

Approximately 417 subjects will be randomized to the Phase 3 part of this study.

Sample size for Cohort 1 (non-ventilated subjects) of the Phase 3 part is determined based on the primary efficacy endpoint proportion of subjects alive and without respiratory failure at Day 15 using a CMH test. Approximately 300 subjects will be randomized with a 1:1:1 allocation ratio. Assuming the proportions for the active arm and placebo arm are 90% and 70% respectively, approximately 100 subjects per arm are required to achieve a 90% power for a pairwise comparison versus control when the two-sided alpha value is 0.025.

Sample size for Cohort 2 (ventilated subjects) of the Phase 3 part is determined based on the mortality rate at Day 15 using a Fisher's exact test. Approximately 117 subjects will be randomized with a 1:1:1 allocation ratio. Assuming the mortality rates for the active arm and placebo arm are 40% and 80% respectively, approximately 39 subjects per arm are required to achieve a 90% power for a pairwise comparison versus control when the two-sided alpha value is 0.025.

Sample size for the Phase 3 part of the study may be modified after review of the Phase 2 data.

Multiplicity Adjustment

The cohorts within the Phase 2 and Phase 3 study parts will be analyzed separately unless otherwise specified.

No multiplicity adjustment will be done for the Phase 2 part. Type I error rate for each Phase 2 cohort is at a two-sided alpha value of 0.2.

There are three sources of multiplicity in the Phase 3 part of this trial:
- Analysis of the primary/key secondary endpoints
- Analysis of the dose-placebo comparisons
- Analysis of treatment effects at the interim and the final analyses Multiplicity adjustment will be done to guarantee strong control of the overall Type I error rate with respect to all three sources of multiplicity at a two-sided alpha value of 0.05 within each cohort.

Eligibility Criteria

Inclusion Criteria

Subjects must meet all the following inclusion criteria to be eligible for enrollment.
1. Subject (or legally authorized representative) is able and willing to provide informed consent, which includes compliance with study requirements and restrictions listed in the consent form. Consent must be performed per institutional regulations.
2. Age of ≥18 years
3. Positive SARS-CoV-2 (2019-nCoV) test within 14 days prior to randomization
4. Hospitalized for SARS-CoV-2
5. Bilateral pneumonia on chest x-ray or computed tomography (CT)

6. Active fever or recently documented fever within 72 hours prior to randomization (≥100.4° F. or ≥38° C.)
7. At least one of the following:
   Ferritin>500 ng/mL
   CRP>5 mg/dL
   D-dimer>1,000 ng/mL
   LDH>250 U/L
8. For Cohort 1: Receiving any form of non-invasive ventilation OR oxygenation to maintain SpO2≥92% and not-intubated [examples include nasal cannula, face mask, venturi mask, high-flow nasal cannula, and non-invasive ventilation (NIV) or non-invasive positive pressure ventilation (NIPPV)]
9. For Cohort 2: Recently ventilated with mechanical ventilation beginning within 48 hours prior to randomization Exclusion Criteria General Exclusion Criteria 1. Onset of COVID-19 symptoms or positive COVID-19 test result >14 days prior to randomization
2. Hospitalized >7 days prior to randomization
3. [For Cohort 1 only] Need for invasive mechanical ventilation
4. Need for ECMO
5. Serious prior or concomitant illness that in the opinion of the Investigator precludes the subject from enrolling in the trial, including (but not limited to):
   History of pulmonary alveolar proteinosis (PAP)
   History of immunodeficiency (congenital or acquired)
   History of solid-organ or bone marrow transplant
   Current systemic autoimmune or autoinflammatory disease(s) requiring systemic immune-modulating drugs
   History of or active cancer within the last 10 years—except for basal and squamous cell carcinoma of the skin or in situ carcinoma of the cervix treated and considered cured
   Severe and uncontrolled pulmonary disease other than COVID-19 pneumonia (eg, asthma, chronic obstructive pulmonary disease [COPD], or others)
   Pre-existing severe left ventricular systolic dysfunction (ie, left ventricular ejection fraction [LVEF]<35%)
   Known active tuberculosis (TB) determined by history and local standard of care, or history of incompletely treated TB or at high risk for latent TB (exposure or prior incarceration)
   Concomitant uncontrolled systemic bacterial or fungal infection
   Concomitant respiratory viral infection other than COVID-19 that, in the opinion of the Investigator, represents a higher mortality risk (eg, SARS, MERS)
   History of chronic liver disease with portal hypertension
6. Recent treatment with cell-depleting biological therapies (eg, anti-CD20) within 12 months, cell-depleting biological therapies (such as anti-tumor necrosis factor [TNF], anakinra, anti-IL-6 receptor [eg, tocilizumab], or abatacept) within 8 weeks (or 5 half-lives, whichever is longer), treatment with alkylating agents within 12 weeks, treatment with cyclosporine A, azathioprine, cyclophosphamide, mycophenolate mofetil (MMF), COVID-19-immune plasma, or other immunosuppressant within 4 weeks prior to randomization
7. Recent treatment with intramuscular live (attenuated) vaccine within 4 weeks prior to randomization
8. Corrected QT interval by Federicia method (QTcF) on Screening ECG≥450 ms
9. Chronic or recent (within 7 days prior to randomization) corticosteroid use >10 mg/day
10. Enrolled in another investigational study of a medical intervention within 30 days prior to randomization
11. Known hypersensitivity to anti-GM-CSFRα antibody or any of its excipients
12. In the opinion of the Investigator, unable to comply with the requirements to participate in the study
13. Female subjects must be:
    postmenopausal, defined as at least 12 months post cessation of menses (without an alternative medical cause), or
    permanently sterile following documented hysterectomy, bilateral salpingectomy, bilateral oophorectomy, or tubal ligation or having a male partner with vasectomy as affirmed by the subject, or
    nonpregnant, nonlactating, and if sexually active having agreed to use a highly effective method of contraception (ie, hormonal contraceptives associated with inhibition of ovulation or intrauterine device [IUD], or intrauterine hormone-releasing system [IUS], or sexual abstinence) from Screening Visit until Day 90.
14. Male subjects must have documented vasectomy or if sexually active must agree to use a highly effective method of contraception with their partners of child-bearing potential (ie, hormonal contraceptives associated with the inhibition of ovulation or intrauterine device [IUD], or intrauterine hormone-releasing system [IUS], or sexual abstinence) from Screening until Day 90. Male subjects must agree to refrain from donating sperm during this time period.
15. At Screening blood tests, any of the following:
    Aspartate transaminase (AST)>5×ULN (Upper Limit of Normal)
    Alanine transaminase (ALT)>5×ULN (Upper Limit of Normal)
    Hemoglobin<7.5 g/dL
    Neutrophils<1,500/mm3
    Absolute platelet count<50,000/mm3
    Creatinine clearance (CrCl)<30 mL/min (by Cockcroft-Gault formula)

Example 3. Investigator-Initialed Study of Anti-GM-CSFRα Antibody in Severe COVID-10 Pneumonia and Hyperinflammation This example illustrates an investigator-imitated study to evaluate the efficacy and safety of an anti-GM-CSFRα antibody versus placebo on top of standard of care therapy in patients with severe COVID-19 pneumonia and hyperinflammation.

The study was a randomized, double-blind, placebo-controlled study, and enrolled 40 patients with severe COVID-19 pneumonia (all patients presented with pneumonia and hypoxia: all patients required supplemental oxygen, 50% of patients required non-invasive ventilation, none required mechanical ventilation at baseline; median PaO2/FiO2 ratio 137) and hyperinflammation [median C-reactive protein 13.1 mg/dL). Concomitant medications at baseline included corticosteroids (65% of patients) and remdesivir (75% of patients). Patients were randomized 1:1 to a single intravenous (IV) infusion of anti-GM-CSFRα antibody 6 mg/kg (n=21) or placebo (n=19) and were followed for at least 60 days. The primary endpoint was the proportion of patients alive and off of supplemental oxygen at Day 14.

Data showed an early signal of efficacy, with trends toward clinical improvement as well as lower mortality and shorter duration of mechanical ventilation in patients treated with anti-GM-CSFRα antibody on top of corticosteroids, including dexamethasone, and/or remdesivir.

- There was a 20% relative increase in the primary efficacy endpoint, the proportion of patients alive and off supplemental oxygen at Day 14 (anti-GM-CSFRα antibody: 57.1% [n=21]; placebo: 47.4% [n=19]).
- There was a 20.7% relative increase in the secondary efficacy endpoint, the proportion of patients alive and without respiratory failure at Day 28 (anti-GM-CSFRα antibody: 95.2%; placebo: 78.9%).
- There was 1 death (4.8%) in the anti-GM-CSFRα antibody arm by Day 28, compared to 3 deaths (15.8%) in the placebo arm. By Day 60 there was 1 death (4.8%) in the anti-GM-CSFRα antibody arm, compared to 4 deaths (21.1%) in the placebo arm.
- While the percentage of patients who progressed to mechanical ventilation was similar between treatment arms (anti-GM-CSFRα antibody: 23.8% [n=5]; placebo: 21.1% [n=4]), the median (interquartile) duration of mechanical ventilation was shorter in the anti-GM-CSFRα antibody arm (12 [9.0, 18.0] days) compared to the placebo arm (17 [11.0, 24.5] days). Additionally, 4 of the 5 patients who progressed to mechanical ventilation in the mavrilimumab arm recovered by Day 28, whereas all patients in the placebo arm who progressed to mechanical ventilation died by Day 28.
- There was no difference in serious adverse events between anti-GM-CSFRα antibody-treated patients and placebo recipients.

Consistent with data from the open-label treatment protocol described in Example 1, these data showed encouraging trends of reduced mortality and duration of mechanical ventilation in patients treated with anti-GM-CSFRα antibody, especially when considering that many patients in this placebo-controlled study had been already treated with remdesivir and/or corticosteroids.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

We claim:

1. A method of treating a subject infected with a coronavirus, wherein the subject has developed hyper-inflammation and pneumonia, comprising administering to the subject a granulocyte-macrophage colony-stimulating factor (GM-CSF) antagonist at a single dose of between 5 mg/kg and 10 mg/kg, wherein the GM-CSF antagonist is mavrilimumab, wherein the coronavirus is a SARS-CoV-2.

2. The method of claim 1, wherein mavrilimumab is administered intravenously.

3. The method of claim 2, wherein mavrilimumab is administered by intravenous infusion.

4. The method of claim 1, wherein mavrilimumab is administered at 6 mg/kg.

5. The method of claim 1, wherein mavrilimumab is administered at 10 mg/kg.

6. The method of claim 1, wherein the single administration of mavrilimumab improves, stabilizes, or reduce one or more symptoms of hyper-inflammation or pneumonia.

7. The method of claim 6, wherein the one or more symptoms are associated with SARS, MERS, or COVID-19.

8. The method of claim 6, wherein the single administration of mavrilimumab is sufficient to improve, stabilize or reduce one or more symptoms for longer than seven days.

9. The method of claim 8, wherein the single administration of mavrilimumab sufficient to improve, stabilize or reduce one or more symptoms for longer than 20 or 29 days.

10. The method of claim 6, wherein the single administration of mavrilimumab results in resolution of fever within 7, days, 5 days, or 2 days.

11. The method of claim 10, wherein the single administration of mavrilimumab results in resolution of fever within 1 day.

12. The method of claim 1, wherein the single administration of mavrilimumab improves the subject's lung function such that supplemental oxygen is not needed.

13. The method of claim 1, wherein the single administration of mavrilimumab prevents a subject from requiring mechanical ventilation.

14. The method of claim 1, wherein the subject is administered the GM-CSF antagonist after receiving respiratory support.

15. The method of claim 14, wherein the respiratory support is supplemental oxygen, non-invasive ventilation or non-invasive mechanical ventilation.

16. The method of claim 14, wherein the respiratory support is mechanical ventilation.

17. The method of claim 16, wherein the administered the GM-CSF antagonist reduces the duration of mechanical ventilation.

18. The method of claim 1, wherein the subject is administered the GM-CSF antagonist prior to receiving respiratory support.

19. The method of claim 1, wherein the single administration of mavrilimumab decreases an area of "ground-glass" opacity in the lung.

20. The method of claim 1, wherein the single administration of mavrilimumab prevents death of the subject.

21. The method of claim 1, wherein the single administration of mavrilimumab results in discharge from the hospital and/or weaning off from on-going medical care within 10 days.

22. The method of claim 21, wherein the single administration of mavrilimumab results in discharge from the hospital and/or weaning off from on-going medical care within 7 days.

23. The method of claim 1, wherein the subject has an elevated level of an inflammation marker.

24. The method of claim 23, wherein the inflammation marker is a presence of ground-glass opacity in the lung.

25. The method of claim 23, wherein the elevated level of the inflammation marker is c-reactive protein (CRP)≥1 mg/dL in the subject's serum.

26. The method of claim 1, wherein the subject is administered an antiviral drug.

27. The method of claim 26, wherein the antiviral drug is remdesivir.

28. The method of claim 1, wherein the subject is administered corticosteroids.

* * * * *